United States Patent
Easton et al.

(10) Patent No.: US 9,884,812 B2
(45) Date of Patent: Feb. 6, 2018

(54) USE OF DDX3X INHIBITORS FOR THE TREATMENT OF PNEUMOVIRUS INFECTIONS

(71) Applicant: UNIVERSITY OF WARWICK, West Midlands (GB)

(72) Inventors: Andrew Easton, West Midlands (GB); Phillip Gould, West Midlands (GB); Andrew Marsh, West Midlands (GB)

(73) Assignee: UNIVERSITY OF WARWICK (GB)

( * ) Notice: Subject to any disclaimer, the term of this patent is extended or adjusted under 35 U.S.C. 154(b) by 0 days.

(21) Appl. No.: 15/124,748

(22) PCT Filed: Mar. 12, 2015

(86) PCT No.: PCT/GB2015/050724
§ 371 (c)(1),
(2) Date: Sep. 9, 2016

(87) PCT Pub. No.: WO2015/136292
PCT Pub. Date: Sep. 17, 2015

(65) Prior Publication Data
US 2017/0166519 A1     Jun. 15, 2017

(30) Foreign Application Priority Data

Mar. 12, 2014 (GB) .................................. 1404372.3

(51) Int. Cl.
| | |
|---|---|
| *A61K 31/535* | (2006.01) |
| *C07C 275/30* | (2006.01) |
| *C07C 275/42* | (2006.01) |
| *C07C 275/40* | (2006.01) |
| *C07C 323/44* | (2006.01) |
| *C07D 213/75* | (2006.01) |
| *C07C 317/42* | (2006.01) |
| *C07D 239/42* | (2006.01) |
| *C07D 295/16* | (2006.01) |
| *G01N 33/573* | (2006.01) |
| *G01N 33/53* | (2006.01) |
| *A61K 31/5375* | (2006.01) |

(52) U.S. Cl.
CPC ........ *C07C 275/30* (2013.01); *A61K 31/5375* (2013.01); *C07C 275/40* (2013.01); *C07C 275/42* (2013.01); *C07C 317/42* (2013.01); *C07C 323/44* (2013.01); *C07D 213/75* (2013.01); *C07D 239/42* (2013.01); *C07D 295/16* (2013.01); *C12Y 306/04013* (2013.01); *G01N 33/5308* (2013.01); *G01N 33/573* (2013.01); *G01N 2333/135* (2013.01); *G01N 2333/914* (2013.01); *G01N 2500/02* (2013.01)

(58) Field of Classification Search
None
See application file for complete search history.

(56) References Cited

U.S. PATENT DOCUMENTS 4,405,644 A     9/1983 Kabbe et al.

FOREIGN PATENT DOCUMENTS

| EP | 0656350 | 6/1995 |
|---|---|---|
| WO | WO 99/32463 | 7/1999 |
| WO | WO 00/50646 | 8/2000 |
| WO | WO 2004/014316 | 2/2004 |
| WO | WO 2005/100595 | 10/2005 |
| WO | WO 2011/039735 | 4/2011 |
| WO | WO 2011/145885 | 11/2011 |

OTHER PUBLICATIONS

Ahmadian et al. "Expression of the ORF-2 protein of the human respiratory syncytial virus M2 gene is initiated by a ribosomal termination-dependent reinitiation mechanism," The EMBO Journal, 2000, vol. 19, No. 11, pp. 2681-2689.
Amato et al. "Substituted 1-Phenyl-3-(pyridin-2-yl)urea Negative Allosteric Modulators of mGlu5: Discovery of a New Tool Compound VU0463841 with Activity in Rat Models of Cocaine Addiction," ACS Chemical Neuroscience, 2013, vol. 4, No. 8, pp. 1217-1228.
Angus et al. "Requirement of cellular DDX3 for hepatitis C virus replication is unrelated to its interaction with the viral core protein," Journal of General Virology, 2010, vol. 91, pp. 122-132.
Arhel et al. "Host proteins involved in HIV infection: New therapeutic targets," Biochimica et Biophysica Acta, 2010, vol. 1802, pp. 313-321.
Baltimore "Expression of Animal Virus Genomes," Bacteriological Reviews, Sep. 1971, vol. 35, No. 3, pp. 235-241.
Belon et al. "Helicase inhibitors as specifically targeted antiviral therapy for hepatitis C," Future Virol., May 2009, vol. 4, No. 3, pp. 277-293.
Bermingham et al. "The M2-2 protein of human respiratory syncytial virus is a regulatory factor involved in the balance between RNA replication and transcription," PNAS, Sep. 1999, vol. 96, pp. 11259-11264.
Bizebard et al. "Studies on Three *E. coli* DEAD-Box Helicases Point to an Unwinding Mechanism Different from that of Model DNA Helicases," Biochemistry, 2004, vol. 43, pp. 7857-7866.
Borchers et al. "Respiratory Syncytial Virus—A Comprehensive Review," Clinic. Rev. Allerg. Immunol., 2013, vol. 45, No. 3, pp. 331-379.

(Continued)

*Primary Examiner* — Jeffrey H Murray
(74) *Attorney, Agent, or Firm* — Sheridan Ross P.C.

(57) ABSTRACT

The invention relates to a DDX3X inhibitor for use in the treatment of pneumovirus infection in a mammal, wherein the DDX3X inhibitor may be a compound of Formula (I) wherein y, Z, $R^1$, X, L, $R^a$ and $R^b$ are as defined herein. The invention also relates to compounds of Formula (I).

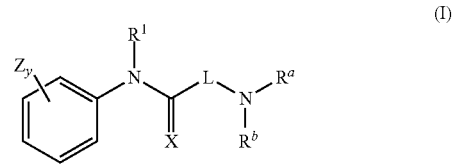

(I)

25 Claims, 17 Drawing Sheets

(56) References Cited

OTHER PUBLICATIONS

Botlagunta et al. "Oncogenic role of DDX3 in breast cancer biogenesis," Oncogene, 2008, vol. 27, pp. 3912-3922.
Botlagunta et al. "Expression of DDX3 is Directly Modulated by Hypoxia Inducible Factor-1 Alpha in Breast Epithelial Cells," PLOS One, Mar. 2011, vol. 6, No. 3, e17563.
Breitler et al. "Synthesis of Unsymmetrical Diarylureas via Pd-Catalyzed C—N Cross-Coupling Reactions," Organic Letters, 2011, vol. 13, No. 12, pp. 3262-3265.
Bromidge et al. "Model Studies on a Synthetically Facile Series of N-Substituted Phenyl-N'-pyridin-3-yl Ureas Leading to 1-(3-Pyridylcarbamoyl)indolines that are Potent and Selective 5-HT2C/2B Receptor Antagonists," Bioorganic & Medicinal Chemistry, 1999, vol. 7, pp. 2767-2773.
Bushman et al. "Host Cell Factors in HIV Replication: Meta-Analysis of Genome-Wide Studies," PLOS Pathogens, May 2009, vol. 5, No. 5, e10000437, 12 pages.
Chao et al. "DDX3, a DEAD Box RNA Helicase with Tumor Growth-Suppressive Property and Transcriptional Regulation Activity of the p21waf1/cip1 Promoter, is a Candidate Tumor Suppressor," Cancer Res., Jul. 2006, vol. 66, No. 13, pp. 6579-6588.
Clayden et al. "Synthesis and Stacked Conformations of Symmetrical and Unsymmetrical Oligo-ureas of Metaphenylenediamine," J. Org. Chem., 2007, vol. 72, No. 7, pp. 2302-2308.
Dutta et al. "Synthesis and Biological Activities of Some N6- and N9-Carbamoyladenines and Related Ribonucleosides," Journal of Medicinal Chemistry, 1977, vol. 20, No. 12, pp. 1598-1607.
Dyson "Studies in the Colour Reactions of Organic Compounds, Part I, the Colour Reactions of Arylthioureas." J. Chem. Soc. 1934, pp. 174-177.
Evans "The Rise of Azide-Alkyne 1,3-Dipolar 'Click' Cycloaddition and its Application to Polymer Science and Surface Modification," Aust. J. Chem., 2007, vol. 60, pp. 384-395.
Geissler et al. "The DEAD-box helicase DDX3 supports the assembly of functional 80S ribosomes," Nucleic Acids Research, 2012, vol. 40, No. 11, pp. 4998-5011.
Götz et al. "Routine Microsecond Molecular Dynamics Simlulations with AMBER on GPUs. 1. Generalized Born," Journal of Chemical Theory and Computation, 2012, vol. 8, pp. 1542-1555.
Gould et al. "Coupled Translation of the Respiratory Syncytial Virus M2 Open Reading Frames Requires Upstream Sequences," The Journal of Biological Chemistry, Jun. 2005, vol. 280, No. 23, pp. 21972-21980.
Gould et al. "Coupled Translation of the Second Open Reading Frame of M2 mRNA is Sequence Dependent and Differs Significantly within the Subfamily Pneumovirinae," Journal of Virology, Aug. 2007, vol. 81, No. 16, pp. 8488-8496.
Hellen et al. "Internal ribosome entry sites in eukaryotic mRNA molecules," Genes & Development, 2001, vol. 15, pp. 1593-1612.
Hershey et al. "The Pathway and Mechanism of Initiation of Protein Synthesis," Translational Control of Gene Expression, 2000, vol. 39, pp. 33-88.
Hilbert et al. "The mechanism of ATP-dependent RNA unwinding by DEAD box proteins," Biol. Chem., Dec. 2009, vol. 390, pp. 1237-1250.
Ishikawa et al. "Synthesis of (−)-Oseltamivir by Using a Microreactor in the Curtius Rearrangement," Eur. J. Org. Chem., 2011, vol. 30, pp. 6020-6031.
Jackson et al. "The Mechanism of Eukaryotic Translation Initiation and Principles of Its Regulation," Nat Rev Mol Cell Biol., Feb. 2010, vol. 11, No. 2, pp. 113-127.
Jang et al. "A Segment of the 5' Nontranlated Region of Encephalomyocarditis Virus RNA Directs Internal Entry of Ribosomes during In Vitro Translation," Journal of Virology, Aug. 1988, vol. 62, No. 8, pp. 2636-2643.
Jankowsky "RNA Helicases at work: binding and rearranging," Trends Biochem Sci., Jan. 2011, vol. 36, No. 1, pp. 19-29.
Jarmoskaite et al. "DEAD-box proteins as RNA helicases and chaperones," WIREs RNA, Jan./Feb. 2011, vol. 2, pp. 135-152.
Kolb et al. "Click Chemistry: Diverse Chemical Function from a Few Good Reactions," Angew. Chem. Int. Ed., 2001, vol. 40, pp. 2004-2021.
Kozak "The Scanning Model for Translation: An Update," The Journal of Cell Biology, Feb. 1989, vol. 108, pp. 229-241.
Lai et al. "The DEAD-Box RNA Helicase DDX3 Associates with Export Messenger Ribonucleoproteins as well as Tip-associated Protein and Participates in Translational Control," Molecular Biology of the Cell, Sep. 2008, vol. 19, pp. 3847-3858.
Lee et al. "Human DDX3 functions in translation and interacts with the translation initiation factor eIF3," Nucleic Acids Research, 2008, vol. 36, No. 14, pp. 4708-4718.
Linder et al. "Bent out of Shape: RNA Unwinding by the DEAD-Box Helicase Vasa," Cell, Apr. 2006, vol. 125, pp. 219-221.
Linder et al. "From unwinding to clamping—the DEAD box RNA helicase family," Nature Reviews Molecular Cell Biology, Aug. 2011, vol. 12, pp. 505-516.
Linder et al. "Looking back on the birth of DEAD-box RNA helicases," Biochimica et Biophysica Acta, 2013, vol. 1829, pp. 750-755.
Luttermann et al. "A Bipartite Sequence Motif Induces Translation Reinitiation in Feline Calicivirus RNA," The Journal of Bioloogical Chemistry, Mar. 2007, vol. 282, No. 10, pp. 7056-7065.
Luttermann et al. "The importance of inter- and intramolecular base pairing for translation reinitiation on a eukaryotic bicistronic mRNA," Genes & Development, 2009, vol. 23, pp. 331-344.
McKay et al. "Urea Derivatives," Canadian Journal of Chemistry, 1952, vol. 30, No. 3, pp. 225-227.
Maga et al. "Pharmacophore Modeling and Molecular Docking Led to the Discovery of Inhibitors of Human Immunodeficiency Virus-1 Replication targeting the Human Cellular Aspartic Acid-Glutamic Acid-Alanine-Aspartic Acid Box Polypeptide 3," J. Med. Chem., 2008, vol. 51, pp. 6635-6638.
Maga et al. "Toward the Discovery of Novel Anti-HIV Drugs. Second-Generation Inhibitors of the Cellular ATPase DDX3 with Improved Anti-HIV Activity: Synthesis, Structure-Activity Relationship Analysis, Cytotoxicity Studies, and Target Validation," ChemMedChem., 2011, vol. 6, pp. 1371-1389.
Marintchev "Roles of Helicases in Translation Initiation: A Mechanistic View," Biochim Biophys Acta. Aug. 2013, vol. 1829, No. 8, pp. 799-809.
Newton et al. "Patenting combinatorial libraries and associated technologies: a review of the last 12 months," Expert Opinion on Therapeutic Patents, 1997, vol. 7, No. 10, pp. 1183-1194.
Oshiumi et al. "DEAD/H BOX 3 (DDX3) helicase binds the RIG-I adaptor IPS-1 to up-regulate IFN-β-inducing potential," Eur. J. Immunol., 2010, vol. 40, pp. 940-948.
Özes et al. "Duplex unwinding and ATPase activities of the DEAD-box helicase eIF4A are coupled by eIF4B," J Mol Biol, Sep. 2011, vol. 412, No. 4, pp. 674-687.
Parsyan et al. "The helicase protein DHX29 promotes translation initiation, cell proliferation, and tumorigenesis," PNAS, Dec. 2009, vol. 106, No. 52, pp. 22217-22222.
Parsyan et al. "MRNA helicases: the tacticians of translational control," Nature Reviews Molecular Cell Biology, Apr. 2011, vol. 12, pp. 235-245.
Pavia et al. "N-Phenyl-N'-pyridinylureas as Anticonvulsant Agents," J. Med. Chem. 1990, vol. 33, pp. 854-861.
Pek et al. "DEAD-box RNA helicase Belle/DDX3 and the RNA interference pathway promote mitotic chromosome segregation," PNAS, Jul. 2011, vol. 108, No. 29, pp. 12007-12012.
Perveen et al. Unsymmetrical 1,3-disubstituted urea derivatives as α-chymotrypsin inhibitors, Medicinal Chemistry Research, 2014, vol. 23, pp. 3585-3592.
Pestova et al. "Molecular mechanisms of translation initiation in eukaryotes," PNAS, Jun. 2001, vol. 98, No. 13, pp. 7029-7036.
Pestova et al. "The roles of individual eukaryotic translation initiation factors in ribosomal scanning and initiation codon selection," Genes & Development, 2002, vol. 16, pp. 2906-2922.
Plant et al. "The 9-Å Solution: How mRNA pseudoknots promote efficient programmed—1 ribosomal frameshifting," RNA, 2003, vol. 9, pp. 168-174.

(56) References Cited

OTHER PUBLICATIONS

Powell et al. "Characterization of the termination-reinitiation strategy employed in the expression of influenza B virus BM2 protein," RNA, 2008, vol. 14, pp. 2394-2406.

Powell et al. "Further Characterisation of the Translational Termination-Reinitiation Signal of the Influenza B Virus Segment 7 RNA," PLOS One, Feb. 2011, vol. 6, No. 2, e16822.

Price et al. "Use of Freely Available and Open Source Tools for in Silico Screening in Chemical Biology," Journal of Chemical Education, 2014, vol. 91, pp. 602-604.

Purohit et al. "Mutagenicity of Nitroaromatic Compounds," Chemical Research in Toxicology, Aug. 2000, vol. 13, No. 8, pp. 673-692.

Radi et al. "Discovery of the first small molecule inhibitor of human DDX3 specifically designed to target the RNA binding site: Towards the next generation HIV-1 inhibitors," Bioorganic & Medicinal Chemistry Letters, 2012, vol. 22, No. 5, pp. 2094-2098.

Richter et al. "Further Biochemical and Kinetic Characterization of Human Eukaryotic Initiation Factor 4H," The Journal of Biological Chemistry, Dec. 1999, vol. 274, No. 50, pp. 35415-35424.

Sah et al. "M-Bromobenzazide as a Reagent for the Identification of Amines," Recl. Trav. Chim. Pays-Bas., 1939, vol. 58, pp. 8-11.

Sah "P-Nitrobenzazide and p-Nitrophenyl Isocyanate as Reagents for the Identification of Amines," Recl. Trav. Chim. Pays-Bas., 1940, vol. 59, pp. 231-237.

Sah et al. "P-IODO Benzazide as a Reagent for the Identification of Amines," Recl. Trav. Chim. Pays-Bas., 1940, vol. 59, pp. 364-368.

Salomon-Ferrer et al. "Routine Microsecond Molecular Dynamics Simulations with AMBER on GPUs. 2. Explicit Solvent Particle Mesh Ewald," Journal of Chemical Theory and Computation, 2013, vol. 9, pp. 3878-3888.

Shih et al. "Critical roles of RNA helicase DDX3 and its interactions with eIF4E/PABP1 in stress granule assembly and stress response," Biochem. J., 2012, vol. 441, pp. 119-129.

Smith "Designing Drugs to Avoid Toxicity," Progress in Medicinal Chemistry, 2011, vol. 50, pp. 1-47.

Soto-Rifo et al. "DEAD-box protein DDX3 associates with eIF4F to promote translation of selected mRNAs," The EMBO Journal, 2012, vol. 31, pp. 3745-3756.

Soto-Rifo et al. "The role of the DEAD-box RNA helicase DDX3 in mRNA metabolism," WIREs RNA, Jul./Aug. 2013, vol. 4, pp. 369-385.

Soto-Rifo et al. "The DEAD-box helicase DDX3 substitutes for the cap-binding protein EIF4E to promote compartmentalized translation initiation of the HIV-1 genomic RNA," Nucleic Acids Research, 2013, vol. 41, No. 12, pp. 6286-6299.

Soulat et al. "The DEAD-box helicase DDX3X is a critical component of the TANK-binding Kinase 1-dependent innate immune response," The EMBO Journal, 2008, vol. 27, pp. 2135-2146.

Storey "Respiratory syncytial virus market," Nature Reviews Drug Discovery, Jan. 2010, vol. 9, pp. 15-16.

Svitkin et al. "The requirement for eukaryotic initiation factor 4A (eIF4A)in translation is in direct proportion to the degree of mRNA 5' secondary structure," RNA, 2001, vol. 7, No. 3, pp. 382-394.

Tijerina et al. "Nonspecific binding to structured RNA and preferential unwinding of an exposed helix by the CYT-19 protein, a DEAD-box RNA chaperone," PNAS, Nov. 2006, vol. 103, No. 45, pp. 16698-16703.

Urbahns et al. "Naphthol derivatives as TRPV1 inhibitors for the treatment of urinary incontinence," Bioorganic & Medicinal Chemistry Letters, 2011, vol. 21, pp. 3354-3357.

Vinogradova et al. "Palladium-Catalyzed Cross-Coupling of Aryl Chlorides and Triflates with Sodium Cyanate: A Practical Synthesis of Unsymmetrical Ureas," Journal of the American Chemical Society, 2012, vol. 134, pp. 11132-11135.

Wu et al. "Synthesis and Biological Evaluation of Non-Peptidic Cyclophilin Ligands," J. Med. Chem., 2003, vol. 46, No. 7, pp. 1112-1115.

Yang et al. "The DEAD-box protein Ded1 unwinds RNA duplexes by a mode distinct from translocating helicases," Nature Structural & Molecular Biology, Nov. 2006, vol. 13, No. 11, pp. 981-986.

Yang et al. "DEAD-Box Proteins Unwind Duplexes by Local Strand Separation," Molecular Cell, Oct. 2007, vol. 28, pp. 253-263.

Yedavalli et al. "Requirement of DDX3 DEAD Box RNA Helicase for HIV-1 Rev-RRE Export Function," Cell, Oct. 2004, vol. 119, pp. 381-392.

Zhang et al. "Evaluation of Diarylureas for Activity Against Plasmodium falciparum," ACS Medical Chemistry Letters, 2010, vol. 1, pp. 460-465.

Figure 16: sequence and coding capacity of the hRSV strain A2 M2 mRNA

*RSV strain A2 (subgroup A)*

Nucleotides 392 to 511 are underlined

```
GGGGCAAAUAUGUCACGAAGGAAUCCUUGCAAAUUUGAAAUUCGAGGUCAUUGCUUAAAU     60
          M  S  R  R  N  P  C  K  F  E  I  R  G  H  C  L  N

GGUAAGAGGUGUCAUUUUAGUCAUAAUUAUUUUGAAUGGCCACCCCAUGCACUGCUUGUA    120
 G  K  R  C  H  F  S  H  N  Y  F  E  W  P  P  H  A  L  L  V

AGACAAAACUUUAUGUUAAACAGAAUACUUAAGUCUAUGGAUAAAAGUAUAGAUACCUUA    180
 R  Q  N  F  M  L  N  R  I  L  K  S  M  D  K  S  I  D  T  L

UCAGAAAUAAGUGGAGCUGCAGAGUUGGACAGAACAGAAGAGUAUGCUCUUGGUGUAGUU    240
 S  E  I  S  G  A  A  E  L  D  R  T  E  E  Y  A  L  G  V  V

GGAGUGCUAGAGAGUUAUAUAGGAUCAAUAAACAAUAUAACUAAACAAUCAGCAUGUGUU    300
 G  V  L  E  S  Y  I  G  S  I  N  N  I  T  K  Q  S  A  C  V

GCCAUGAGCAAACUCCUCACUGAACUCAAUAGUGAUGAUAUCAAAAAGCUGAGGGACAAU    360
 A  M  S  K  L  L  T  E  L  N  S  D  D  I  K  K  L  R  D  N

GAAGAGCUAAAUUCACCCAAGAUAAGAGUGUACAAUACUGUCAUAUCAUAUAUUGAAAGC    420
 E  E  L  N  S  P  K  I  R  V  Y  N  T  V  I  S  Y  I  E  S

AACAGGAAAAACAAUAAACAAACUAUCCAUCUGUUAAAAAGAUUGCCAGCAGACGUAUUG    480
 N  R  K  N  N  K  Q  T  I  H  L  L  K  R  L  P  A  D  V  L

AAGAAAACCAUCAAAAACACAUUGGAUAUCCAUAAGAGCAUAACCAUCAACAACCCAAAA    540
 K  K  T  I  K  N  T  L  D  I  H  K  S  I  T  I  N  N  P  K

GAAUCAACUGUUAGUGAUACAAAUGACCAUGCCAAAAAUAAUGAUACUACCUGACAAAUA    600
 E  S  T  V  S  D  T  N  D  H  A  K  N  N  D  T  T
                            M  T  M  P  K  I  M  I  L  P  D  K  Y

UCCUUGUAGUAUAACUUCCAUACUAAUAACAAGUAGAUGUAGAGUUACUAUGUAUAAUCA    660
  P  C  S  I  T  S  I  L  I  T  S  R  C  R  V  T  M  Y  N  Q

AAAGAACACACUAUAUUUCAAUCAAAACAACCCAAAUAACCAUAUGUACUCACCGAAUCA    720
  K  N  T  L  Y  F  N  Q  N  N  P  N  N  H  M  Y  S  P  N  Q

AACAUUCAAUGAAAUCCAUUGGACCUCUCAAGAAUUGAUUGACACAAUUCAAAAUUUUCU    780
  T  F  N  E  I  H  W  T  S  Q  E  L  I  D  T  I  Q  N  F  L

ACAACAUCUAGGUAUUAUUGAGGAUAUAUAUACAAUAUAUAUAUUAGUGUCAUAACACUC    840
  Q  H  L  G  I  I  E  D  I  Y  T  I  Y  I  L  V  S

AAUUCUAACACUCACCACAUCGUUACAUUAUUAAUUCAAACAAUUCAAGUUGUGGGACAA    900

AAUGGAUCCCAUUAUUAAUGGAAAUUCUGCUAAUGUUUAUCUAACCGAUAGUUAUUUAAA    960

A    961
```

Figure 17: sequence alignment of RSV M2 mRNAs

Prepared using CLUSTAL W2. Asterisks indicate sequence identity hRSV A2: human respiratory syncytial virus strain A2. GenBank accession number RSH1CE
hRSV B1: human respiratory syncytial virus strain B1. GenBank accession number AF013254
BRSV: bovine respiratory syncytial virus strain A51908. GenBank accession number AF295543

ORSV: ovine respiratory syncytial virus. GenBank accession number ORU02510

```
hRSV A2    GGGGCAAAUAUGUCACGAAGGAAUCCUUGCAAAUUUGAAAUUCGAGGUCAUUGCUUAAAU 60
hRSV B1    GGGGCAAAUAUGUCGCGAAGAAAUCCUUGUAAAUUUGAGAUUAGAGGUCAUUGCUUGAAU 60
BRSV       GGGGCAAAUAUGUCACGAAGAAAUCCCUGCAAAUAUGAGAUUAGGGGACAUUGCUUAAAU 60
ORSV       GGGGCAAAUAUGUCACGAAGAAAUCCCUGCAAAUAUGAGAUCAGGGGACAUUGCUUAAAU 60
           **********    ** * **  *   **** * hRSV A2    GGUAAGAGGUGUCAUUUUUAGUCAUAAUUAUUUUGAAUGGCCACCCCAUGCACUGCUUGUA 120
hRSV B1    GGUAGAAGAUGUCACUACAGUCAUAAUUACUUUGAAUGGCCUCCUCAUGCCUUACUAGUG 120
BRSV       GGUAAAAAAUGUCAUUUUUAGUCAUAAUUACUUUGAAUGGCCUCCACAUGCUUUAUUAGUG 120
ORSV       GGCAAAAAAUGCCAUUUCAGCCAUAAUUACUUUGAAUGGCCUCCACAUGCUUUAUUAGUG 120
             *  *         *  *** *****    *****   *  ** hRSV A2    AGACAAAACUUUAUGUUAAACAGAAUACUUAAGUCUAUGGAUAAAAGUAUAGAUACCUUA 180
hRSV B1    AGGCAAAACUUCAUGUUAAACAAGAUACUCAAGUCAAUGGACAAAAGCAUAGACACUUUG 180
BRSV       AGGCAAAAUUUUAUGCUAAAUAAGAUAUUAAAAUCUAUGGACAGGAACAACGAUACCCUG 180
ORSV       AGGCAAAAUUUUAUGUUAAACAAGAUAUUAAAGUCUAUGGAUAGGAGCAAUGAUACUCUG 180
             *    ***  *      * ***    *     * hRSV A2    UCAGAAAUAAGUGGAGCUGCAGAGUUGGACAGAACAGAAGAGUAUGCUCUUGGUGUAGUU 240
hRSV B1    UCUGAAAUAAGUGGAGCUGCUGAACUGGACAGAACAGAAGAAUAUGCUCUUGGUAUAGUU 240
BRSV       UCAGAAAUAAGUGGUGCAGCGAGAGUUGGAUAGAACAGAAGAAUAUGCAUUGGGUGUAAUA 240
ORSV       UCAGAGAUAAGUGGAGCUGCAGAAUUAGAUAGAACAGAGGAAUAUGCAUUAGGUGUGAUA 240
              *    ** *     ****  **** *     * hRSV A2    GGAGUGCUAGAGAGUUAUAUAGGAUCAAUAAACAAUAUAACUAAACAAUCAGCAUGUGUU 300
hRSV B1    GGAGUGCUAGAGAGUUACAUAGGAUCUAUAAACAACAUAACAAAACAAUCAGCAUGUGUU 300
BRSV       GGAGUUUUGGAAAGUUACCUAGGCUCUAUCAAUAAUAUAACAAAACAAUCAGCCUGUGUU 300
ORSV       GGAGUUUUAGAAAGUUACUUGGGCUCUGUUAAUAACAUAACAAAACAAUCAGCUUGUGUU 300
           *****   *              * ****** **** hRSV A2    GCCAUGAGCAAACUCCUCACUGAACUCAAUAGUGAUGAUAUCAAAAAGCU-GAGGGACAA 359
hRSV B1    GCUAUGAGUAAACUUCUUAUUGAGAUCAAUAGUGAUGACAUUAAAAAGCU-GAGAGAUAA 359
BRSV       GCUAUGAGUAAACUAUUAGCCGAGAUUAACAAUGAUGACAU--AAAGAGAUUGAGGAACAA 359
ORSV       GCUAUGAGUAAAUUAUUAGGUGAGAUUAAUAGUGAUGACAU-CAAAGGAUUAAGAAACAA 359
            *  *    *        * ****    ** *     *    ** hRSV A2    UGAAGAGCUAAAUUCACCCAAGAUAAGAGUGUACAAUACUGUCAUAUCAUAUAUUGAAAG 419
hRSV B1    UGAAGAACCCAAUUCACCUAAGAUAAGAGUGUACAAUACUGUUAUAUCAUACAUUGAGAG 419
BRSV       GGAAGUGCCAACAUCACCUAAGAUAAGAAUAUAUAACACAGUUAUAUCAUAUAUUGAUAG 419
ORSV       AGAAUUGCCAACUUCACCUAAGAUAAGAAUAUAUAACACAGUUAUAUCAUAUAUUGAUAG 419
            ***    *  *  *** ****** * **  *   ******  ** * hRSV A2    CAACAGGAAAACAAUAAACAAACUAUCCAUCUGUUAAAAGAUUGCCAGCAGACGUAUU 479
hRSV B1    CAAUAGAAAAAACAACAAGCAAACAAUCCAUCUGCUCAAAAGACUACCAGCAGACGUGCU 479
BRSV       CAACAAGAGAAACACAAAACAAACUAUACAUUUGCUUAAGAGAUUGCCUGCAGACGUACU 479
```

Figure 17 CONTINUED : sequence alignment of RSV M2 mRNAs

```
ORSV       CAACAAGAGAAACCCAAAACAAACUAUACAUUACUUAAAAGAUUGCCUGCAGAUGUGCU  479
           ***  *  * **     ***    ***    *   *   *     * hRSV A2    GAAGAAAACCAUCAAAAACACAUUGGAUAUCCAUAAGAGCAUAACCAU--CAACAACCCAA  538
hRSV B1    GAAGAAGACAAUAAAAAACACAUUAGAUAUCCACAAAAGCAUAAUCAU--AAGCAACCCAA  538
BRSV       UAAAAGACAAUCAAGAACACUAUAGAUAUUCACAACGAAAUAAAUGGUAAUAA--CCAAG  538
ORSV       UAAGAAGACCAUCAAGAAUACAAUAGAUAUUCACAAUGAAAUAAAUGUUAAUAAUCCAAG  539
                       **    *  ***           **     *    *  **  * hRSV A2    AAGAAUCAACUGUUAGUGAUACAAAUGACCAUG-CCAAAAAUAAUGAUACUACCUGACAA  597
hRSV B1    AAGAGUCAACCGUGAAUGAUCAAAAUGACCAAA--CCAAAAAUAAUGAUAUUACCGGAUAA  597
BRSV       GUGACAUAAUUGUUAAUGAACAAAAUGAAUAACUCCAACAU-UAUUAUUUUCCCAGAAAA  597
ORSV       U--GACAUAGGUGUUAAUGAACAAAAUGAAUAAUUCCAAUAU-CAUUAUUUUCCCAGAGAA  597
                 **    *    ** * *  ****  *    ****  *         *   ** hRSV A2    AUAUCCUUGUAGUAUAACUUCCAUACUAAUAACAAGU----AGAUGUA--G---AGUUACUAUG  652
hRSV B1    AUAUCCUUGUAGUAUACAUCCAUAUUGAUUUCAAGU----GAAAGCAUG---AUU--GCUACA  652
BRSV       AUACCCUUGUAGCAUAUCCCUCUUUGCUAAGUUAAGAAU-GAAAAUGAUGUUAU--UGU--ACU  654
ORSV       AUAUCCUUGUAGUAUAUCUUCUUUGUUAAU---CAGAUGAUGAGAAUAAUGUUAU--UGU--AUU  654
           *  **** *  *  * **   * **                    *         *        *       * hRSV A2    UAUAAUCAAAAGAACAC------ACUAUAUUUCAAU---CAAAACAACCC-----AAAUAACCA  702
hRSV B1    UUCAAUCAUAAAAACAU------AUUA------CAAUUUAACCAUAACCAUUGGAUAACCA  702
BRSV       ---AAGUCAUCAAAAUGUUCUUGACUACU-UACAG---UUUCAAUAUCCAUGUAAU-AUGUA  708
ORSV       ---AAAUCAUCAGAAUAUUUUUGACUGCU-CACAG---UCUCAACAUCCAUGUGAU-AUGUA  708
                    *  ***   *  **        *  *                          *    *  **       *      * hRSV A2    UAUGUACUCACCG--------AAUCAAACAUUCAAUGAAAUCCAUUGGACCUCUCAAGAAU  755
hRSV B1    --------C--CAGCGUUUAUUAAUAAUAUAUUUGAUGAAAUUCAUUGGACACCUAAAAACU  755
BRSV       U-----UCUCAAAAU------------CAUAUGCUUGAUGAUAUCUAUUGGACAUCACAGGAGC  755
ORSV       U---------CCUCAAAAU---------------CAUAUACUUGACUAUACCUAUUGGACAUCACAGGAAU  755
                          *  ***                      *   *     *   *  *   * *******    *    * hRSV A2    UGAU----UGACACAAUUCAAAAUUUUCUACAACAU-CUAGGUAUUAUUG--AGGAUAUAUA  810
hRSV B1    -UAU---UAGAUGCCACUCAACAAUUUCUCCAACAU-CUUAACAUCCCUG--AAGAUAUAUA  810
BRSV       UAAUUGAGGAUGUACU-UAAGAUU----CUUCAUCUUUCU-GGCAUAUCCAUAAGU--AAGUA  810
ORSV       UGAUUGACAUGUACU-AAAGAUU----CUUCACCUUUCU-AGCAUCCCCAUAAAU--AGGUA  810
                              ** *   *         *  *  *                      *         * ** hRSV A2    UACAAUAUAUAUUAGUGU-------------------CAU--AACACUCAAUUCUAACACUCA  854
hRSV B1    UACAAUAUAUAUUAGUGU-----------------CAU--AAUGCUUGG------CCAU----  846
BRSV       UGUGAUAUAUGUUUUAGUGCUAUAGUAUAUAAGUCACUCAACUAUUAAU------CAACAG  865
ORSV       UGUGGUCUAUGUCUUAGUGCUGUAGUAUGUAAAUCAUUUAACUUUCAAU------CAUUAU  865
            *   *  ***  *  ****                                    **     *                  ** hRSV A2    CCACAUCGUUACAUUAUUAAUUCAAACAAUUCAAGUUGUGGGACAAAAUGGAUCCCAUUA  914
hRSV B1    -------------------------AACGAUUCUAU--------------AU-------CAU---------  862
BRSV       CCACU-----U-CUUCAU---AGCUAGCAAU---AUAU---AAGGACAAAAUGGAUACACUCA  913
ORSV       CUAUAUAUUU-CU--CCUUGUAGCCGGAAAU----ACACCAGAGGACAAAAUGGACUCACUCA  921
                                                              **                 *               * hRSV A2    UUAAUGGAAAUUCUGCUAAUGUUUAUCUAACCGAUAGUUAUUUAAAA  961
hRSV B1    ----------------------------CCAACCAU----------AAAA  874
BRSV       UUCAUGAGAACUCAACUAAUGUUUACUUAACAGAUAGUUAUUUAAAA  960
ORSV       UUCAUGAAAACUCAACCAAUGUAUACUUAACAGAUAGUUAUUU----  964
                                                         ***
```

Figure 18: Amino acid sequence of human ATP-dependent RNA helicase DDX3X isoform 1. GenBank accession number NP_001347.3

```
MSHVAVENALGLDQQFAGLDLNSSDNQSGGSTASKGRYIPPHLRNREATKGFYDKDSSGWSSSKDKDAYS
SFGSRSDSRGKSSFFSDRGSGSRGRFDDRGRSDYDGIGSRGDRSGFGKFERGGNSRWCDKSDEDDWSKPL
PPSERLEQELFSGGNTGINFEKYDDIPVEATGNNCPPHIESFSDVEMGEIIMGNIELTRYTRPTPVQKHA
IPIIKEKRDLMACAQTGSGKTAAFLLPILSQIYSDGPGEALRAMKENGRYGRRKQYPISLVLAPTRELAV
QIYEEARKFSYRSRVRPCVVYGGADIGQQIRDLERGCHLLVATPGRLVDMMERGKIGLDFCKYLVLDEAD
RMLDMGFEPQIRRIVEQDTMPPKGVRHTMMFSATFPKEIQMLARDFLDEYIFLAVGRVGSTSENITQKVV
WVEESDKRSFLLDLLNATGKDSLTLVFVETKKGADSLEDFLYHEGYACTSIHGDRSQRDREEALHQFRSG
KSPILVATAVAARGLDISNVKHVINFDLPSDIEEYVHRIGRTGRVGNLGLATSFFNERNINITKDLLDLL
VEAKQEVPSWLENMAYEHHYKGSSRGRSKSSRFSGGFGARDYRQSSGASSSFSSSRASSSRSGGGGHGS
SRGFGGGGYGGFYNSDYGGNYNSQGVDWWGN
```

Figure 19: Alignment of the amino acid sequences of mammalian ATP-dependent RNA helicase DDX3X

Prepared using CLUSTAL W2. Asterisks indicate sequence identity periods indicate sequence similarity Alignment of:
ATP-dependent RNA helicase DDX3X isoform 1 [Homo sapiens]. GenBank accession number NP_001347.3
ATP-dependent RNA helicase DDX3X isoform X2 [Bos taurus]. GenBank accession number XP_005228343.1
ATP-dependent RNA helicase DDX3X isoform 1 [Ovis aries]. GenBank accession number XP_004022060.1
ATP-dependent RNA helicase DDX3X-like isoform X2 [Capra hircus]. GenBank accession number XP_005700968.1
Ddx3x protein [Mus musculus]. GenBank accession number AAI50863.1

```
Homo sapiens      MSHVAVENALGLDQQFAGLDLNSSDNQSGGSTASKGRYIPPHLRNREATK
Mus musculus      MSHVAVENALGLDQQFAGLDLNSSDNQSGGSTASKGRYIPPHLRNREATK
Ovis aries        MSHVAVENALGLDQQFAGLDLNSSDNQSGGSTASKGRYIPPHLRNREATK
Bos taurus        MSHVAVENALGLDQQFAGLDLNSSDNQSGGSTASKGRYIPPHLRNREATK
Capra hircus      MSHVAVENALGLDQQFAGLDLNSSDNQSGGSTASKGRYIPPHLRNREATK
                  *************************************************

Homo sapiens      GFYDKDSSGWSSSKDKDAYSSFGSRSDSRGKSSFFSDRGSGSRGRFDDRG
Mus musculus      GFYDKDSSGWSSSKDKDAYSSFGSRGDSRGKSSFFGDRGSGSRGRFDDRG
Ovis aries        GFYDKDSSGWSSSKDKDAYSSFGSRSDSRGKSSFFSDRGSGSRGRFDDRG
Bos taurus        GFYDKDSSGWSSSKDKDAYSSFGSRSDSRGKSSFFSDRGSGSRGRFDDRG
Capra hircus      GFYDKDSSGWSSSKDKDAYSSFGSRSDSRGKSSFFSDRGSGSRGRFDDRG
                  ************************.********.***************

Homo sapiens      RSDYDGIGSRGDRSGFGKFERGGNSRWCDKSDEDDWSKPLPPSERLEQEL
Mus musculus      RGDYDGIGGRGDRSGFGKFERGGNSRWCDKSDEDDWSKPLPPSERLEQEL
Ovis aries        RGDYDGIGGRGDRGGFGKYERG-NSRWCDKSDEDDWSKPLPPSERLEQEL
Bos taurus        RGDYDGIGGRGDRGGFGKYERG-NSRWCDKSDEDDWSKPLPPSERLEQEL
Capra hircus      RGDYDGIGGRGDRGGFGKYERG-NSRWCDKSDEDDWSKPLPPSERLEQEL
                  *.******.****.****:*** **************************

Homo sapiens      FSGGNTGINFEKYDDIPVEATGNNCPPHIESFSDVEMGEIIMGNIELTRY
Mus musculus      FSGGNTGINFEKYDDIPVEATGNNCPPHIESFSDVEMGEIIMGNIELTRY
Ovis aries        FSGGNTGINFEKYDDIPVEATGNNCPPHIESFSDVEMGEIIMGNIELTRY
Bos taurus        FSGGNTGINFEKYDDIPVEATGNNCPPHIESFSDVEMGEIIMGNIELTRY
Capra hircus      FSGGNTGINFEKYDDIPVEATGNNCPPHIESFSDVEMGEIIMGNIELTRY
                  *************************************************

Homo sapiens      TRPTPVQKHAIPIIKEKRDLMACAQTGSGKTAAFLLPILSQIYSDGPGEA
Mus musculus      TRPTPVQKHAIPIIKEKRDLMACAQTGSGKTAAFLLPILSQIYADGPGEA
Ovis aries        TRPTPVQKHAIPIIKEKRDLMACAQTGSGKTAAFLLPILSQIYSDGPGEA
Bos taurus        TRPTPVQKHAIPIIKEKRDLMACAQTGSGKTAAFLLPILSQIYSDGPGEA
Capra hircus      TRPTPVQKHAIPIIKEKRDLMACAQTGSGKTAAFLLPILSQIYSDGPGEA
                  ******************************************:******

Homo sapiens      LRAMKENGRYGRRKQYPISLVLAPTRELAVQIYEEARKFSYRSRVRPCVV
Mus musculus      LRAMKENGRYGRRKQYPISLVLAPTRELAVQIYEEARKFSYRSRVRPCVV
Ovis aries        LRAMKENGRYGRRKQYPISLVLAPTRELAVQIYEEARKFSYRSRVRPCVV
```

Figure 19 CONTINUED : Alignment of the amino acid sequences of mammalian ATP-dependent RNA helicase DDX3X

```
Bos taurus      LRAMKENGRYGRRKQYPISLVLAPTRELAVQIYEEARKFSYRSRVRPCVV
Capra hircus    LRAMKENGRYGRRKQYPISLVLAPTRELAVQIYEEARKFSYRSRVRPCVV
                **************************************************

Homo sapiens    YGGADIGQQIRDLERGCHLLVATPGRLVDMMERGKIGLDFCKYLVLDEAD
Mus musculus    YGGAEIGQQIRDLERGCHLLVATPGRLVDMMERGKIGLDFCKYLVLDEAD
Ovis aries      YGGADIGQQIRDLERGCHLLVATPGRLVDMMERGKIGLDFCKYLVLDEAD
Bos taurus      YGGADIGQQIRDLERGCHLLVATPGRLVDMMERGKIGLDFCKYLVLDEAD
Capra hircus    YGGADIGQQIRDLERGCHLLVATPGRLVDMMERGKIGLDFCKYLVLDEAD
                ****:*********************************************

Homo sapiens    RMLDMGFEPQIRRIVEQDTMPPKGVRHTMMFSATFPKEIQMLARDFLDEY
Mus musculus    RMLDMGFEPQIRRIVEQDTMPPKGVRHTMMFSATFPKEIQMLARDFLDEY
Ovis aries      RMLDMGFEPQIRRIVEQDTMPPKGVRHTMMFSATFPKEIQMLARDFLDEY
Bos taurus      RMLDMGFEPQIRRIVEQDTMPPKGVRHTMMFSATFPKEIQMLARDFLDEY
Capra hircus    RMLDMGFEPQIRRIVEQDTMPPKGVRHTMMFSATFPKEIQMLARDFLDEY
                **************************************************

Homo sapiens    IFLAVGRVGSTSENITQKVVWVEESDKRSFLLDLLNATGKDSLTLVFVET
Mus musculus    IFLAVGRVGSTSENITQKVVWVEEIDKRSFLLDLLNATGKDSLTLVFVET
Ovis aries      IFLAVGRVGSTSENITQKVVWVEESDKRSFLLDLLNATGKDSLTLVFVET
Bos taurus      IFLAVGRVGSTSENITQKVVWVEESDKRSFLLDLLNATGKDSLTLVFVET
Capra hircus    IFLAVGRVGSTSENITQKVVWVEESDKRSFLLDLLNATGKDSLTLVFVET
                ************************ *************************

Homo sapiens    KKGADSLEDFLYHEGYACTSIHGDRSQRDREEALHQFRSGKSPILVATAV
Mus musculus    KKGADSLEDFLYHEGYACTSIHGDRSQRDREEALHQFRSGKSPILVATAV
Ovis aries      KKGADSLEDFLYHEGYACTSIHGDRSQRDREEALHQFRSGKSPILVATAV
Bos taurus      KKGADSLEDFLYHEGYACTSIHGDRSQRDREEALHQFRSGKSPILVATAV
Capra hircus    KKGADSLEDFLYHEGYACTSIHGDRSQRDREEALHQFRSGKSPILVATAV
                **************************************************

Homo sapiens    AARGLDISNVKHVINFDLPSDIEEYVHRIGRTGRVGNLGLATSFFNERNI
Mus musculus    AARGLDISNVKHVINFDLPSDIEEYVHRIGRTGRVGNLGLATSFFNERNI
Ovis aries      AARGLDISNVKHVINFDLPSDIEEYVHRIGRTGRVGNLGLATSFFNERNI
Bos taurus      AARGLDISNVKHVINFDLPSDIEEYVHRIGRTGRVGNLGLATSFFNERNI
Capra hircus    AARGLDISNVKHVINFDLPSDIEEYVHRIGRTGRVGNLGLATSFFNERNI
                **************************************************

Homo sapiens    NITKDLLDLLVEAKQEVPSWLENMAYEHHYKGSSRGRSKSSRFSGGFGAR
Mus musculus    NITKDLLDLLVEAKQEVPSWLENMAFEHHYKGSSRGRSK-SRFSGGFGAR
Ovis aries      NTTKDLLDLLVEAKQEVPSWLENMAYEHHYKGSSRGRSKSSRFSGGFGAR
Bos taurus      NITKDLLDLLVEAKQEVPSWLENMAYEHHYKGSSRGRSK-SRFSGGFGAR
Capra hircus    NTTKDLLDLLVEAKQEVPSWLENMAYEHHYKGSSRGRSK-SRFSGGFGAR
                *:********************** *************  **********

Homo sapiens    DYRQSSGASSSSFSSSRASSSRSGGGHGSSRGFGGGGYGGFYNSDGYGG
Mus musculus    DYRQSSGASSSSFSSSRASSSRSGGGHGSSRGFGGGGYGGFYNSDGYGG
Ovis aries      DYRQSSGGSSSSFSSSPASSSPSGGGHGSSRGFGGGGYGGFYNSDGYGG
Bos taurus      DYRQSSGGSSSSFSSSRASSSRSGGGHGSSRGFGGGGYGGFYNSDGYGG
Capra hircus    DYRQSSGGSSSSFSSSRASSSRSGGGHGSSRGFGGGGYGGFYNSDGYGG
                *******.********.*****.****************.*********

Homo sapiens    NYNSQGVDWWGN
Mus musculus    NYNSQGVDWWGN
Ovis aries      NYNSQGVDWWGN
Bos taurus      NYNSQGVDWWGN
Capra hircus    NYNSQGVDWWGN
                ************
```

USE OF DDX3X INHIBITORS FOR THE TREATMENT OF PNEUMOVIRUS INFECTIONS

CROSS REFERENCE TO RELATED APPLICATIONS

This application is a national stage application under 35 U.S.C. 371 and claims the benefit of PCT Application No. PCT/GB2015/050724 having an international filing date of 12 Mar. 2015, which designated the United States, which PCT application claimed the benefit of Great Britain Patent Application No. 1404372.3 filed 12 Mar. 2014, the disclosures of which are incorporated herein by reference.

REFERENCE TO SEQUENCE LISTING

This application contains a Sequence Listing submitted as an electronic text file named "pctgb2015050724-seql.txt", having a size in bytes of 43 kb, and created on Mar. 18, 2015. The information contained in this electronic file is hereby incorporated by reference in its entirety pursuant to 37 CFR §1.52(e)(5).

FIELD OF THE INVENTION

The present invention relates to pneumoviruses such as respiratory syncytial virus (RSV) and in particular to compounds useful in the treatment of pneumovirus infection, and assays to identify inhibitors of pneumovirus replication.

BACKGROUND TO THE INVENTION

Pneumoviruses, such as human respiratory syncytial virus (hRSV), are viruses that cause respiratory tract infections. Infection with hRSV is widespread. Although infection in adults is usually mild (or even asymptomatic), with any symptoms similar to those of the common cold, the virus can cause severe lower respiratory tract infections in young children or the elderly.

Pneumovirus infections are also commonplace in animals, particularly cows, sheep and goats, with bovine RSV (bRSV), ovine RSV and caprine RSV respectively. An additional pneumovirus, pneumonia virus of mice (PVM), has been shown to infect a wide range of species including rodents, dogs and humans. The pneumoviruses display structural and functional homology, and similar respiratory tract infections in animals.

The current treatment options for hRSV are limited. There is therefore a need for new treatments for hRSV infection and other pneumovirus infections.

DEAD box RNA helicases are a family of ATP-dependent RNA helicase enzymes. These enzymes have a conserved sequence Asp-Glu-Ala-Asp (DEAD). DDX3X is a DEAD box RNA helicase, encoded by the DDX3X gene. DDX3X and homologs thereof can be found in humans and other mammals, such as cows and sheep. DEAD box proteins are associated with many processes ranging from RNA synthesis, RNA degradation and translation initiation. A DDX3X homologue expressed from a gene on the Y chromosome shares 91% sequence identity.

It is known that infection with HIV-1 or HCV (hepatitis C virus) can lead to DDX3X expression being induced, and that certain cancer types are associated with overexpression of DDX3X. Thus, WO 2011/039735 describes the use of certain DDX3X inhibitors to suppress in vitro activity of DDX3X, suppress HIV-1 replication, and suppress proliferation of tumour cell lines. DDX3X does not apparently play a role in regulating HIV-1 transcription, but apparently acts as a nucleo-cytoplasmic shuttling protein for the export of HIV-1 transcripts. Similarly, DDX3X is known to interact with HCV core proteins, and alter their intracellular location. However, no link has previously been suggested between DDX3X and pneumovirus infection.

Pneumovirus replication requires translation of two open reading frames (ORF) from the M2 mRNA. ORF-2 overlaps with ORF-1. Host ribosomes access and translate the pneumovirus M2 ORF-2 by using one of two or three AUG codons located upstream of the ORF-1 termination codon. Expression from these initiation codons requires the prior termination of M2 ORF-1 translation. The hRSV M2-2 protein produced by coupled translation has been proposed to be involved in the switch between virus transcription and replication.

SUMMARY OF THE PRESENT INVENTION

The present inventors have identified that DDX3X binds to the hRSV M2 mRNA. The region to which DDX3X binds has a large degree of complex RNA secondary structure which is essential for coupled translation. Blocking binding of DDX3X to this region prevents initiation of hRSV M2-2 translation, thus preventing the switch between virus transcription and replication. The interaction between hRSV M2 mRNA and DDX3X provides a novel target to identify agents which can inhibit hRSV replication, and suggests the use of DDX3X inhibitors in the treatment of hRSV infection and other pneumovirus infections.

According to one aspect of the invention, there is provided a DDX3X inhibitor for use in the treatment of pneumovirus infection, such as for example RSV infection, in a mammal. According to a further aspect of the invention, there is provided a method of treating a pneumovirus infection, such as for example hRSV infection, in a subject, wherein the method comprises the administration to the said subject of an effective amount of a DDX3X inhibitor.

In some embodiments, the DDX3X inhibitor is a human DDX3X inhibitor, a bovine DDX3X inhibitor, an ovine DDX3X inhibitor, and/or a caprine DDX3X inhibitor.

In some embodiments, the DDX3X inhibitor is a compound of Formula (I):

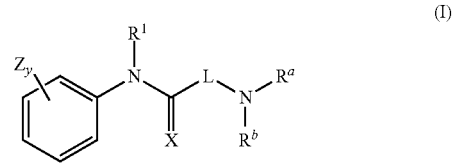

(I)

wherein y is 0, 1, or 2;

each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;

each X is independently O or S;

L is a bond or is selected from:

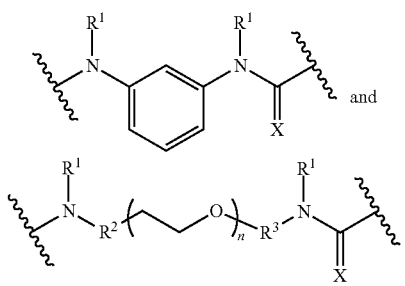

where n is 0, 1, 2, 3 or 4, and the wavy lines indicate the points of attachment to the rest of the molecule;
each $R^1$ is independently selected from H and substituted or unsubstituted $C_{1-3}$ alkyl;
each $R^2$ is a bond or is independently selected from substituted or unsubstituted $C_{1-3}$ alkyl;
each $R^3$ is selected from substituted or unsubstituted $C_{1-6}$ alkyl; and either:
  $R^a$ is selected from H and substituted or unsubstituted $C_{1-3}$ alkyl, and
  $R^b$ is selected from:
    substituted or unsubstituted $C_{1-10}$ alkyl, substituted or unsubstituted $C_{2-10}$ alkenyl, substituted or unsubstituted $C_{4-8}$ cycloalkyl, substituted or unsubstituted $C_{4-8}$ cycloalkenyl, and
    phenyl or 5-or 6-membered heteroaryl, each of which may be optionally substituted with up to 2 substituents Z,
or $R^a$ and $R^b$, together with the nitrogen atom to which they are attached, form a 5- or 6-membered substituted or unsubstituted heterocyclyl ring;
or a tautomer or a pharmaceutically acceptable salt thereof.
  In some further embodiments, each $R^1$ is H.
  In some further embodiments, y is 1.
  In some further embodiments, each Z is independently selected from methyl, acetyl, methoxy, methylthio, methylsulfoxide, methylsulfonyl, bromo, nitro, cyano, chloro and substituted $C_1$ alkyl. Preferably at least one Z is a meta or para substituent selected from methyl, methoxy, methylthio, cyano, nitro, bromo, chloro, and —$CF_3$. More preferably at least one Z is a meta or para substituent selected from methyl, methoxy, methylthio, cyano, chloro, and —$CF_3$.
  In some further embodiments, each Z is independently selected from methyl, acetyl, methoxy, methylthio, methylsulfoxide, methylsulfonyl, bromo, nitro, and cyano. Preferably at least one Z is a meta or para substituent selected from methyl, methoxy, methylthio, cyano, nitro and bromo.
  In some further embodiments, L is a bond or is selected from:

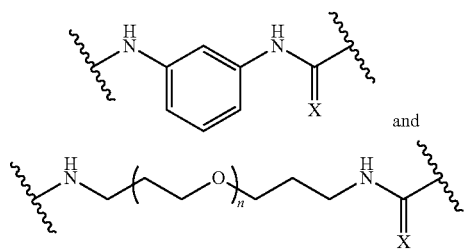

In some further embodiments, n is 3.
  In some further embodiments, $R^a$ is H.
  In some further embodiments, $R^b$ is selected from unsubstituted $C_{1-10}$ alkyl and unsubstituted $C_{4-8}$ cycloalkyl. Preferably, $R^b$ is selected from 2-methylcyclohexyl and n-octanyl.
  In some further embodiments, $R^b$ is phenyl or 5- or 6-membered heteroaryl, each of which may be optionally substituted with up to 2 substituents Z. Preferably, $R^b$ is selected from phenyl, pyridinyl, and pyrimidinyl, each of which is substituted with one substituent Z.
  In some further embodiments, y is 1;
  each Z is independently selected from methyl, acetyl, methoxy, methylthio, methylsulfoxide, methylsulfonyl, bromo, nitro, cyano, chloro and substituted $C_1$ alkyl;
  each X is independently O or S;
  L is a bond or is selected from:

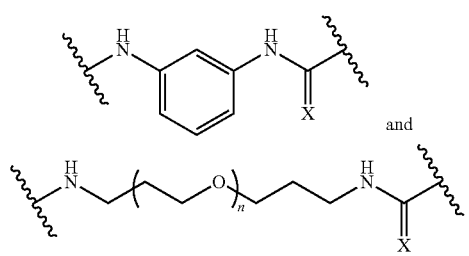

where n is 3, and the wavy lines indicate the points of attachment to the rest of the molecule;
$R^a$ is H; and
$R^b$ is selected from:
  2-methylcyclohexyl, n-octanyl,
  phenyl substituted one substituent Z,
  pyridinyl, and
  pyrimidinyl.
  In some further embodiments, y is 1;
each Z is independently selected from methyl, acetyl, methoxy, methylthio, methylsulfoxide, methylsulfonyl, bromo, nitro, and cyano;
each X is independently O or S;
L is a bond or is selected from:

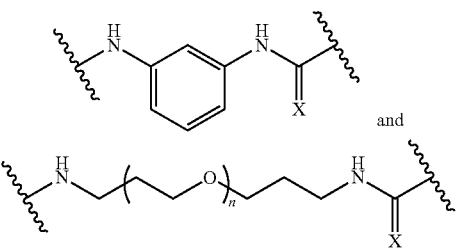

where n is 3, and the wavy lines indicate the points of attachment to the rest of the molecule;
$R^a$ is H; and
$R^b$ is selected from:
  2-methylcyclohexyl, n-octanyl,
  phenyl substituted one substituent Z,
  pyridinyl, and
  pyrimidinyl.
  In some further embodiments, the DDX3X inhibitor is a compound of Formula (II):

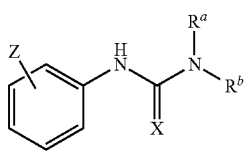

(II)

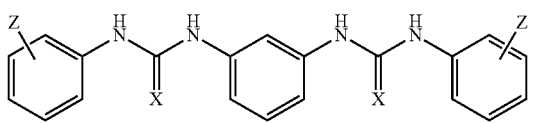

(III)

or a tautomer or a pharmaceutically acceptable salt thereof.

Preferably, $R^a$ is H and $R^b$ is selected from 2-methylcyclohexyl and n-octanyl.

Preferably, $R^a$ is H, $R^b$ is selected from:
phenyl substituted with 1 substituent Z,
pyridinyl and
pyrimidinyl;
and at least one Z is a meta or para substituent selected from methoxy, methylthio, cyano, nitro, bromo, chloro and —CF$_3$.

In some further embodiments, the DDX3X inhibitor is a compound of Formula (II):

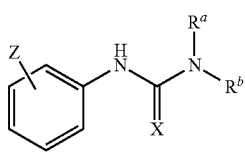

(II)

or a tautomer or a pharmaceutically acceptable salt thereof.

Preferably, $R^a$ is H and $R^b$ is selected from 2-methylcyclohexyl and n-octanyl.

Preferably, $R^a$ is H, $R^b$ is selected from:
phenyl substituted with 1 substituent Z,
pyridinyl and
pyrimidinyl;
and at least one Z is a meta or para substituent selected from methoxy, methylthio, cyano, nitro and bromo.

In some further embodiments, the DDX3X inhibitor is a compound of Formula (III):

wherein each Z is a meta or para substituent independently selected from methoxy, methylthio, cyano and nitro;
or a tautomer or pharmaceutically acceptable salt thereof.

Preferably, each Z is the same substituent, and both Z are meta substituents or both Z are para substituents.

In some further embodiments, the DDX3X inhibitor is a compound of Formula (III) where one Z is an ortho methyl substituent, and the other Z is a meta or para substituent selected from methoxy, methylthio, cyano and nitro;
or a tautomer or pharmaceutically acceptable salt thereof.

In some further embodiments, the DDX3X inhibitor is a compound of Formula (IV):

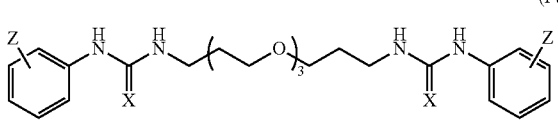

(IV)

wherein each Z is independently selected from methyl, methylthio and nitro;
or a tautomer or pharmaceutically acceptable salt thereof.

Preferably, each Z is the same substituent, and both Z are ortho substituents, both Z are meta substituents or both Z are para substituents.

Preferably, one Z is an ortho methyl substituent, and the other Z is a meta or para substituent selected from methylthio and nitro.

In some embodiments, the DDX3X inhibitor is selected from the group consisting of the compounds:

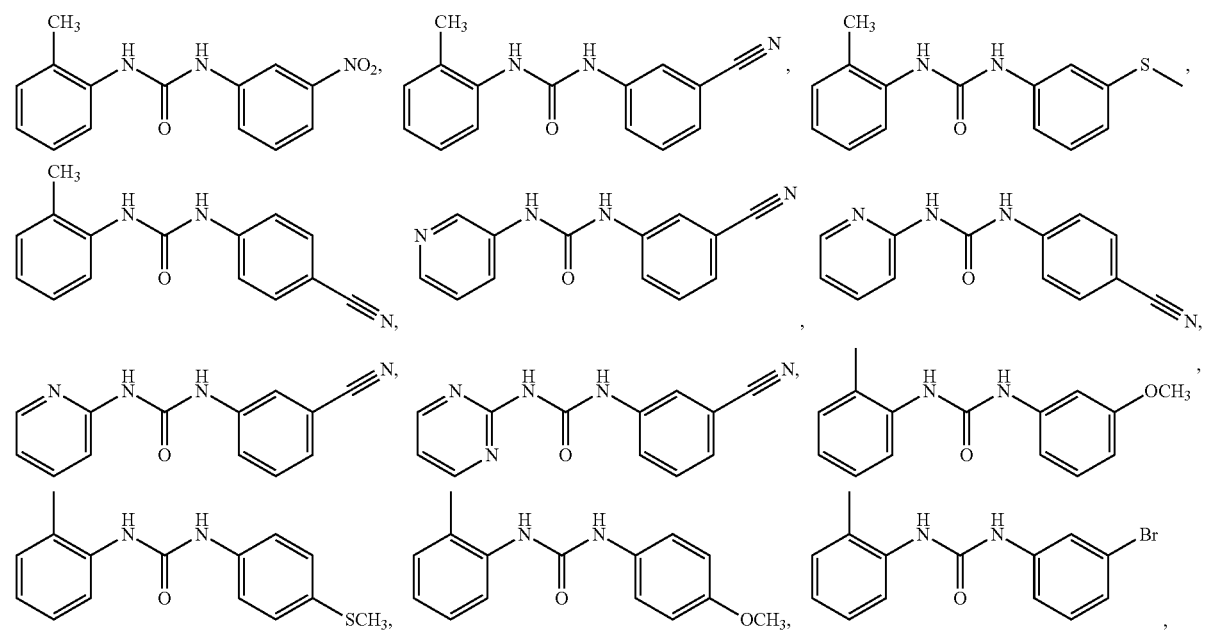

-continued
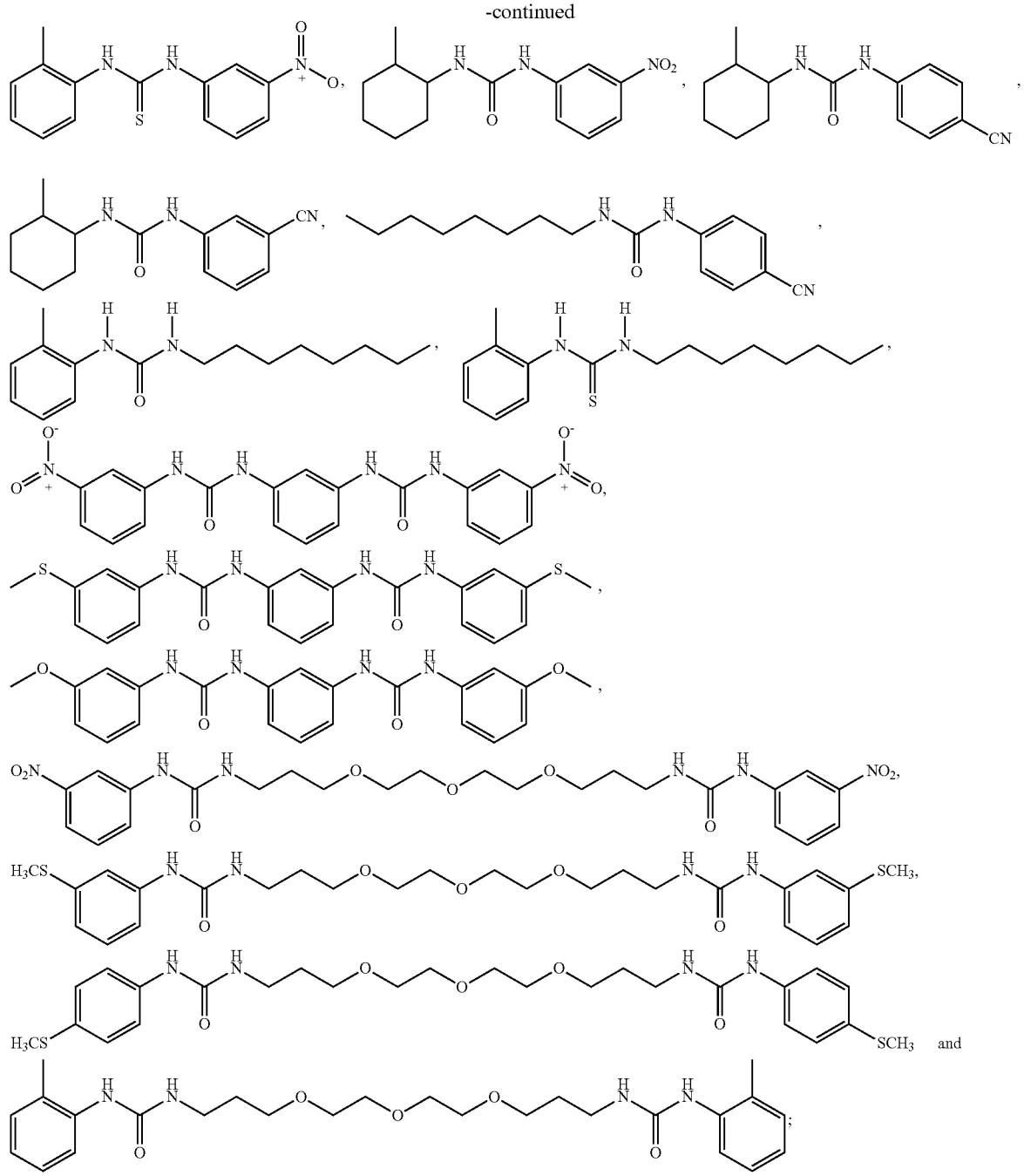
and tautomers and pharmaceutically acceptable salts thereof.
In other embodiments the DDX3X inhibitor is selected from the group consisting of the compounds shown in the preceding paragraph and tautomers and pharmaceutically acceptable salts thereof and the following compounds:
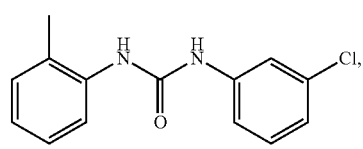 [SMILES: Cc1ccccc1NC(=O)Nc1cccc(Cl)c1]
-continued
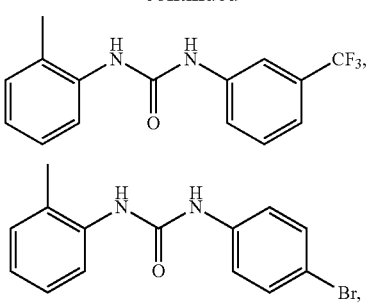

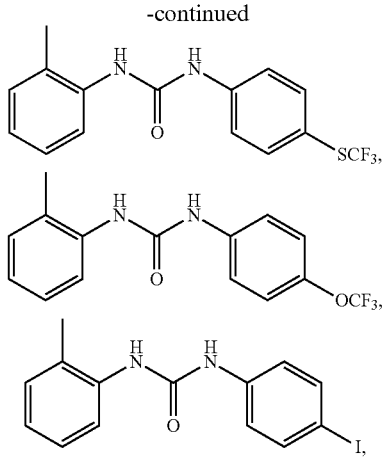
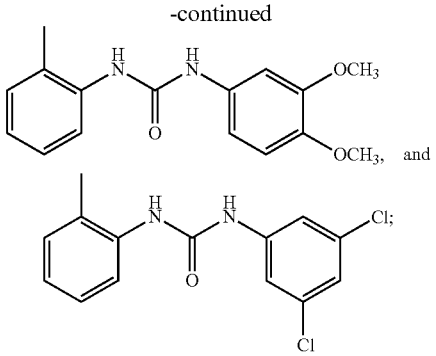
and tautomers and pharmaceutically acceptable salts thereof.
More preferably, the DDX3X inhibitor is selected from the group consisting of the compounds:
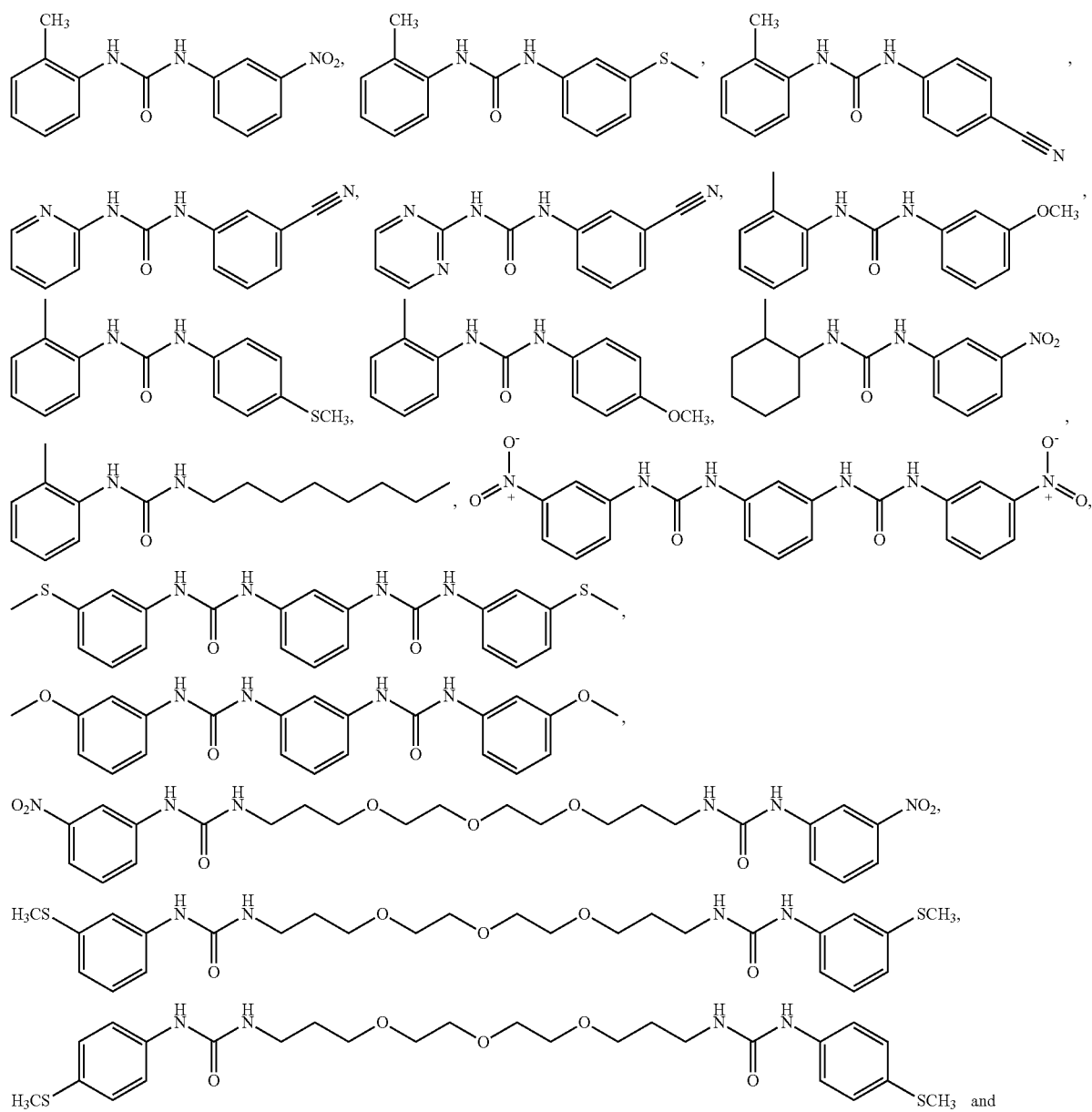

-continued

[chemical structure: bis-tolyl urea linked by propyl-O-ethyl-O-ethyl-O-propyl chain]

and tautomers and pharmaceutically acceptable salts thereof.

Alternatively the DDX3X inhibitor is selected from the group consisting of the compounds shown in the preceding paragraph and tautomers and pharmaceutically acceptable salts thereof and the following compounds:

[chemical structure: 1-(2-methylphenyl)-3-(3-chlorophenyl)urea], and

[chemical structure: 1-(2-methylphenyl)-3-(3-trifluoromethylphenyl)urea]

and tautomers and pharmaceutically acceptable salts thereof.

Most preferably, the DDX3X inhibitor is selected from the group consisting of the compounds:

[chemical structure: 1-(2-methylphenyl)-3-(3-methylthiophenyl)urea],

[chemical structure: 1-(2-methylphenyl)-3-(4-cyanophenyl)urea], and

[chemical structure: 1-(2-methylphenyl)-3-(4-methylthiophenyl)urea];

and tautomers and pharmaceutically acceptable salts thereof.

Alternatively the DDX3X inhibitor is selected from the group consisting of the compounds shown in the preceding paragraph and tautomers and pharmaceutically acceptable salts thereof and the following compound:

[chemical structure: 1-(2-methylphenyl)-3-(3-chlorophenyl)urea]

and tautomers and pharmaceutically acceptable salts thereof.

In some embodiments, the mammal is selected from humans, cattle, sheep and goats.

According to a further aspect of the invention, there is provided a compound of Formula (I):

$$\text{(I)}$$

[chemical structure of Formula (I) with substituents $Z_y$, $R^1$, L, $R^a$, $R^b$, X]

wherein y, Z, X, L, n, $R^1$, $R^2$, $R^3$, $R^a$ and $R^b$ are as defined above, or a tautomer or a pharmaceutically acceptable salt thereof, provided that the compound is other than:

[chemical structure: 1-(2-methylphenyl)-3-(3-nitrophenyl)urea]

In some embodiments, the compound is selected from the group consisting of the compounds:

[chemical structure: 1-(2-methylphenyl)-3-(3-cyanophenyl)urea],

[chemical structure: 1-(2-methylphenyl)-3-(3-methylthiophenyl)urea],

[chemical structure: 1-(2-methylphenyl)-3-(4-cyanophenyl)urea],

[chemical structure: 1-(pyridin-3-yl)-3-(3-cyanophenyl)urea],

[chemical structure: 1-(pyridin-2-yl)-3-(4-cyanophenyl)urea],

[chemical structure: 1-(pyridin-2-yl)-3-(3-cyanophenyl)urea],

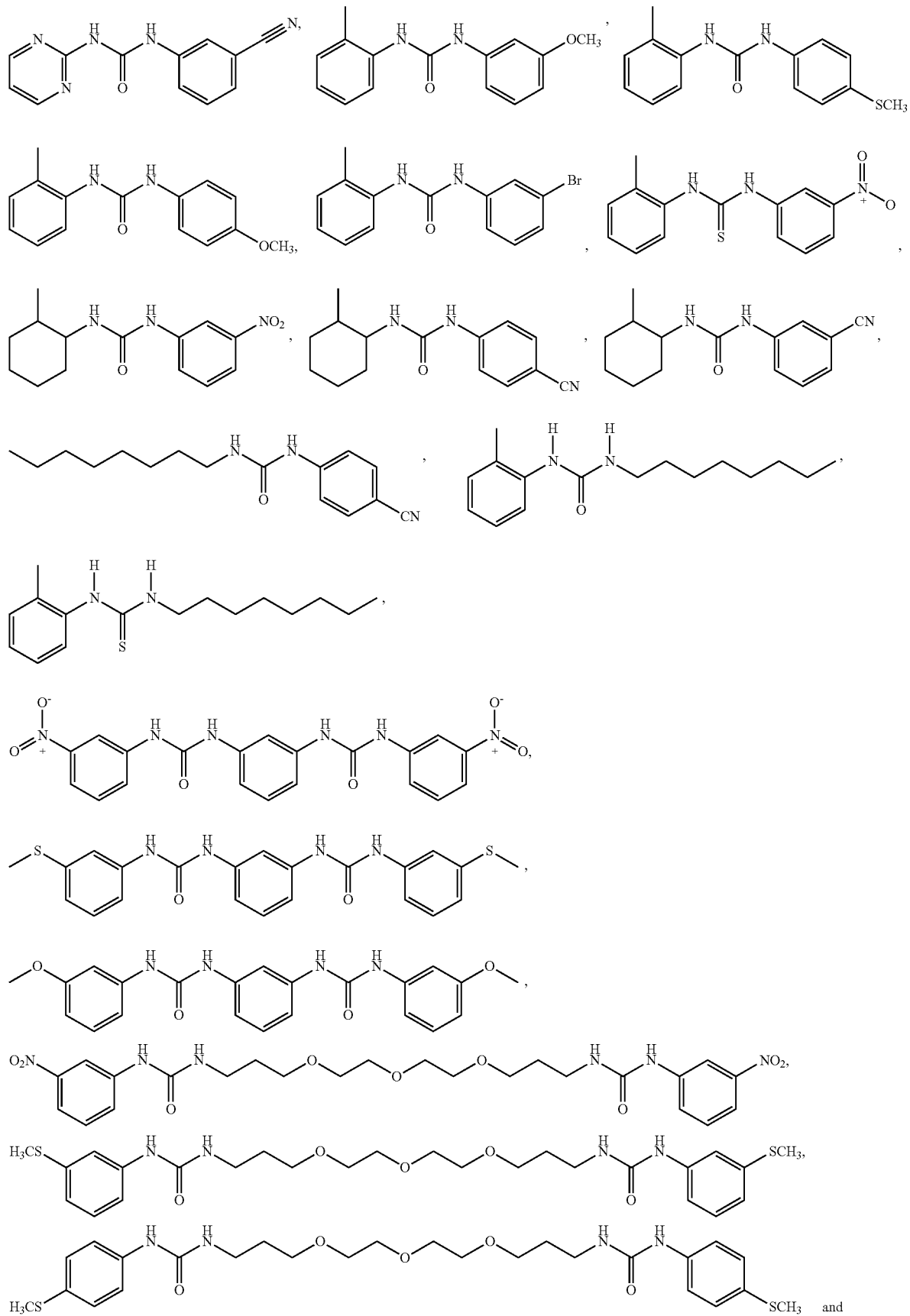

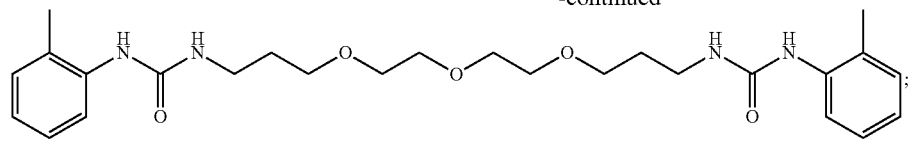

and tautomers and pharmaceutically acceptable salts thereof.

In other embodiments, the compound is selected from the group consisting of the compounds shown in the preceding paragraph and tautomers and pharmaceutically acceptable salts thereof and the following compounds:

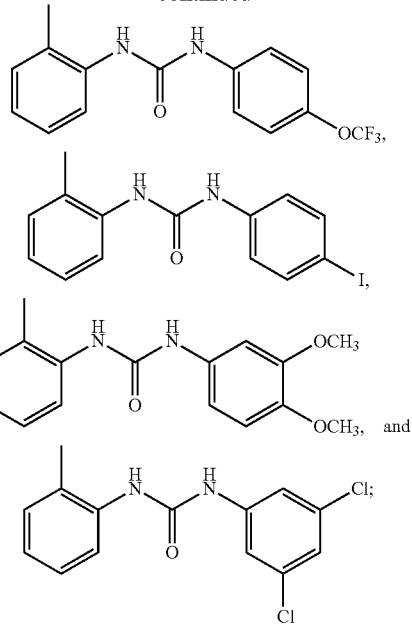

and tautomers and pharmaceutically acceptable salts thereof.

Preferably, the compound is selected from the group consisting of the compounds:

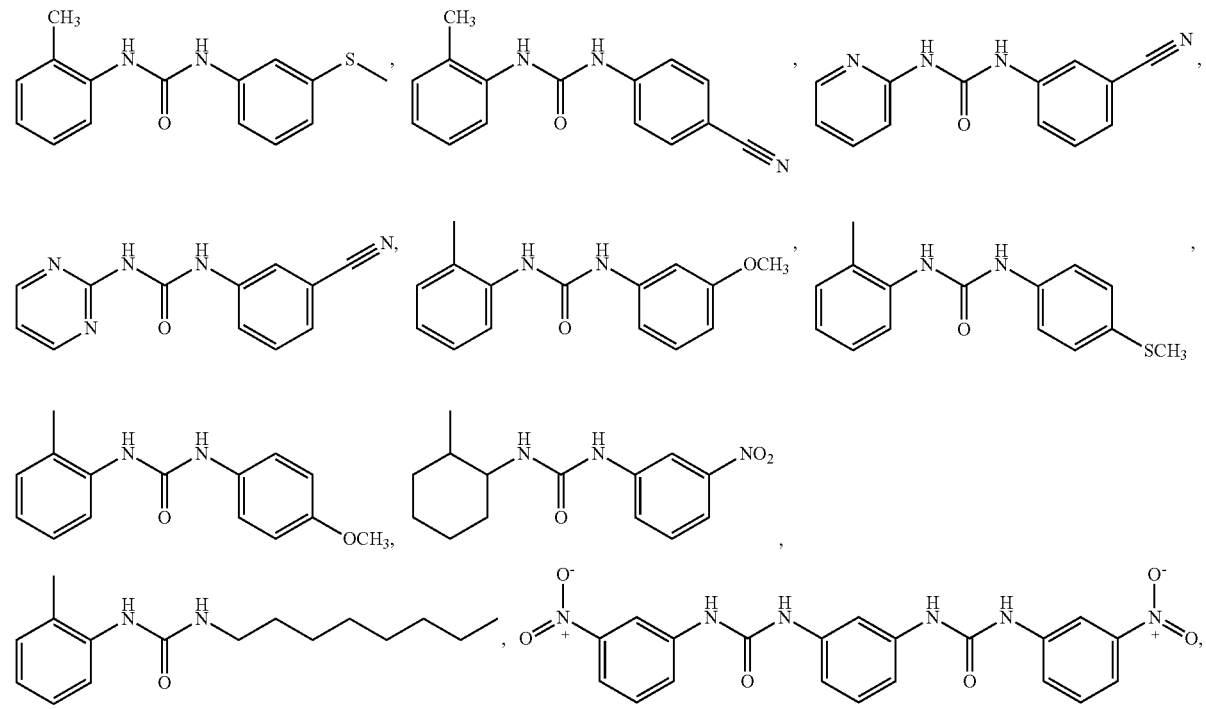

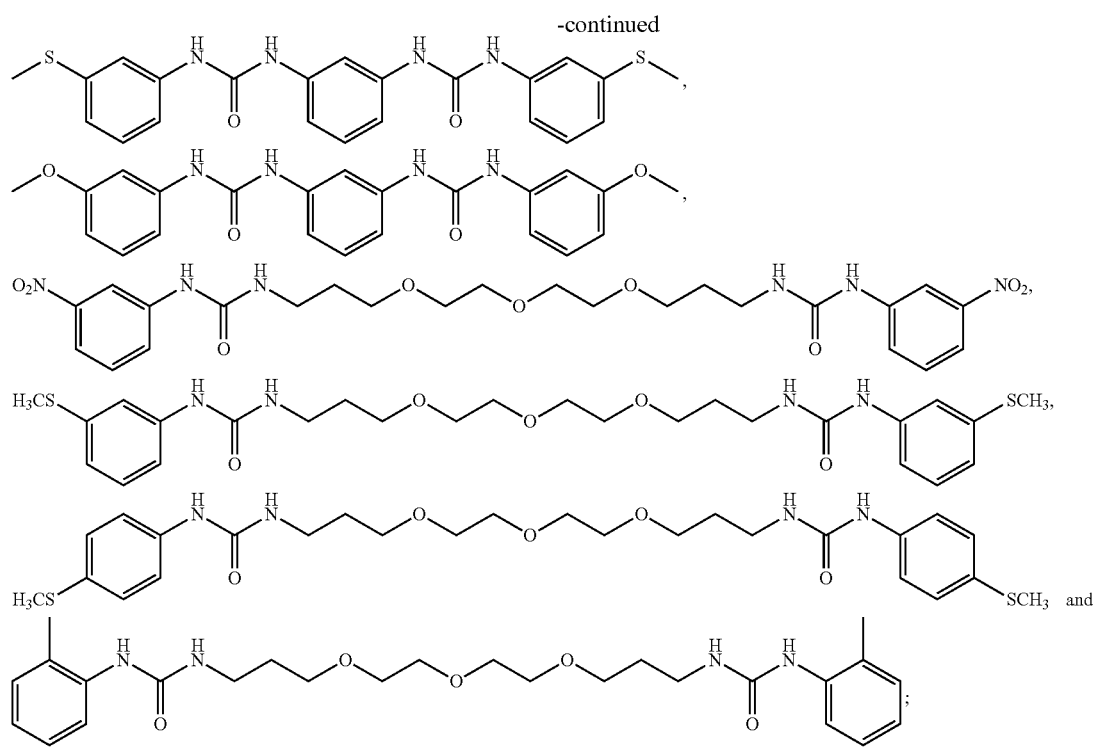

and tautomers and pharmaceutically acceptable salts thereof.

Alternatively, the compound is selected from the group consisting of the compounds shown in the preceding paragraph and tautomers and pharmaceutically acceptable salts thereof and the following compounds:

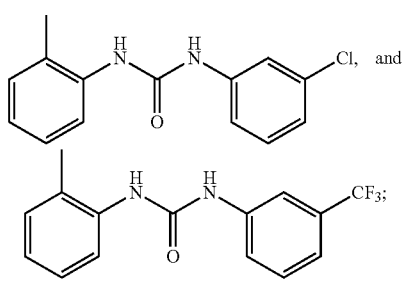

and tautomers and pharmaceutically acceptable salts thereof.

More preferably, the compound is selected from the group consisting of the compounds:

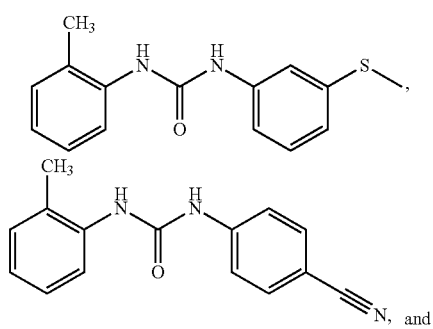

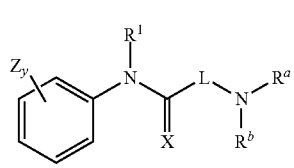

and tautomers and pharmaceutically acceptable salts thereof.

Alternatively, the compound is selected from the group consisting of the compounds shown in the preceding paragraph and tautomers and pharmaceutically acceptable salts thereof and the following compound:

and tautomers and pharmaceutically acceptable salts thereof.

According to a further aspect of the invention, there is provided a compound of Formula (I):

$$Z_y \text{—} \underset{\underset{R^1}{|}}{N} \text{—} \underset{\underset{X}{||}}{C} \text{—} L \text{—} \underset{\underset{R^b}{|}}{N} \text{—} R^a$$

(I)

wherein L is selected from

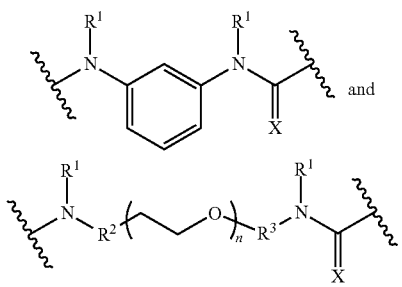

and y, Z, X, n, $R^1$, $R^2$, $R^3$, $R^a$ and $R^b$ are as defined above, or a tautomer or a pharmaceutically acceptable salt thereof.

According to a further aspect of the invention, there is provided a compound of Formula (I):

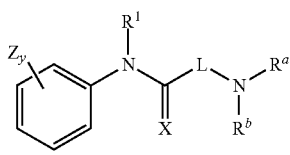

wherein X is S, and
y, Z, L, n, $R^1$, $R^2$, $R^3$, $R^a$ and $R^b$ are as defined above, or a tautomer or a pharmaceutically acceptable salt thereof.

According to a further aspect of the invention, there is provided a pharmaceutical composition comprising a compound as described above and a pharmaceutically-acceptable excipient.

According to a further aspect of the invention, there is provided a compound as described above for use in the treatment of the human or animal body.

BRIEF DESCRIPTION OF THE FIGURES

FIG. 16 shows sequence (SEQ ID NO. 1) and coding capacity (SEQ ID NOs. 2 and 3) of the hRSV strain A2 M2 mRNA RSV strain A2 (subgroup A).

FIG. 17 shows sequence alignment of RSV M2 mRNAs (SEQ ID NOs. 4 to 7).

FIG. 18 shows amino acid sequence of human ATP-dependent RNA helicase DDX3X isoform 1. GenBank accession number NP_001347.3. (SEQ ID NO. 8).

FIG. 19 shows alignment of the amino acid sequences of mammalian ATP-dependent RNA helicase DDX3X (SEQ ID NOs. 9 to 13).

DESCRIPTION OF THE SEQUENCE LISTING

Figure 1:
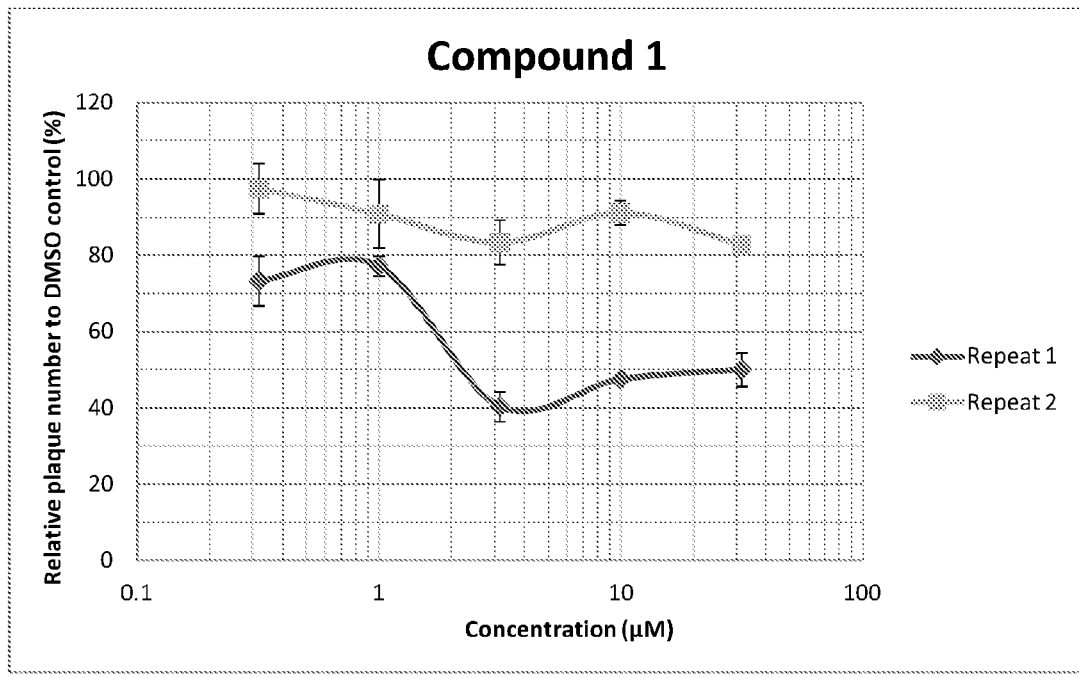
FIG. 1 shows two biological replicates carried out on different occasions for compound 1.

SEQ ID NO. 1 shows sequence of the hRSV strain A2 M2 mRNA RSV strain A2 (subgroup A).
SEQ ID NOs. 2 and 3 show coding capacity of the hRSV strain A2 M2 mRNA RSV strain A2 (subgroup A).
SEQ ID NO. 4 shows sequence of human respiratory syncytial virus strain A2.
SEQ ID NO. 5 shows sequence of human respiratory syncytial virus strain B 1.
SEQ ID NO. 6 shows sequence of bovine respiratory syncytial virus strain A51908.
SEQ ID NO. 7 shows sequence of ovine respiratory syncytial virus.
SEQ ID NO. 8 shows amino acid sequence of human ATP-dependent RNA helicase DDX3X isoform 1.
SEQ ID NO. 9 shows sequence of ATP-dependent RNA helicase DDX3X isoform 1 [Homo sapiens].
SEQ ID NO. 10 shows sequence of Ddx3x protein [Mus musculus].
SEQ ID NO. 11 shows sequence of ATP-dependent RNA helicase DDX3X isoform 1 [Ovis aries].
SEQ ID NO. 12 shows sequence of ATP-dependent RNA helicase DDX3X isoform X2 [Bos taurus].
SEQ ID NO. 13 shows sequence of ATP-dependent RNA helicase DDX3X-like isoform X2 [Capra hircus].

DETAILED DESCRIPTION

The present invention enables the treatment of pneumovirus (such as hRSV) infection, involving the use of a DDX3X inhibitor. The invention further provides a number of compounds which are of interest for use as DDX3X inhibitors.

As used herein, the term "alkyl" refers to hydrocarbons, particularly saturated hydrocarbons, having the specified number of carbon atoms, and includes straight-chain and branched-chain groups and combinations thereof.

As used herein, the term "acyl" refers to hydrocarbons having the specified number of carbon atoms and including at least one carbonyl moiety, and includes straight-chain and branched-chain groups and combinations thereof. The carbonyl may be located at any position in the group, but is typically located adjacent to a point of attachment to the remainder of the molecule.

As used herein, the term "alkoxy" refers to hydrocarbons having the specified number of carbon atoms and including one or more oxygen atoms linked by single bonds to carbon, and includes straight-chain and branched-chain groups and combinations thereof. The oxygen atoms may be located at any position in the group, but one oxygen atom is typically located adjacent to a point of attachment to the remainder of the molecule.

As used herein, the term "alkylthio" refers to hydrocarbons having the specified number of carbon atoms and including one or more sulfur atoms linked by single bonds to carbon, and includes straight-chain and branched-chain groups and combinations thereof. The sulfur atoms may be located at any position in the group, but one sulfur atom is typically located adjacent to a point of attachment to the remainder of the molecule.

As used herein, the term "alkylsulfoxide" refers to hydrocarbons having the specified number of carbon atoms and including at least one sulfinyl moiety, and includes straight-chain and branched-chain groups and combinations thereof. The sulfinyl moiety may be located at any position in the group, but is typically located adjacent to a point of attachment to the remainder of the molecule.

As used herein, the term "alkylsulfonyl" refers to hydrocarbons having the specified number of carbon atoms and including at least one sulfonyl moiety, and includes straight-chain and branched-chain groups and combinations thereof. The sulfonyl moiety may be located at any position in the group, but is typically located adjacent to a point of attachment to the remainder of the molecule.

As used herein, the term "halo" refers to an element found in Group 13 of the periodic table. Typical examples of halo substituents include fluoro, chloro and bromo.

Another typical example is iodo.

As used herein, the term "cycloalkyl" refers to hydrocarbons having the specified number of carbon atoms and including at least one cyclic structure, and includes straight-chain and branched-chain groups, and combinations thereof.

As used herein, the term "alkenyl" refers to hydrocarbons having the specified number of carbon atoms, and including at least one carbon-carbon double bond, and includes straight-chain and branched-chain groups, and combinations thereof.

As used herein, the term "cycloalkenyl" refers to hydrocarbons having the specified number of carbon atoms, and including at least one carbon-carbon double bond and at least one cyclic structure. The double bond may be incorporated wholly or partially within the cyclic structure or may be distinct from the cyclic structure. The term includes straight-chain and branched-chain groups, and combinations thereof.

As used herein, the term "substituted" refers to a moiety in which one or more hydrogen atoms, typically 1, 2 or 3 hydrogen atoms, has each been replaced by a substituent independently selected from hydroxyl, methoxy, thio, methylthio, amino, methylamino, dimethylamino, fluoro, chloro, bromo, iodo, cyano, nitro, sulfonate (or sulfonic acid), sulfonamide, carboxylate (or carboxylic acid) and carbonamide.

The present invention also relates to a method of identifying an agent which modulates hRSV replication comprising contacting an agent with (a) an RNA construct comprising the sequence of nucleotides 392 to 511 of the hRSV M2 transcript and (b) a protein comprising DDX3X, and determining whether the agent modulates the interaction between the construct and DDX3X.

The M2 mRNAs of pneumoviruses contain two open reading frames, referred to herein as M2-1 and M2-2. The region of nucleotides 392-511 of the hRSV M2 mRNA has strong secondary structure. The present inventors show that DDX3X interacts with this structure, to allow initiation of translation from the second ORF. The M2-2 protein translated from the M2 mRNA ORF-2 is required for the switch from transcription of the viral genome to replication, leading to virus particle assembly and release. Thus agents which interfere with this interaction are identified as useful in the treatment of infection by hRSV and other pneumoviruses.

The RNA constructs of the present invention comprise nucleotides 392 to 511 of the human M2 transcript, or an equivalent region in other pneumoviruses, including but not limited to bovine RSV, ovine RSV, caprine RSV. The sequence of the human ORF-1 region of the hRSV (strain A2) M2 transcript is shown in FIG. 16 (SEQ ID NOs. 1-3). M2 transcripts from other pneumoviruses show a high degree of homology in this region seen in FIG. 17 (SEQ ID NOs. 4-7). The construct may include additional sequences, for example flanking sequences from the hRSV M2 transcript. Assay methods which monitor for translation of the M2-2 ORF will include this ORF. Alternatively the construct may be provided with a reporter gene provided in frame with one of the AUG codons of the second ORF.

DDX3X is a DEAD box RNA helicase. The sequence of human DDX3X is provided in FIG. 18 (SEQ ID NO. 8). DDX3X is highly conserved across mammalian species as shown in FIG. 19 (SEQ ID NOs. 9-13). In view of the high degree of homology between pneumoviral M2 transcripts and DDX3X across species, the methods of the present invention can use pneumovirus constructs and DDX3X derived from other species, and can also be used to identify modulators which can be used to interfere with pneumovirus infection in a variety of mammalian species.

The compounds tested may be enhancers or inhibitors of the interaction between the construct and DDX3X, and thus act to enhance or inhibit pneumovirus replication, although preferably the method is used to identify an inhibitor of RSV replication. An inhibitor of pneumovirus replication interferes with the interaction between the construct and DDX3X.

Any compound(s) can be used in the method of the invention. The compound(s) may be any chemical compound(s) used in drug screening programmes. They may be natural or synthetic. Extracts of plants which contain several characterised or uncharacterised components may also be used. Typically, organic molecules will be screened, preferably small organic molecules which have a molecular weight of from 50 to 2500 Daltons. Compounds can be biomolecules including peptide and peptide mimetics, oligonucleotides, saccharides, fatty acids, steroids, purines, pyrimidines, derivatives, structural analogs or combinations thereof. Candidate compounds may be obtained from a wide variety of sources including libraries of synthetic or natural substances. Known pharmacological agents may be subjected to directed or random chemical modifications, such as acylation, alkylation, esterification, amidification, etc. to produce structural analogs. The compound(s) may be the product(s) of a combinatorial library such as are now well known in the art (see e.g. Newton (1997) Expert Opinion Therapeutic Patents, 7(10): 1183-1194). Natural product libraries, such as display (e.g. phage display libraries), may also be used.

The methods of the invention allow the screening of one or more compounds for their ability to act as modulator of pneumovirus replication. The methods are preferably carried out in vitro or ex vivo.

Techniques for determining the effect of compound(s) on the interaction between the RNA construct and DDX3X protein are within the skill of those in the art. Any of those techniques may be used in accordance with the invention. The method may be carried out in vitro, such as in a cell-free system or alternatively in a cell-based system.

In accordance with the methods of the present invention, the activity of an agent may be determined by investigating directly the effect on the binding interaction between DDX3X and the RNA construct. Alternatively, the methods may be conducted to determine translation from the second open reading frame (ORF-2) of M2. Reporter systems may also be used, for example to provide a construct which comprises a reporter gene cloned in frame from the start codon of ORF-2. Expression of the reporter gene will only occur when DDX3X is able to interact with the construct. The agents which interfere with the interaction will prevent translation of the reporter gene.

Preferred in vitro translation systems utilise cell extracts which provide components necessary for the process of translation. These typically include macromolecular components such as ribosomes, tRNAs, aminoacyl tRNA synthetases, initiation, elongation and termination factors. The cell extracts may be of any origin provided they allow for translation of the reporter coding sequence. Suitable cell extracts may be obtained from reticulocytes, such as rabbit reticulocytes, wheat germ and bacterial extracts, such as *E. coli* extracts. The cell extracts are suitably supplemented with additional components required for translation, such as amino acids, nucleotide triphosphate energy sources and other co-factors. The skilled person is familiar with the use of such systems.

In preferred embodiments, the RNA is added to the in vitro translation system directly in RNA form. Alternatively, a coupled or linked transcription/translation system may be utilised in which a DNA construct encoding the RNA is first transcribed prior to translation of the resulting RNA.

Techniques for measuring translation of a reporter coding sequence are well known in the art. Any suitable technique may be used. Preferred methods of measuring reporter coding sequence translation involve luminescence, fluorescence, or an immunoassay. For example, a reporter coding sequence may encode a luminescent or fluorescent protein such that the level of translation may be monitored through measurement of a luminescent or fluorescent signal. A suitable example of a luminescent reporter coding sequence is luciferase. A suitable example of a fluorescent reporter coding sequence is green fluorescent protein.

Measuring levels of translated protein using an immunoassay is also well known in the art. Any suitable immunoassay which allows for detection of a reporter coding sequence by an antibody may be used. Any suitable commercially available antibody for a given target may be used. An example of a suitable immunoassay is Enzyme-Linked ImmunoSorbent Assay (ELISA). In some embodiments, the ELISA assay may be performed in flat plates where wells are coated with binding proteins or antibodies which can bind and allow for detection of the translated reporter polypeptide. Other types of immunoassay include immunoprecipitation and Western blotting.

Modulators of pneumovirus replication can be formulated into pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the modulators of pneumovirus replication may be included in a pharmaceutical composition which is formulated for slow release, such as in microcapsules formed from biocompatible polymers or in liposomal carrier systems according to methods known in the art.

The dose of a modulator of pneumovirus replication may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg of body weight, according to the activity of the specific modulator, the age, weight and conditions of the subject to be treated and the frequency and route of administration. Preferably, daily dosage levels are from 5 mg to 2 g. That dose may be provided as a single dose or may be provided as multiple doses, for example taken at regular intervals, for example 2, 3 or 4 doses administered daily.

Embodiments of the invention are illustrated by the following examples.

Scheme 1 Synthesis of ligands in Tables 1 and 2.

$$R^1\text{-Ph-NCX} + H_2N\text{-Ph-}R^2 \xrightarrow{CH_2Cl_2} R^1\text{-Ph-NH-C(X)-NH-Ph-}R^2$$

Library 1 X = O
Library 2 X = S

Scheme 2 Synthesis of ligands in Tables 3 and 4.

$$R^1\text{-Ph-NCX} + R^2NH_2 \xrightarrow{CH_2Cl_2} R^1\text{-Ph-NH-C(X)-NH-}R^2$$

Library 3 X = O
Library 4 X = S

TABLE 1
Library 1 diarylureas prepared and summary of activities in cellular RSV TCID$_{50}$ assay.
| Cpd no. | Structure | Solubility in cell medium | Activity | Toxicity |
| --- | --- | --- | --- | --- |
| 1 | 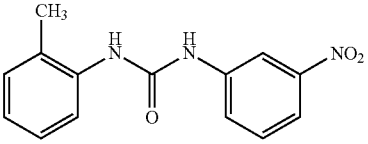 [SMILES: Cc1ccccc1NC(=O)Nc1cccc([N+](=O)[O-])c1] | poor | ++/+++ | toxic at 32 μM |
| 2 | 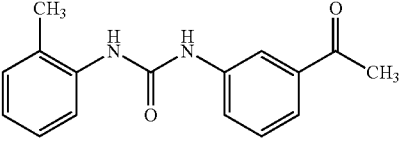 [SMILES: CC(=O)c1cccc(NC(=O)Nc2ccccc2C)c1] | good | – | very low |
| 3 | 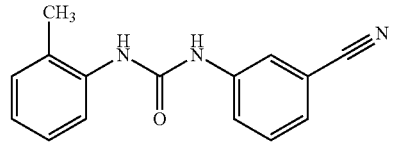 [SMILES: Cc1ccccc1NC(=O)Nc1cccc(C#N)c1] | good | + | low |
| 4 | 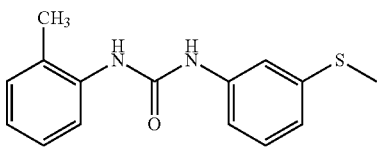 [SMILES: CSc1cccc(NC(=O)Nc2ccccc2C)c1] | good | +++++ | some toxicity at 100 μM |
| 5 | 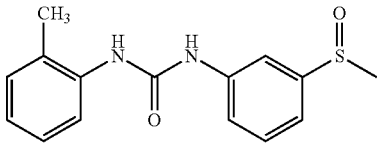 [SMILES: Cc1ccccc1NC(=O)Nc1cccc(S(C)=O)c1] | good | – | very low |
| 6 | 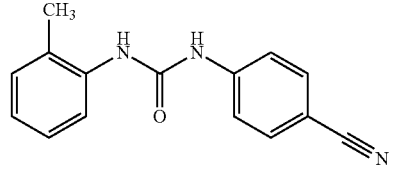 [SMILES: Cc1ccccc1NC(=O)Nc1ccc(C#N)cc1] | good | +++++ | low |
| 7 | 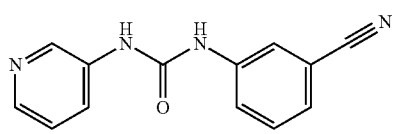 [SMILES: N#Cc1cccc(NC(=O)Nc2cccnc2)c1] | moderate | + | low |
| 8 | 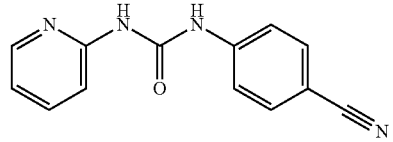 [SMILES: N#Cc1ccc(NC(=O)Nc2ccccn2)cc1] | moderate | + | toxic at 100, 32, 10 μM |
| 9 | 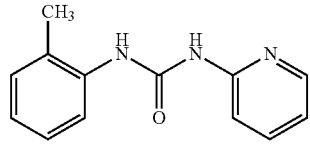 [SMILES: Cc1ccccc1NC(=O)Nc1ccccn1] | good | – | low |

TABLE 1-continued
Library 1 diarylureas prepared and summary of activities in cellular RSV TCID$_{50}$ assay.
| Cpd no. | Structure | Solubility in cell medium | Activity | Toxicity |
| --- | --- | --- | --- | --- |
| 10 | 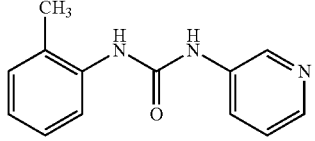 [SMILES: Cc1ccccc1NC(=O)Nc1cccnc1] | moderate | − | low |
| 11 | 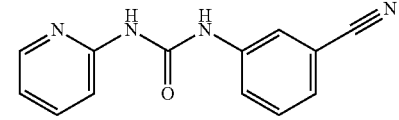 [SMILES: N#Cc1cccc(NC(=O)Nc2ccccn2)c1] | moderate | ++ | toxic at 100 μM |
| 12 | 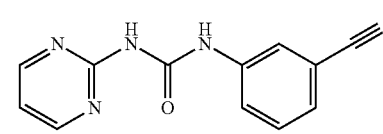 | poor | ++ | toxic at 100 μM |
| 13 | 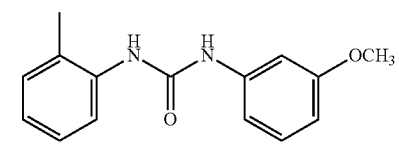 [SMILES: COc1cccc(NC(=O)Nc2ccccc2C)c1] | good | +++ | toxic at 100 μM |
| 14 | 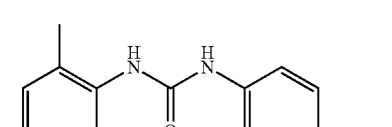 | good | ++++ | low |
| 15 | 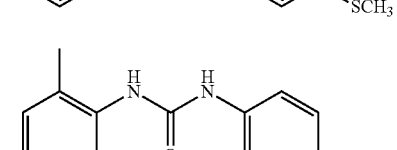 | good | +++ | low |
| 16 | 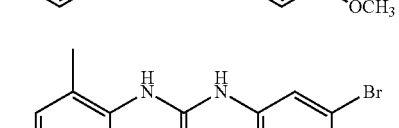 | moderate | + | toxic at 100 μM |
| 39 | 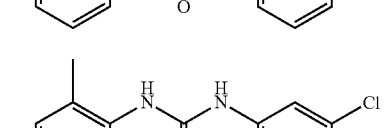 | Moderate at 100 μM | +++ | Some toxicity at 100 μM |
| 40 | 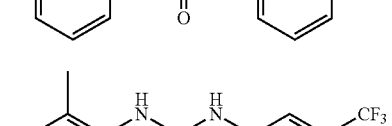 | Good | +/++ | Low |
| 41 | 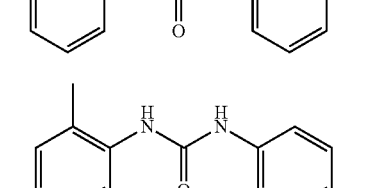 | Moderate at 100 μM | | Low |

TABLE 1-continued

Library 1 diarylureas prepared and summary of activities in cellular RSV $TCID_{50}$ assay.

| Cpd no. | Structure | Solubility in cell medium | Activity | Toxicity |
|---|---|---|---|---|
| 42 | (2-methylphenyl)-NH-C(=O)-NH-(4-SCF₃-phenyl) | Good | Plaques reduced | Very toxic at 100 μM |
| 43 | (2-methylphenyl)-NH-C(=O)-NH-(4-OCF₃-phenyl) | Good | Plaques reduced | Toxic at 100 μM |
| 44 | (2-methylphenyl)-NH-C(=O)-NH-(4-I-phenyl) | Moderate at 100 μM | Inactive | Low |
| 45 | (2-methylphenyl)-NH-C(=O)-NH-(3,4-diOCH₃-phenyl) | Good | Inactive | Low |

Solubility refers to a solution of ligand in DMSO (20 mM) diluted in cell media to a working concentration of 100 μM and ranges from 'very poor' (almost insoluble) to 'very good' remaining freely soluble over extended periods at 4° C.

TABLE 2

Library 2, diarylthioureas prepared and summary of activities in cellular RSV $TCID_{50}$ assay.

| Cpd no. | Structure | Solubility in cell medium | Activity | Toxicity |
|---|---|---|---|---|
| 17 | (2-methylphenyl)-NH-C(=S)-NH-(3-NO₂-phenyl) | good | + | toxic at 100 μM |
| 18 | (2-methylphenyl)-NH-C(=S)-NH-(3-CN-phenyl) | very good | − | low |
| 19 | (2-methylphenyl)-NH-C(=S)-NH-(4-SCH₃-phenyl) | very good | − | low |

TABLE 2-continued

Library 2, diarylthioureas prepared and summary of activities in cellular RSV TCID$_{50}$ assay.

| Cpd no. | Structure | Solubility in cell medium | Activity | Toxicity |
|---|---|---|---|---|
| 20 | 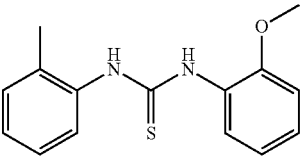 [SMILES: COc1ccccc1NC(=S)Nc1ccccc1C] | very good | − | low |

Solubility refers to a solution of ligand in DMSO (20 mM) diluted in cell media to a working concentration of 100 μM and ranges from 'very poor' (almost insoluble) to 'very good' remaining freely soluble over extended periods at 4° C.

TABLE 3

Library 3, alkylaryl ureas prepared and summary of activities in cellular RSV TCID$_{50}$ assay.

| Cpd no. | Structure | Solubility in cell medium | Activity | Toxicity |
|---|---|---|---|---|
| 21 | 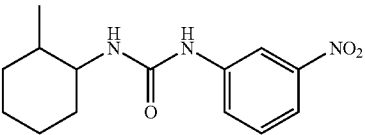 [SMILES: CC1CCCCC1NC(=O)Nc1cccc([N+](=O)[O-])c1] | moderate | +++ | toxic at 100 μM |
| 22 | 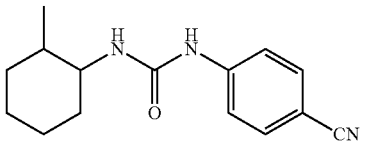 [SMILES: CC1CCCCC1NC(=O)Nc1ccc(C#N)cc1] | moderate | + | low |
| 23 | 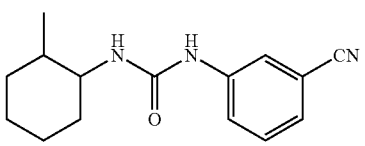 [SMILES: CC1CCCCC1NC(=O)Nc1cccc(C#N)c1] | moderate | + | low |
| 24 | 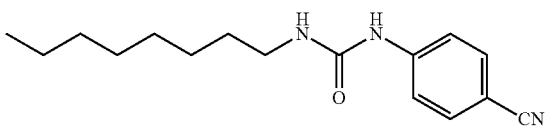 [SMILES: CCCCCCCCNC(=O)Nc1ccc(C#N)cc1] | good | + | low |
| 25 | 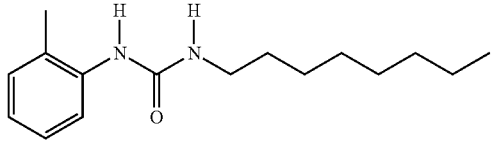 [SMILES: CCCCCCCCNC(=O)Nc1ccccc1C] | moderate | ++ | low |
| 26 | 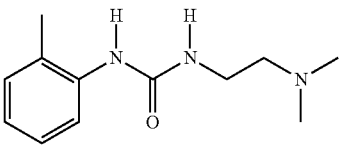 [SMILES: Cc1ccccc1NC(=O)NCCN(C)C] | good | − | low |

TABLE 3-continued

Library 3, alkylaryl ureas prepared and summary of activities in cellular RSV TCID$_{50}$ assay.

| Cpd no. | Structure | Solubility in cell medium | Activity | Toxicity |
|---|---|---|---|---|
| 27 | 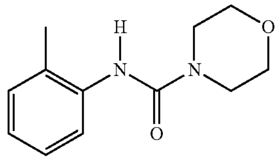 [SMILES: Cc1ccccc1NC(=O)N1CCOCC1] | good | – | low |

Solubility refers to a solution of ligand in DMSO (20 mM) diluted in cell media to a working concentration of 100 μM and ranges from 'very low' (almost insoluble) to 'very good' remaining freely soluble over extended periods at 4° C.

TABLE 4

Library 4 alkylaryl thioureas prepared and summary of activities in cellular RSV TCID$_{50}$.

| Cpd no. | Structure | Solubility in cell medium | Activity | Toxicity |
|---|---|---|---|---|
| 28 | 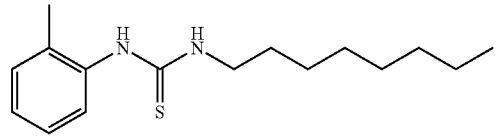 [SMILES: CCCCCCCCNC(=S)Nc1ccccc1C] | good | + | low |
| 29 | 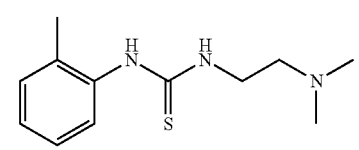 [SMILES: Cc1ccccc1NC(=S)NCCN(C)C] | good | – | low |
| 30 | 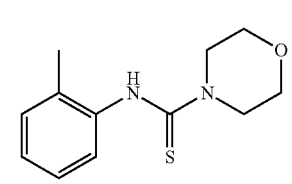 [SMILES: Cc1ccccc1NC(=S)N1CCOCC1] | very good | – | low |

Solubility refers to a solution of ligand in DMSO (20 mM) diluted in cell media to a working concentration of 100 μM and ranges from 'very low' (almost insoluble) to 'very good' remaining freely soluble over extended periods at 4° C.

Scheme S3 Synthesis of ligands in Table 5.

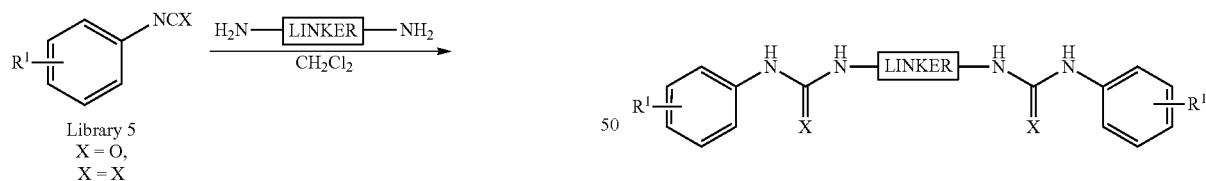

TABLE 5

Library 5, oligomeric ureas and thioureas prepared and summary of activities in cellular RSV TCID$_{50}$ assay.

| Cpd no. | Structure | Solubility | Activity | Toxicity |
|---|---|---|---|---|
| 31 | 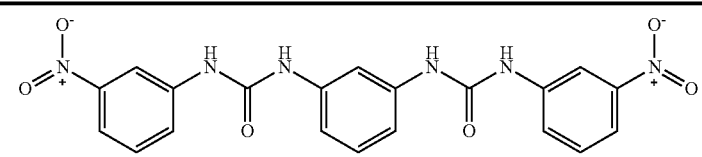 | very poor | ++ | toxic at 100 μM |

TABLE 5-continued

Library 5, oligomeric ureas and thioureas prepared and summary of activities in cellular RSV TCID$_{50}$ assay.

| Cpd no. | Structure | Solubility | Activity | Toxicity |
|---|---|---|---|---|
| 32 | 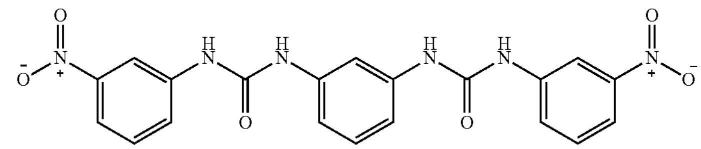 [SMILES: O=C(Nc1cccc(NC(=O)Nc2cccc([N+](=O)[O-])c2)c1)Nc1cccc([N+](=O)[O-])c1] | good | – | toxic at 100 μM |
| 33 | 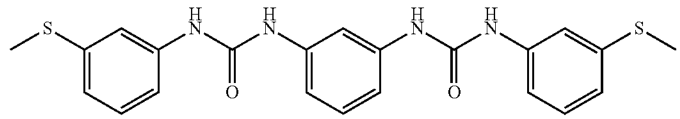 | poor | ++ | toxic at 100 μM |
| 34 | 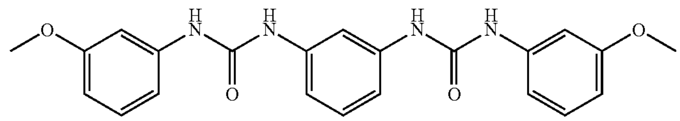 | poor | ++ | toxic at 100 μM |
| 35 | 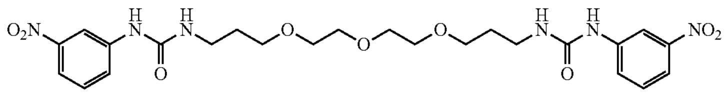 [SMILES: O=C(NCCCOCCOCCOCCCNC(=O)Nc1cccc([N+](=O)[O-])c1)Nc1cccc([N+](=O)[O-])c1] | good | | toxic at 100 μM |
| 36 | 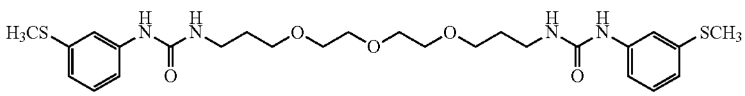 | good | | |
| 37 | 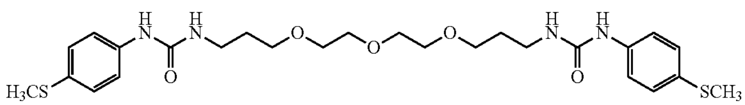 | good | +++ | toxic at 50 μM |
| 38 | 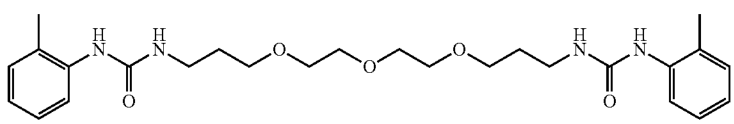 [SMILES: Cc1ccccc1NC(=O)NCCCOCCOCCOCCCNC(=O)Nc1ccccc1C] | good | | toxic at 50 μM |

Solubility refers to a solution of ligand in DMSO (20 mM) diluted in cell media to a working concentration of 100 μM and ranges from 'very low' (almost insoluble) to 'very good' remaining freely soluble over extended periods at 4° C.

General Experimental. Reagents and chemicals were purchased from Sigma-Aldrich and Acros and were used as supplied; solvents were purchased from Fisher and were used as supplied. All reactions were carried out under an atmosphere of nitrogen. Silica flash chromatography was carried out under low pressure using Merck silica gel 60 H (230-400 mesh). NMR spectra were acquired on Bruker DPX 300 or DPX 400 spectrometers with tetramethylsilane, δ=0 ppm as an internal standard. Assignments were made using 2D methods including COSY, HMBC and HMQC NMR and coupling constants quoted to the nearest 1 Hz. Low-resolution mass spectra were measured on an Agilent 6130B ESI-quad instrument with an electrospray ionization (ESI) mass selective detector in positive ion or negative ion mode as indicated. MALDI mass spectra were acquired on a Bruker Ultraflex II instrument. High-resolution mass spectra (HRMS) were acquired on a Bruker MicroTOF instrument with an ESI mass selective detector in either positive or negative ion mode. Infrared spectra were acquired with a Bruker Alpha FT-IR spectrophotometer. Melting points (mps) were determined on a Stuart SMP10 melting point apparatus; mp>250° C. were measured on an Olympus BH2 microscope equipped with a Linkam HFS 91 heating stage, or differential scanning calorimeter (DSC, Mettler Toledo DSC1-400). Warwick Analytical Service Limited, performed CHN microanalysis using a CE440 Elemental Analyser.

Preparation of Compounds

SAFETY Aromatic amines are highly toxic and considered as known or suspected human carcinogens. Isocyanates are sensitizers and toxic or highly toxic and their endpoint of hydrolysis is the parent amines. All procedures were carried out in an efficient fumehood, wearing standard laboratory protection. In addition, all reagents and reaction vessels were handled wearing a pair of thin nitrile gloves overgloved with medium weight nitrile gloves. All waste, including aqueous was disposed in specifically labeled containers.

General Procedure I—Addition of Aromatic Amines to Isocyanates

Aromatic ureas or thioureas were prepared using a previously reported general method.[1] To a solution of the amine (1 equiv., 5 mmol) in dry dichloromethane (5 mL) under dry $N_2$ was added the isocyanate (1 equiv., 5 mmol) in dry dichloromethane (~10 mL) with stirring, and left overnight at room temperature. The precipitate was collected by filtration and washed with a little ethanol, or if no precipitate, volatiles were removed under reduced pressure on a rotary evaporator. The resulting mixture was then purified through either recrystallization or a flash silica column (details specified) to provide the desired product.

Preparation of 3-(2-methylphenyl)-1-(3-nitrophenyl)urea (1),

Compound 1 was prepared from o-toluidine and 3-nitrophenylisocyanate using General Procedure I on 20 mmol scale to give, after recrystallization from ethanol, the title product 1 as a cotton wool-like solid (3.782 g, 69%); mp 216-218° C.; $^1$H NMR (400 MHz, DMSO-$d_6$) δ 9.53 (br. s., 1H), 8.59 (t, J=2 Hz, 1H), 8.08 (br. s., 1H), 7.83 (ddd, J=8, 2, 1 Hz, 1H), 7.80 (dd, J=8, 1 Hz, 1H), 7.71 (ddd, J=8, 2, 1 Hz, 1H), 7.58 (t, J=8 Hz, 1H), 7.15-7.23 (m, 2H), 7.01 (dt, J=7, 1 Hz, 1H), 2.27 (s, 3H) ppm; m/z $C_{14}H_{13}N_3O_3$ (ESI pos. mode) 294.0 (MNa$^+$); m/z (ESI neg. mode) 306.0 (M$^{35}$Cl$^-$), 270.1 (M-H$^+$).

In agreement with literature data: Radi, M.; Falchi, F.; Garbelli, A.; Samuele, A.; Bernardo, V.; Paolucci, S.; Baldanti, F.; Schenone, S.; Manetti, F.; Maga, G.; Botta, M. *Bioorg. Med. Chem. Lett.* 2012, 22, 2094-2098.

Preparation of 1-(3-acetylphenyl)-3-(2-methylphenyl)urea (2)

o-Toluidine and 3-acetylphenylisocyanate were combined using General Procedure I on a 3.10 mmol scale to give, after recrystallization from ethanol, the title product 2 as off-white crystals (0.454 g, 55%); mp 198-199° C.; $^1$H NMR (300 MHz, DMSO-$d_6$) δ 9.26 (s, 1H), 8.07 (t, J=1 Hz, 1H), 7.96 (s, 1H), 7.83 (d, J=8 Hz, 1H), 7.70 (dd, J=8, 1 Hz, 1H), 7.58 (d, J=8 Hz, 1H), 7.44 (t, J=8 Hz, 1H), 7.11-7.22 (m, 2H), 6.96 (dt, J=7, 1 Hz, 1H), 2.57 (s, 3H), 2.25 (s, 3H) ppm; $^{13}$C NMR (75 MHz, DMSO-$d_6$) δ 197.7, 152.6, 140.3, 137.4, 137.2, 130.2, 129.2, 127.7, 126.1, 122.9, 122.5, 121.7, 121.2, 117.1, 26.7, 17.8 ppm; $v_{max}$ (solid) 3282, 3080, 3026, 2974, 1670, 1641, 1586, 1560, 1433, 1360, 1274, 1239, 915, 795, 765, 662 cm$^{-1}$. m/z (ESI neg. mode) 267.1 (M-H)$^-$. Elemental analysis calcd for $C_{16}H_{16}N_2O_2$: C, 71.62; H, 6.01; N, 10.44. Found: C, 71.41; H, 5.93, N, 10.28.

Preparation of 3-(3-cyanophenyl)-1-(2-methylphenyl)urea (3)

o-Toluidine and 3-cyanophenylisocyanate were combined using General Procedure I on a 3.47 mmol scale to give, after recrystallization from ethanol, the title product 3 as a cotton wool-like solid; mp 200-201° C.; $^1$H NMR (300 MHz, DMSO-$d_6$) δ 9.35 (br. s., 1H), 8.08 (br. s., 1H), 8.01 (s, 1H), 7.78 (d, J=8 Hz, 1H), 7.65 (d, J=9 Hz, 1H), 7.50 (t, J=8 Hz, 1H), 7.42 (d, J=7 Hz, 1H), 7.12-7.22 (m, 2H), 6.98 (t, J=7 Hz, 1H), 2.25 (s, 3H) ppm; $^{13}$C NMR (75 MHz, DMSO-$d_6$) δ 152.5, 140.7, 136.9, 130.2 (2C), 128.2, 126.1, 125.1, 123.2, 122.6, 121.6, 120.5, 118.9, 111.6, 18.2 ppm; methyl peak missing but seen on HMQC at 18.2 ppm. Peak at 130.2 ppm determined to be 2C (non identical) by HMQC; $v_{max}$ (solid) 3323, 3271, 2232, 1643, 1585, 1556, 1458, 1433, 1289, 1248, 795, 774, 753, 658 cm$^{-1}$; m/z (ESI pos. mode) 274.1 (MNa$^+$); m/z 288.0 (ESI neg. mode) (M$^{37}$Cl$^-$), 286.0 (M$^{35}$Cl$^-$), 250.1 (M-H$^+$). Elemental analysis calcd for $C_{15}H_{13}N_3O$: C, 71.70; H, 5.21; N, 16.72. Found: C, 71.65; H, 5.16; N, 16.64.

Preparation of 1-(2-methylphenyl)-3-[3-(methylsulfanyl)phenyl]urea (4)

o-Toluidine and 3-methylthiophenylisocyanate were combined using General Procedure I on a 3.03 mmol scale to give, after recrystallization from ethanol, the title product 4 as an amorphous solid (0.362 g, 44%); mp 175-176° C.; $^1$H NMR (400 MHz, DMSO-$d_6$) δ 9.06 (s, 1H), 7.93 (s, 1H), 7.82 (dd, J=8, 1 Hz, 1H), 7.49 (t, J=2 Hz, 1H), 7.23 (t, J=8 Hz, 1H), 7.12-7.21 (m, 3H), 6.96 (dt, J=7, 1 Hz, 1H), 6.87 (td, J=8, 1 Hz, 1H), 2.47 (s, 3H), 2.25 (s, 3H) ppm; $^{13}$C NMR (101 MHz, DMSO-$d_6$) δ 152.6, 140.4, 138.6, 137.2, 130.2, 129.3, 127.6, 126.1, 122.8, 121.1, 119.1, 114.9, 114.5, 17.8, 14.6 ppm; $v_{max}$ (neat) 3285, 1632, 1606, 1555, 1478, 1459, 1288, 1260, 1232, 926, 848, 772, 743, 665 cm$^{-1}$; m/z (ESI pos. mode) 295.0 (MNa$^+$); m/z (ESI neg. mode) 307.0 (M$^{35}$Cl$^-$), 271.1 (M-H$^+$). HRMS (ESI pos. mode) m/z $C_{15}H_{16}N_2NaOS$ required 295.0876. Found m/z 295.0877.

Preparation of 3-(3-methanesulfinylphenyl)-1-(2-methylphenyl)urea (5)

To a stirred solution of 1-(2-methylphenyl)-3-[3-(methylsulfanyl)phenyl]urea 4 (0.25 g, 0.92 mmol) in acetone-water (2:1 v/v, 15 mL) at 0° C. was added dropwise a solution of sodium periodate (0.96 g, 0.92 mmol) in water (8 mL). A thick white precipitate of sodium iodate formed, which was removed by filtration after 4 hours and washed with a small portion of acetone. The filtrate was extracted with ethyl acetate (3 x 20 mL), with the addition of brine (15 mL) for the final extraction. The combined organics were washed with water, dried (MgSO$_4$) and evaporated under reduced pressure to give the crude product. Purification by flash chromatography (SiO$_2$, 1% MeOH-EtOAc) gave a solid which was recrystallized from hot ethanol-water (1:2 v/v) to give the title product 5 as a white powder (0.098 g, 35%); mp 139-144° C.; $^1$H NMR (300 MHz, DMSO-$d_6$) δ 9.35 (s, 1H), 7.97 (s, 1H), 7.87 (t, J=2 Hz, 1H), 7.83 (d, J=8 Hz, 1H), 7.51-7.57 (m, J=8, 2 Hz, 1H), 7.47 (t, J=8 Hz, 1H), 7.23 (td, J=7, 1 Hz, 1H), 7.11-7.21 (m, 2H), 6.97 (dt, J=7, 1 Hz, 1H), 2.73 (s, 3H), 2.25 (s, 3H) ppm; $^{13}$C NMR (75 MHz, DMSO-$d_6$) δ 152.5, 147.1, 140.8, 137.1, 130.2, 129.7, 127.7, 126.1, 122.9, 121.2, 119.7, 116.5, 112.3, 43.3, 17.8 ppm; $v_{max}$ (solid) 3438, 3292, 3056, 2917, 1640, 1585, 1457, 1425, 1242, 1019, 789, 761 cm$^{-1}$; m/z (ESI pos. mode) 311.0 (MNa$^+$); (ESI neg. mode) 323.0 (M$^{35}$Cl$^-$), 287.1 (M-H$^+$)$^-$. HRMS (ESI pos. mode) m/z $C_{15}H_{17}N_2O_2S$ (MH$^+$) required 289.1005. Found m/z 289.1001 $C_{15}H_{17}N_2O_2S$.

Preparation of 1-(4-cyanophenyl)-3-(2-methylphenyl)urea (6)

o-Toluidine and 4-cyanophenylisocyanate were combined using General Procedure I on a 3.47 mmol scale to give, after recrystallization from ethanol (<20 mL), the title product 6 as white needles (0.548 g, 63%); mp 207-210° C.; $^1$H NMR (400 MHz, DMSO-$d_6$) δ 9.50 (br. s., 1H), 8.11 (br. s., 1H), 7.78 (dd, J=8, 1 Hz, 1H), 7.74 (td, J=9, 2 Hz, 2H), 7.65 (td, J=9,3 Hz, 2H), 7.15-7.23 (m, 2H), 7.00 (dt, J=8, 1 Hz, 1H), 2.26 (s, 3H) ppm; $^{13}$C NMR (101 MHz, DMSO-$d_6$) δ 152.2, 144.3, 136.8, 133.3, 130.2, 128.3, 126.2, 123.3, 121.6, 119.3, 117.8, 103.1, 17.8 ppm; $v_{max}$ (solid) 3285, 3067, 3024, 2227, 1637, 1583, 1540, 1456, 1407, 1294, 1241, 1175, 847, 836, 755, 648, 552 cm$^{-1}$; m/z (ESI pos. mode) 274.0 (MNa$^+$), 252.1 (MH$^+$); m/z (ESI neg. mode) 286.0 (M$^{35}$Cl$^-$), 250.1 (M-H$^+$)$^-$. Elemental analysis calcd for $C_{15}H_{13}N_3O$: C, 71.70; H, 5.21; N, 16.72. Found: C, 71.51; H, 5.16; N, 16.64.

Preparation of 3-(3-cyanophenyl)-1-(pyridin-3-yl)urea (7)

3-Aminopyridine and 3-cyanophenylisocyanate were combined using General Procedure I on a 3.47 mmol scale to give, after slow recrystallization from ethanol (~30 mL), the product as red-tinged crystals (0.269 g, 33%). A second recrystallization from a minimum of hot ethanol gave the title product 7 as a white cotton wool-like mass of crystals (0.255 g, 31%); mp 197-198° C. (dec.); $^1$H NMR (400 MHz, DMSO-$d_6$) δ 9.17 (s, 1H), 9.03 (s, 1H), 8.63 (d, J=3 Hz, 1H), 8.23 (dd, J=5, 2 Hz, 1H), 7.99 (t, J=2 Hz, 1H), 7.95 (ddd, J=8, 3, 2 Hz, 1H), 7.71 (ddd, J=8, 2, 1 Hz, 1H), 7.52 (t, J=8 Hz, 1H), 7.45 (td, J=8, 1 Hz, 1H), 7.34 (dd, J=8, 5 Hz, 1H) ppm; $^{13}$C NMR (101 MHz, DMSO-$d_6$) δ 152.5, 143.2, 140.4, 140.3, 136.0, 130.2, 125.6, 125.5, 123.6, 123.1, 121.0, 118.8, 111.6 ppm; $v_{max}$ (solid) 3285, 3249, 3068, 2230, 1712, 1582, 1537, 1475, 1424, 1326, 1278, 1247, 1199, 785, 739, 705, 679 cm$^{-1}$; m/z (ESI pos. mode) 239.0 (MH$^+$); (ESI neg. mode) 283.0 (M$^{35}$Cl$^-$), 237.1 (M-H$^+$). Elemental analysis calcd for C$_{13}$H$_{10}$N$_4$O: C, 65.54; H, 4.23; N, 23.52. Found: C, 65.47; H, 4.18; N, 23.42.

Preparation of 3-(4-cyanophenyl)-1-(pyridin-2-yl)urea (8)

2-Aminopyridine and 4-cyanophenylisocyanate were combined using General Procedure I on a 3.46 mmol scale to give the title product 8 as a white solid (0.20 g, 24%). Recrystallization of 160 mg from a minimum of hot ethanol gave a colourless solid (98 mg, 12%); mp 212-213° C. (dec.);$^1$HNMR (400 MHz, DMSO-d$_6$) δ 10.90 (br. s., 1H), 9.62 (s, 1H), 8.31 (ddd, J=5, 2, 1 Hz, 1H), 7.76-7.81 (m, 3H), 7.73 (td, J=9, 2 Hz, 2H), 7.54 (d, J=9 Hz, 1H), 7.06 (ddd, J=7, 5, 1 Hz, 1H); $^{13}$C NMR (101 MHz, DMSO-d$_6$) δ 152.4, 151.9, 147.0, 143.5, 138.7, 133.3 (2C), 119.2, 118.7 (2C), 118.0, 112.1, 104.0; v$_{max}$ (solid) 3203, 3060, 2973, 2221, 1702, 1581, 1476, 1414, 1305, 1243, 1155, 840, 770 cm$^{-1}$; m/z (ESI pos. mode) 261.0 (MNa$^+$), 239.0 (MH$^+$); (ESI neg. mode) 273.0 (M$^{35}$Cl$^-$), 237.1 (M-H$^+$)$^-$. Elemental analysis calcd for C$_{13}$H$_{10}$N$_4$O: C, 65.54; H, 4.23; N, 23.52. Found: C, 65.29; H, 4.13; N, 23.30.

Preparation of 1-(2-methylphenyl)-3-(pyridin-2-yl)urea (9)

2-Aminopyridine and o-tolyl isocyanate were combined using General Procedure I on a 3.76 mmol scale to give, after rcrystallization from hot ethanol, the title product 9 as a white solid (0.301 g, 35%); mp 212-213° C.; $^i$H NMR (400 MHz, DMSO-d$_6$) δ 10.94 (br. s., 1H), 9.78 (s, 1H), 8.29 (ddd, J=5, 2, 1 Hz, 1H), 8.05 (dd, J=8, 1 Hz, 1H), 7.77 (ddd, J=8, 7, 2 Hz, 1H), 7.30 (d, J=8 Hz, 1H), 7.22 (d, J=8 Hz, 1H), 7.18 (dt, J=8, 2 Hz, 1H), 7.02 (ddd, J=7, 5, 1, Hz, 1H), 6.98 (dt, J=7, 1 Hz, 1H) , 2.34 (s, 3H) ppm; $^{13}$C NMR (101 MHz, DMSO-d$_6$) δ 153.1, 152.3, 146.3, 138.8, 137.3, 130.2, 126.9, 126.2, 122.7, 120.3, 117.2, 111.9, 18.1 ppm; v$_{max}$ (solid) 3199, 3057, 2982, 2915, 1686, 1605, 1478, 1458, 1415, 1289, 1240 cm$^{-1}$; m/z (ESI pos. mode) 250.0 (MNa$^+$), 228.0 (MK); (ESI neg. mode): m/z 226.1 (M-H$^+$)$^-$. Elemental analysis calcd for C$_{13}$H$_{13}$N$_3$O: C, 68.70; H, 5.77; N, 18.49. Found: C, 68.61; H, 5.78; N, 18.43.

Preparation of 1-(2-methylphenyl)-3-(pyridin-3-yl)urea (10)

o-Tolyl isocyanate and 3-aminopyridine were combined using General Procedure I on a 3.76 mmol scale to give, after recrystallization from a minimum of hot ethanol, the title product 10 as white needles (0.278 g, 32%); mp 164-165° C.; $^1$H NMR (400 MHz, DMSO-d$_6$) δ 9.18 (s, 1H), 8.62 (d, J=3 Hz, 1H), 8.20 (dd, J=5, 2 Hz, 1H), 8.06 (s, 1H), 7.98 (ddd, J=, 8, 3, 2 Hz, 1H), 7.82 (dd, J=8, 1 Hz, 1H), 7.32 (dd, J=8, 5 Hz, 1H), 7.14-7.22 (m, 2H), 6.98 (dt, J=7, 1 Hz, 1H), 2.26 (s, 3H) ppm; $^{13}$C NMR (101 MHz, DMSO-d$_6$) δ 152.7, 142.7, 139.8, 137.1, 136.6, 130.2, 127.9, 126.2, 124.9, 123.6, 123.0, 121.4, 17.8 ppm; v$_{max}$ (solid) 3406, 2890, 1700, 1610, 1584, 1556, 1509, 1449, 1424, 1286, 1250, 802, 753, 703 cm$^{-1}$; m/z (ESI pos. mode): 250.0 (MNa$^+$), 228.1 (MH$^+$); (ESI neg. mode): m/z 226.1 (M-H$^+$). Elemental analysis calcd for C$_{13}$H$_{13}$N$_3$O: C, 68.70; H, 5.77; N, 18.49. Found: 68.58; H, 5.78; N, 18.37.

Preparation of 3-(3-cyanophenyl)-1-(pyridin-2-yl)urea (11)

2-Aminopyridine and 3-cyanophenyl isocyanate were combined using General Procedure I on a 3.46 mmol scale to give a white solid (220 mg). Recrystallization from hot ethanol, gave the title product 11 as white cotton wool-like crystals (0.140 g, 17%); mp 164-165° C.; $^1$ Hz NMR (400 MHz, DMSO-d$_6$) δ 10.93 (br. s., 1H), 9.63 (s, 1H), 8.31 (ddd, J=5, 2, 1 Hz, 1H), 8.08 (t, J=2 Hz, 1H), 7.75-7.82 (m, 2H), 7.54 (t, J=8 Hz, 1H), 7.46-7.50 (m, 2H), 7.05 (ddd, J=7, 5, 1 Hz, 1H) ppm; $^{13}$C NMR (101 MHz, DMSO-d$_6$) δ 152.5, 152.2, 146.9, 139.9, 138.7, 130.2, 126.0, 123.5, 121.4, 118.7, 117.8, 112.0, 111.7 ppm; v$_{max}$ (solid) 3207, 3059, 2982, 2228, 1707, 1609, 1582, 1562, 1479, 1417, 1317, 1150, 771, 725 cm$^{-1}$; m/z (ESI pos. mode) 487.2 (M$_2$Na$^+$). Elemental analysis calcd for C$_{13}$H$_{10}$N$_4$O: C, 65.54; H, 4.23; N, 23.52. Found: C, 65.48; H, 4.21; N, 23.61.

Preparation of 3-(3-cyanophenyl)-1-(pyrimidin-2-yl)urea (12)

2-Aminopyrimidine and 3-cyanophenyl isocyanate were combined using General Procedure I on a 3.47 mmol scale to give a white solid (~100 mg). Recrystallization from hot ethanol (poor solubility, 150 mL), gave the title product 12 as a white powder (0.077 g, 9%); mp 260-266° C.; 1H NMR (400 MHz, DMSO-d$_6$) δ 11.80 (br. s., 1H), 10.37 (br. s., 1H), 8.70 (d, J=5 Hz, 2H), 8.14 (t, J=2 Hz, 1H), 7.95 (td, J=8, 2 Hz, 1H), 7.57 (t, J=8 Hz, 1H), 7.53 (td, J=8, 2, Hz, 1H), 7.18 (t, J=5 Hz, 1H) ppm. Insufficient solubility for carbon NMR. v$_{max}$ (solid) 3140, 3065, 2980, 2916, 2223, 1693, 1615, 1582, 1561, 1515, 1407, 1300, 1240, 1225, 785, 725 cm$^{-1}$; m/z (ESI neg. mode) 274.0 (M$^{35}$Cl$^-$), 238.1 (M-H$^+$)$^-$; HRMS (ESI pos. mode) m/z C$_{12}$H$_9$N$_5$ONa required 262.0699 (MNa$^+$). Found m/z 262.0701. Barely soluble in CH$_2$Cl$_2$, insoluble in 80:20 MeOH:H$_2$O. Elemental analysis calcd for C$_{12}$H$_9$N$_5$O: C, 60.25; H, 3.79; N, 29.27. Found: C, 60.10; H, 3.670; N, 29.23.

Preparation of 3-(3-methoxyphenyl)-1-(2-methylphenyl)urea (13)

o-Toluidine and 3-methoxyphenylisocyanate using General Procedure I on a 3.35 mmol scale to give, after recrystallization from hot ethanol, the title product 13 as white needles (0.327 g, 39%); mp 162-162° C.; $^1$H NMR (300 MHz, DMSO-d$_6$) δ 9.03 (s, 1H), 7.91 (s, 1H), 7.84 (d, J=8 Hz, 1H), 7.10-7.22 (m, 4H), 6.91-6.98 (m, 2H), 6.55 (dd, J=8, 2 Hz, 1H), 3.73 (s, 3H), 2.24 (s, 3H) ppm; $^{13}$C NMR (75 MHz, DMSO-d$_6$) δ 159.7, 152.5, 141.1, 137.3, 130.1, 129.5, 127.4, 126.1, 122.6, 121.0, 110.2, 107.1, 103.6, 54.8, 17.8 ppm; v$_{max}$ (solid) 3274, 2923, 2826, 1633, 1590, 1545, 1455, 1293, 1225, 1160, 1055, 759 cm$^{-1}$; m/z (ESI pos. mode) 279.0 (MNa$^+$), 257.0 (MH$^+$); (ESI neg. mode) 291.0 (M$^{35}$Cl$^-$), 255.1 (M-H$^+$)$^-$. Elemental analysis calcd for C$_{15}$H$_{16}$N$_2$O$_2$: C, 70.29; H, 6.29; N, 10.93. Found: 70.12; H, 6.23; N, 10.88.

Preparation of 3-(2-methylphenyl)-1-[4-(methylsulfanyl)phenyl]urea (14)

o-Toluidine and 4-methylthiophenylisocyanate were combined using General Procedure I on a 3.46 mmol scale to give, after recrystallization from hot ethanol, the title product 14 as a white powder (0.315 g, 38%); mp 205-206° C.; $^1$H NMR (250 MHz, DMSO-d$_6$) δ 8.98 (s, 1H), 7.86 (s, 1H), 7.80 (d, J=8 Hz, 1H), 7.38-7.45 (m, J=9 Hz, 2H), 7.18-7.25 (m, J=8 Hz, 2H), 7.08-7.18 (m, 2H), 6.93 (dt, J=7, 1 Hz, 1H), 2.42 (s, 3H), 2.23 (s, 3H) ppm; $^{13}$C NMR (101 MHz, DMSO-d$_6$) δ 152.6, 137.6, 137.3, 130.2, 129.7, 127.8, 127.5, 126.1, 122.6, 121.0, 118.7, 17.9, 16.0 ppm; v$_{max}$ (solid) 3283, 2977, 2919, 1637, 1581, 1543, 1489, 1282, 1236, 826, 796, 760, 740 cm$^{-1}$; m/z (ESI pos. mode) 295.0 (MNa$^+$); (ESI neg. mode) 307.0 (M$^{35}$Cl$^-$), 271.0 (M-H)$^-$. Elemental analysis calcd for C$_{15}$H$_{16}$N$_2$OS: C, 66.15; H, 5.92; N, 10.29. Found: C, 65.96; H, 5.84; N, 10.17.

Preparation of 1-(4-methoxyphenyl)-3-(2-methylphenyl)urea (15)

o-Toluidine and 4-methoxyphenylisocyanate were combined using General Procedure I on a 3.35 mmol scale to give, after recrystallization from hot ethanol, the title product 15 as a white powder (0.300 g, 35%); mp 200-201° C.; $^1$H NMR (400 MHz, DMSO-d$_6$) δ 8.83 (s, 1H), 7.86 (d, J=8 Hz, 1H), 7.82 (s, 1H), 7.35-7.40 (m, 2H), 7.11-7.19 (m, 2H), 6.94 (dt, J=8, 1 Hz, 1H), 6.86-6.91 (m, J=9 Hz, 2H), 3.73 (s, 3H), 2.25 (s, 3H) ppm; $^{13}$C NMR (101 MHz, DMSO-d$_6$) δ 154.3, 152.8, 137.6, 132.9, 130.1, 127.2, 126.1, 122.4, 120.8, 119.7, 114.0, 55.1, 17.9 ppm; v$_{max}$ (solid) 3292, 3042, 2837, 1638, 1598, 1555, 1509, 1455, 1239, 1032, 828, 799 cm$^{-1}$; m/z (ESI pos. mode) 279.0 (MNa$^+$), 257.0 (MH$^+$); (ESI neg. mode) 291.0 (M$^{35}$Cl)$^-$, 255.1 (M-H$^+$)$^-$. Elemental analysis calcd for C$_{15}$H$_{16}$N$_2$O$_2$: C, 70.29; H, 6.29; N, 10.93. Found: C, 70.02; H, 6.13; N, 10.80.

Preparation of 1-(3-bromophenyl)-3-(2-methylphenyl)urea (16).

o-Tolyl isocyanate (666 mg, 5 mmol) and 3-bromoaniline (860 mg, 5 mmol) were combined using General Procedure I to produce the title compound 16 as a white solid (1.011 g, 66%); mp 215-218° C.; 1H NMR (300 MHz, DMSO-d$_6$) δ 9.24 (s, 1H), 8.02 (s, 1H), 7.90 (t, J=2 Hz, 1H), 7.78 (d, J=8 Hz, 1H), 7.10 (m, 5H), 6.97 (t, J=8 Hz, 1H), 2.24 (s, 3H) ppm; $^{13}$C NMR (75 MHz, DMSO) δ 176.63, 147.86, 111.54, 77.57, 70.33, 40.29, 40.01, 39.74, 39.61, 39.46, 39.18, 38.90, 38.62 ppm; v$_{max}$ (solid) 3280, 1635, 1542 cm$^{-1}$; m/z (ESI pos. mode) 383.981 (MHBr$^+$, 100%), 405.956 (MHNaBr$^+$, 93%); HRMS (ESI pos. mode) m/z C$_{14}$H$_{13}$BrN$_2$ONa required: 327.0103. Found: 327.0167. Elemental analysis calcd for C$_{14}$H$_{13}$BrN$_2$O: C 55.10%, H 4.29%, N 9.18%. Found: C 54.88%, H 4.23%, N 9.01%.

Preparation of 3-(2-methylphenyl)-1-(3-nitrophenyl)thiourea (17)

o-Toluidine (0.54 g, 5 mmol) and 3-nitrophenylisothiocyanate (0.90 g, 5 mmol) were combined with General Procedure I to give, after recrystallization from hot methanol, the title product 17 as white crystals (0.41 g, 45%); mp 171-173° C.; $^1$H NMR (300 MHz, chloroform-d) δ 8.17 (t, J=2 Hz, 1H), 8.01-7.91 (m, 1H), 7.92-7.79 (m, 1H), 7.71 (s, 1H), 7.42 (t, J=8 Hz, 1H), 7.35-7.20 (m, 4H), 7.16 (s, 1H), 2.29 (s, 3H) ppm; $^{13}$C (75 MHz, chloroform-d) 0 180.5, 147.4, 141.0, 137.3 132.2, 134.9, 130.5, 129.6, 127.9, 126.8, 126.3, 118.5, 117.6, 17.8 ppm; v$_{max}$ (solid) 3340, 3149, 2956, 1534, 1497, 1459, 1339, 1283, 1258, 1237, 1208, 1155, 1108, 1089, 987, 945, 853, 805, 751, 741, 709, 687 cm$^{-1}$; m/z=286.0, (M$^+$), 310.0 (MNa$^+$); HRMS (ESI pos. mode) m/z C$_{14}$H$_{13}$N$_3$NaO$_2$S (MNa$^+$) required 310.0621. Found: 310.0615.

Preparation of 1-(3-cyanophenyl)-3-(2-methylphenyl)thiourea (18)

o-Toluidine (0.54 g, 5 mmol) and 3-cyanophenylisothiocyanate (0.90 g, 5 mmol) were combined with General Procedure Ito give, after recrystallization from hot ethanol, the title product 18 as pale yellow crystals (0.42 g, 31%); mp 166-168° C.; $^1$H NMR (300 MHz, chloroform-d) δ 7.45-7.30 (m, 3H), 7.35-7.20 (m, 6H), 7.17 (s, 1H), 2.29 (s, 3H) ppm; $^{13}$C (75.5 MHz, DMSO-d$_6$) δ 180.5, 140.6, 137.4, 134.9, 130.4, 129.7, 128.4, 127.9, 127.7, 126.8, 126.6, 126.2, 118.6, 111.0 17.8 ppm; v$_{max}$ (solid) 3217, 3145, 2979, 2240, 1586, 1543, 1519, 1481, 1455, 1429, 1358, 1320, 1297, 1283, 1270 cm$^{-1}$; m/z (ESI pos. mode) 268.0, (MH$^+$), 290.0 (MHNa$^+$); HRMS (ESI pos. mode) m/z C$_{15}$H$_{13}$N$_3$NaS (MNa$^{30}$) required 290.0722. Found: 290.0729.

Preparation of 1-(2-methoxyphenyl)-3-(2-methylphenyl)thiourea (19)

o-Toluidine (0.54 g, 5 mmol) and 4-methylthiophenylisothiocyanate (0.91 g, 5 mmol) were combined with General Procedure Ito give, after recrystallization from hot ethanol the title product 19 as white crystals (0.52 g, 38%); mp 140-142° C.; $^1$H NMR (300 MHz, chloroform-d) δ 8.18 (d, J=8 Hz, 1H), 7.75 (s, 1H), 7.53 (s, 1H), 7.35-7.18 (m, 4H), 7.09 (t, J=8, 2 Hz, 1H), 6.93 (t, J=8, 1 Hz, 1H), 6.81 (d, 1H), 3.68 (s, 3H), 2.28 (s, 3H); $^{13}$C (75.5 MHz-DMSO-d$_6$) δ 180.0, 151.6, 137.5, 134.9, 130.3, 128.2, 127.7, 126.6, 126.1, 125.8, 125.3, 119.8, 111.4, 55.6, 17.7 ppm; v$_{max}$ (solid) 3336, 3125, 2936, 1598, 1533, 1505, 1484, 1459, 1434, 1276, 1248, 1202, 1179, 1159, 1044, 1026, 745, 725, 699 cm$^{-1}$; m/z 273.0 (MH$^+$), 295.0 (MHNa$^+$); HRMS (ESI pos. mode) m/z C$_{15}$H$_{16}$N$_2$NaOS (MHNa$^{30}$) required 295.0876. Found: 295.0874.

Preparation of 3-(2-methylphenyl)-1-[4-(methylsulfanyl) phenyl]thiourea, (20)

o-Toluidine (0.54 g, 5 mmol) and 4-methylthiophenylisothiocyanate (0.91 g, 5 mmol) were combined with General Procedure Ito give, after recrystallization from hot ethanol, the title product 20 as white crystals (0.93 g, 62%); mp 149-151° C.; $^1$H NMR (300 MHz, DMSO-d$_6$) δ 9.64 (s, 1H), 9.33 (s, 1H), 7.48-7.37 (m, 2H), 7.30-7.10 (m, 6H), 2.46 (s, 3H), 2.24 (s, 3H); $^{13}$C (75.5 MHz, DMSO-d$_6$) δ 180.3, 164.0, 137.7, 136.7, 134.8, 133.5, 130.3, 127.9, 126.4, 126.4, 126.1, 124.6, 124.4, 17.9, 15.2 ppm; v$_{max}$ (solid) 3223, 1580 (w), 1498 (s), 1347, 1255, 1201, 1089, 1016, 853, 790, 751, 718, 627 cm$^{-1}$; m/z 311.0 (MHNa$^+$); HRMS (ESI pos. mode) m/z C$_{15}$H$_{16}$N$_2$NaS$_2$ (MHNa$^+$) required 311.0647. Found: 311.0637.

Preparation of 3-(2-methylcyclohexyl)-1-(3-nitrophenyl)urea 21

2-Methylcyclohexylamine and 3-nitrophenylisocyanate were combined using General Procedure I on a 3.05 mmol scale, to give after recrystallization from hot ethanol, the title product 21 as yellow needles (0.202 g, 24%); mp 173-175° C.; $^1$H NMR (400 MHz, DMSO-d$_6$) δ 8.85 (s, 1H), 8.53 (t, J=2 Hz, 1H), 7.74 (dd, J=2, 8 Hz, 1H), 7.61 (d, J=9 Hz, 1H), 7.50 (t, J=8 Hz, 1H), 6.18 (d, J=9 Hz, 1H), 3.16 (ddt, J=4, 9, 11 Hz, 1H), 1.86 (dd, J=3, 13 Hz, 1H), 1.72 (dt, J=2, 13 Hz, 2H), 1.62 (d, J=12 Hz, 1H), 0.98-1.37 (m, 5H), 0.91 (d, J=7 Hz, 3H) ppm; $^{13}$C NMR (75 MHz, DMSO-d$_6$) δ 154.4, 148.1, 141.9, 129.8, 123.5, 115.3, 111.3, 53.9, 37.6, 34.0, 33.5, 25.3, 25.2, 19.2 ppm; v$_{max}$ (solid) 2195, 3072, 2927, 2856, 1655, 1638, 1519, 1346 cm$^{-1}$; m/z (ESI pos. mode) 300.0 (MNa$^+$); (ESI neg. mode) 312.1 (M$^{35}$Cl$^-$), 276.1 (M-H$^+$). Elemental analysis calcd for C$_{14}$H$_{19}$N$_3$O$_3$: C, 60.63; H, 6.91; N, 15.15. Found: C, 60.53; H, 6.85; N, 15.04.

Preparation of 1-(4-cyanophenyl)-3-(2-methylcyclohexyl) urea (22)

4-Cyanophenyl isocyanate (721 mg, 5 mmol) and 1-amino-2-methyl cyclohexane (566 mg, 5 mmol) were combined with General Procedure I to produce a white solid. This product was recrystallized from hot ethanol and a small volume of water to give the title compound 22 as a white powder (529 mg, 49%), mp 190-192° C.; $^1$H NMR (300 MHz, chloroform-d) δ 7.63 (s, 1H), 7.56-7.42 (dd, J=9 Hz, 5 Hz, 4H), 5.24 (d, J=9 Hz, 1H), 3.26 (dq, J=11, 4 Hz, 1H), 1.98 (dd J=14, 3 Hz) 1.76-1.61 (m, 4H), 1.16-0.96 (m, 4H) 0.94 (d, J=7 Hz, 3H) ppm; $^{13}$C NMR (75.5 MHz, chloroform-d) δ 154.8, 144.0, 133.3, 119.4, 118.3, 104.5, 58.6, 55.1, 38.7, 34.3, 25.6, 25.4, 19.2 ppm; v$_{max}$ (solid) 3302, 2924, 2226, 1634, 1558, 1516, 1310, 1228, 1175, 835 cm$^{-1}$; m/z (ESI pos. mode) 258.1 (MH$^+$, 36%), 280.1 (MNa$^+$, 100%); HRMS m/z (ESI pos. mode) C$_{15}$H$_{20}$N$_3$O required 258.1601. Found 258.1600. Elemental analysis calcd for C$_{15}$H$_{19}$N$_3$O: C, 70.01%, H, 7.44%, N, 16.33%. Found C 69.98%, H 7.44%, N 16.20%.

Preparation of 1-(3-cyanophenyl)-3-(2-methylcyclohexyl) urea (23)

To a stirred solution of 2-methylcyclohexylamine (0.57 g, 5 mmol) in dichloromethane (5 mL) at 0° C. under nitrogen was added a solution of 3-cyanophenyl isocyanate (0.72 g, 5 mmol) in dichloromethane (5 mL) from a pressure equalized dropping funnel. The reaction was stirred overnight and the crude product was isolated by evaporation under reduced pressure. Trituration with ethanol-water and brief contact with dry ice/acetone gave the title product 23 as a white solid (0.38 g, 30%); mp 168-174° C.; $^1$H (300 MHz, DMSO-d$_6$) δ 8.65 (s,1H), 7.94 (s, 1H), 7.55 (d, J=9 Hz, 1H), 7.41 (t, J=8 Hz, 1H), 7.30 (J=10 Hz, 1H), 6.18 (d, J=9 Hz, 1H) 3.14 (dq, J=10, 4 Hz, 1H), 1.85 (m, 1H), 1.78-1.51 (m, 4H), 1.35-1.00 (m, 6H), 0.90 (d, J=6 Hz, 3H) ppm; $^{13}$C (75.5 MHz, DMSO-d$_6$) δ 154.5, 141.5, 130.0, 124.2, 122.0, 119.9, 119.0, 111.4, 53.8, 37.7, 34.0, 33.5, 25.3, 25.2, 19.2 ppm; $v_{max}$ (solid) 3395, 3300, 2928, 2850, 1653, 1547, 1481, 1411, 1310, 1232, 1029, 880, 809, 686, 591, 475 cm$^{-1}$; m/z (ESI pos. mode) 280.1 (MNa$^+$), 258.1 (MH$^+$). HRMS (ESI pos. mode) m/z C$_{15}$H$_{20}$N$_3$O (MH$^+$) required 258.1601. Found 258.1602.

Preparation of 1-(4-cyanophenyl)-3-octylurea (24).

4-Cyanophenyl isocyanate (544 mg, 5 mmol) and octylamine (642 mg, 5 mmol) were combined using General Procedure I to produce a white solid. This product was purified using flash column chromatography (SiO$_2$, 30:70 EtOAc : petroleum ether)40-60°) to give the title compound 24 as a white powder (887 mg, 76%); mp 115-120° C.; $^1$H NMR (300 MHz, chloroform-d) δ 7.64 (s, 1H), 7.56-7.41 (m, 4H), 5.47 (t, J=6 Hz, 1H), 3.29-3.16 (q, J=7 Hz, 2H), 1.50 (m, 2H), 1.37-1.17 (m, 10H), 0.86 (t, J=7 Hz, 3H) ppm; $^{13}$C NMR (75 MHz, chloroform-d) δ 164.4, 132.7, 117.9, 42.7, 31.2, 29.4, 28.6, 26.3, 22.2 ppm; $v_{max}$ (solid) 3374, 2923, 2219, 1685, 1657, 1592, 1535, 1507, 1320, 1231, 1172, 835 cm$^{-1}$; m/z (ESI pos. mode) 272.1 (M-H$^+$, 100%). Elemental analysis calcd for C$_{16}$H$_{23}$N$_3$O: C 70.30%, H 8.48%, N 15.37%. Found: C 70.39%, H 8.46%, N 15.63%.

Preparation of 1-(2-methylphenyl)-3-octylurea, (25)

To a stirred solution of octylamine (0.65 g, 5 mmol) in dichloromethane (5 mL) at 0° C. under dry nitrogen was added a solution of 2-methylphenyl isocyanate (0.67 g, 5 mmol) in dichloromethane (5 mL) from a pressure equalized dropping funnel. The reaction was stirred overnight and the white solid was collected by filtration under reduced pressure on a sintered glass funnel. Recrystallization from hot ethanol, with addition of a small quantity of water, gave the title product 25 as a white solid (0.46 g, 36%); mp 113° C.; $^1$H (300 MHz, chloroform-d) δ 7.35 (1H, d, J=8 Hz), 7.20-7.05 (4H, m), 5.85 (1H, br. s.), 4.50 (1H, br with app. t structure), 3.20 (2H, dd, J=10, 7 Hz), 2.25 (3H, s), 1.60 (2H, s, bound H$_2$O), 1.48 (2H, m), 1.30-1.20 (10H, m), 0.85 (3H, t, J=7 Hz) ppm; $^{13}$C (75.5 MHz, chloroform-d) δ 164.6, 155.9, 135.5, 130.4, 126.5, 125.4, 125.0, 39.8, 31.2, 29.6, 28.7, 28.6, 26.2, 22.0, 17.3, 13.5 ppm; $v_{max}$ (solid) 3336, 3300, 2960, 2926, 2853, 1585, 1552, 1481, 1458, 1303, 1290, 1260, 1236, 1213, 1190, 1106, 1082, 1043, 758, 734 cm$^{-1}$; m/z (ESI neg. mode) 261 (M-H$^+$). HRMS (ESI pos. mode) m/z C$_{16}$H$_{26}$N$_2$NaO required 285.1937, found 285.1932.

Preparation of 3-[2-(dimethylamino)ethyl]1-(2-methylphenyl)urea (26)

To a stirred solution of N,N-dimethylethylamine (0.44 g, 5 mmol) in dichloromethane (5 mL) at 0° C. under dry nitrogen was added a solution of 2-methylphenyl isocyanate (0.67 g, 5 mmol) in dichloromethane (5 mL) dropwise from a pressure equalized dropping funnel. The reaction was stirred overnight then evaporated under reduced pressure. The solid product was recrystallized from warm diethyl ether with a few drops of dichloromethane, which gave after 4 days, the title product 26 as a white solid (0.72 g, 65%); mp 120-123° C.; $^1$H (300 MHz, chloroform-d) δ 7.50 (dd, J=8, 1 Hz, 1H), 7.20-7.10 (m, 3H) 6.95 (dd, J=7, 6 Hz, 1H), 5.65-5.58 (1H, m), 3.30 (2H, q, J=5.5 Hz), 2.40 (t, J=5.8 Hz, 2H), 2.24 (s, 3H), 2.17 (s, 6H) ppm; $^{13}$C (75.5 MHz, chloroform-d) δ 156.4, 136.2, 130.6, 130.1, 126.2, 124.3, 123.9, 58.4, 44.6, 37.4, 17.3 ppm; $v_{max}$ (solid) 3300, 2900, 2760, 1630, 1562, 1458, 1292, 1243, 1096, 1057, 850, 754, 665 cm$^{-1}$; m/z (ESI pos. mode) 222 (MH$^+$). HRMS (ESI pos. mode) m/z C$_{12}$H$_{20}$N$_3$O (MH$^+$) required 222.1601. Found 222.1605.

Preparation of N-(2-methylphenyl)morpholine-4-carboxamide (27)

To a stirred solution of morpholine (0.45 g, 5 mmol) in dichloromethane (5 mL) at 0° C. under nitrogen, was added o-tolyl isocyanate (0.67 g, 5 mmol) in a solution of dichloromethane (5 mL) dropwise from a pressure equalized dropping funnel. The reaction was stirred overnight and the white precipitate collected by filtration under reduced pressure (0.38 g, 38%), estimated >95% pure by NMR and thin layer chromatography. This solid was recrystallized with some difficulty from ethanol-water to give the title product 27 as colourless crystals (0.06 g, 5%); mp 160-163° C.; $^1$H (300 MHz, chloroform-d) δ 7.60 (d, J8.1=Hz, 1H), 7.20-7.10 (m, 2H), 7.00 (1H, dd, J=8 Hz), 6.10 (br. S, 1H), 3.72 (dd, J=5, 4 Hz, 4H), 3.48 (4H, dd, J=5, 4 Hz), 2.22 (s, 3H) ppm; $^{13}$C (75.5 MHz, chloroform-d) δ 155.5, 136.7, 130.4, 129.2, 126.8, 124.4, 123.1, 66.5, 44.4, 17.8 ppm; $v_{max}$ (solid) 3286, 3000, 2850, 1630, 1510, 1456, 1379, 1300, 1255, 1112, 996, 888, 744, 714, 565 cm$^{-1}$; m/z (ESI pos. mode) 243. 1, (MNa$^+$), 463.2 (M$_2$Na$^+$); HRMS (ESI pos. mode) m/z C$_{12}$H$_{16}$N$_2$NaO$_2$ (MNa$^+$) required 243.1104. Found 243.1108.

Preparation of 1-(2-methylphenyl)-3-octylthiourea (28)

General Procedure I was used with o-tolyl isothiocyanate (0.75 g, 5 mmol) and octylamine (0.65 g, 5 mmol) to give, after purification by flash column chromatography (SiO$_2$, 15:85 EtOAc: 40-60° petroleum ether) the title product 28 as a colourless oil (0.12 g, 9%); mp 95-97° C.; $^1$H NMR (300 MHz, chloroform-d) δ 7.36-7.12 (m, 5H), 5.59 (s, 1H), 3.57 (dd, J=8, 6 Hz, 2H), 2.26 (s, 3H), 1.32-1.18 (m, 10H), 0.85 (t, J=7 Hz, 3H) ppm; $^{13}$C (75.5 MHz, chloroform-d) δ 180.3, 135.3, 131.2, 128.0, 127.0, 126.9, 45.0, 28.5, 31.1, 28.6, 28.5 26.2, 22.0, 17.2, 13.5 ppm; $v_{max}$ (oil) 3157, 2953, 2925, 2849, 1536, 1504, 1456, 1282, 1249, 1214, 1175, 1152, 1115, 1086, 1036, 740, 707 cm$^{-1}$. m/z (ESI pos. mode) 279.1 (MH$^+$), 301.1 (MHNa$^+$); HRMS (ESI pos. mode) m/z C$_{16}$H$_{26}$N$_2$NaS (MNaH$^+$) required 301.1709. Found 301.1695.

Preparation of 3-[2-(dimethylamino)ethyl]-1-(2-methylphenyl)thiourea (29)

General Procedure I was used with o-tolyl isothiocyanate (0.75 g, 5 mmol) and N,N'-dimethylenediamine (0.44 g, 5 mmol) to give, after purification by flash column chromatography (SiO$_2$, 15:85 EtOAc: 40-60° petroleum ether) the title product 29 as a colourless oil (0.80 g, 67%); $^1$H NMR (300 MHz, chloroform-d) δ 7.75 (s, 1H), 7.29-7.12 (m, 4H), 6.57 (s, 1H), 3.64-3.55 (m, 2H), 2.38 (t, J=6 Hz, 2H), 2.25 (s, 3H), 2.04 (s, 6H) ppm; $^{13}$C NMR (75.5 MHz, chloroform-d) δ 181.3, 134.5, 130.6, 129.7, 127.2, 122.9, 120.1, 43.6, 40.3, 26.5, 17.4 ppm; m/z (ESI pos mode) 238.1 (M$^+$H). HRMS (ESI pos. mode) m/z C$_{12}$H$_{20}$N$_3$S (MH$^+$) required 238.1372, found 238.1362.

Preparation of N-(2-methylphenyl)morpholine-4-carbothioamide, (30)

General Procedure I was used with o-tolyl isothiocyanate (0.75 g, 5 mmol) and morpholine (0.44 g, 5 mmol) to give, after recrystallization from hot ethanol the title product 30 as white crystals (1.08 g, 92%); mp 145-147° C.; $^1$H NMR (300 MHz, chloroform-d) δ 7.26-7.03 (m, 4H), 6.95 (s, 1H), 3.81-3.64 (m, 8H), 2.24 (s, 3H) ppm; $^{13}$C (75.5 MHz, chloroform-d) δ 183.7, 138.0 131.6, 130.5, 126.3, 125.8, 124.2, 65.5, 49.0, 17.4 ppm; $v_{max}$ (oil) 3159, 2854, 1518, 1492, 1461, 1401, 1318, 1295, 1281, 1264, 1218, 1204, 1114, 1064, 1027, 942, 910, 864, 751, 719, 693 cm$^{-1}$; m/z 237.0 (MH$^+$), 259.0 (MNaH$^+$). HRMS (ESI pos. mode) m/z $C_{12}H_{16}N_2NaOS$ (MNaH$^+$) required 259.0876. Found 259.0863.

General Procedure II—Addition of Isocyanate to Bifunctional Amines

Aromatic bis-ureas and -thioureas were prepared using a previously reported method (Radi, M.; Falchi, F.; Garbelli, A.; Samuele, A.; Bernardo, V.; Paolucci, S.; Baldanti, F.; Schenone, S.; Manetti, F.; Maga, G.; Botta, M., Discovery of the first small molecule inhibitor of human DDX3X specifically designed to target the RNA binding site: Towards the next generation HIV-1 inhibitors. *Bioorg. Med. Chem. Lett.* 2012, 22 (5), 2094-2098). To a solution of the amine (1 equiv., 5 mmol) in dry dichloromethane (5 mL) under dry $N_2$ was added the isocyanate (2 equiv., 10 mmol) in dry dichloromethane (~10 mL) with stirring, and left overnight at room temperature. The precipitate was collected by filtration and washed with hot ethanol on a fluted filter paper. The resulting solid was insoluble in most solvents except dimethylformamide and dimethylsulfoxide.

Preparation of 1,1'-(1,3-phenylene)bis(3-(3-nitrophenyl) urea) (31)

Compound 31 was prepared using General Procedure II with m-phenylenediamine (540 mg, 5 mmol) and nitrophenyl isocyanate (1.64 g, 10 mmol) to produce the title compound 31 as a white-yellow solid (1.948 g, 85%); mp 289 ±1° C.; $^1$H NMR (300 MHz, DMSO-d$_6$) δ 9.15 (s, 2H), 8.93 (s, 2H), 8.60 (t, J=2 Hz, 2H), 7.88-7.75 (m, 3H), 7.57 (t, J=8 Hz, 2H) 7.20 (dd, J=9, 7 Hz 1H), 7.10 (dd, J=7, 2 Hz, 2H) ppm; $^{13}$C NMR (75 MHz, DMSO-d$_6$) δ 152.3, 148.1, 141.0, 139.7, 130.0, 129.1, 124.3, 116.2, 112.4, 112.1, 108.5 ppm; $v_{max}$ (solid) 3291, 1651, 1595, 1551 cm$^{-1}$; m/z (ESI pos. mode) 459.124 (MNa$^+$, 41%), 461.140 (MNaH$_2^+$, 100%), 463.159 (MNaH$_4^+$, 25%), 465.227 (MNaH$_6^+$, 13%). HRMS (ESI pos. mode) m/z $C_{20}H_{16}N_6NaO_6$ required 459.1024. Found 459.0812. Elemental analysis calcd for $C_{20}H_{16}N_6O_6$: C 55.05%, H 3.70%, N 19.26%. Found: C 54.31%, H 3.67%, N 19.13%.

Preparation of 1,1'-(1,3-phenylene)bis(3-(3-nitrophenyl) thiourea), (32)

General Procedure II was used with m-phenylenediamine (0.38 g, 3.5 mmol) and 3-nitrophenylisothiocyanate (1.27 g, 5 mmol) to give after recrystallisation from hot ethanol the title product as yellow crystals (0.97 g, 60%); mp 190-193° C.; $^1$H NMR (300 MHz, DMSO-d$_6$) δ 10.29-10.22 (m, 2H), 10.08 (s, 2H), 8.45 (t, J=2 Hz, 2H), 7.97-7.80 (m, 4H), 7.68 (t, J=2 Hz, 1H), 7.54 (t, J=8 Hz, 2H), 7.37 (dd, J=9, 7 Hz, 1H), 7.31-7.21 (m, 2H) ppm; $^{13}$C (75.5 MHz, DMSO-d$_6$) δ 179.5, 164.0, 147.3, 140.8, 139.1, 129.8, 129.4, 129.0, 120.0, 118.6, 117.8, ppm; $v_{max}$ (oil) 3016, 2364, 1523, 1455, 1438, 1347, 1319, 1281, 1234, 1091, 1000, 970, 935, 878, 862, 831, 787, 742, 730, 682, 665 cm$^{-1}$. HRMS (ESI pos. mode) m/z $C_{20}H_{16}N_6NaO_4S_2$ required 491.0567. Found 491.0569.

Preparation of 1,1'-(1,3-phenylene)bis(3-(3-(methylthio) phenyl)urea) (33)

Compound 33 was prepared using general procedure II with m-phenylenediamine (600 mg, 5 mmol) and 3-(methylthio)phenyl isocyanate (1.76 g, 10 mmol) to give the title compound 33 as a white powder (1.54 g, 65%); mp 305±1° C.; $^1$H NMR (300 MHz, DMSO-d$_6$) δ 8.76 (br. s, 1H), 8.66 (br. s, 1H), 7.67 (d, J=2 Hz, 1H), 7.49 (t, J=2 Hz, 1H), 7.20-7.01 (m, 5H), 6.86 (d, J=8 Hz, 1H), 5.76 (s, 4H), 2.46 (s, 6H) ppm; $^{13}$C NMR (75 MHz, DMSO-d$_6$) δ 164.0, 152.3, 140.2, 138.6, 129.2, 129.1, 119.1, 115.0, 114.6, 111.8, 107.9, 54.9 ppm; $v_{max}$ (solid) 3276, 1633, 1553, 1479, 1395, 1281, 1222, 681, 647 cm$^{-1}$; m/z (ESI pos. mode) 439.180 (MH$^+$, 12%), 461.159 (MNa$^+$, 100%); HRMS (ESI pos. mode) m/z $C_{22}H_{22}N_4NaO_2S_2$ required 461.1076. Found 461.1232. Elemental analysis calcd for $C_{22}H_{22}N_4O_2S_2$: C 60.25%, H 5.06%, N 12.78%. Found: C 60.10%, H 5.02%, N 12.77%.

Preparation of 1,1'-(1,3-phenylene)bis(3-(3-methoxyphenyl)urea) (34).

Compound 34 was prepared using general procedure II using m-phenylenediamine (541 mg, 5 mmol) and 3-methoxyphenylisocyanate (1.49 g, 10 mmol) to produce the title compound 34 as a white solid (440 mg, 22%); mp 294-297° C.; $^1$H NMR (300 MHz, DMSO-d$_6$) δ 8.61 (s, 2H), 8.41 (s, 2H), 7.62 (t, J=2 Hz, 1H), 7.35 (d, J=7 Hz, 4H), 7.12 (m, 1H), 7.00 (d, J=7 Hz, 1H), 6.86 (d, J=7 Hz, 4H), 3.71 (s, 6H) ppm; $^{13}$C NMR (75 MHz, DMSO-d$_6$) δ 163.8 154.4, 129.0, 119.9, 113.9, 111.4, 55.1 ppm; $v_{max}$ (solid) 3305, 1639, 1599, 1562, 1512, 1493, 1300, 1242, 1035, 879, 648 cm$^{-1}$; m/z (ESI pos. mode) 429.214 (MNa$^+$, 100%); HRMS (ESI pos. mode) m/z $C_{22}H_{22}N_4NaO_4$ required 429.1533. Found 429.1669. Elemental analysis calcd for $C_{22}H_{22}N_4O_4$: C 65.01%, H 5.46%, N 14.78%. Found: C 64.71%, H 5.56%, N 14.78%.

Preparation of 1-(2-nitrophenyl)-3-(3-{2-[2-(3-{[(2-nitrophenyl)carbamoyl]amino}-propoxy)ethoxy]ethoxy}propyl) urea (35)

To a stirred solution of 4,7,10-trioxa-1,13-tridecanediamine (0.82 g, 10 mmol) in dichloromethane (10 mL) at 0° C. under nitrogen was added a solution of 3-nitrophenyl isocyanate (3.28 g, 20 mmol) in dichloromethane (10 mL) from a pressure equalized dropping funnel. The reaction was stirred overnight and the crude product was isolated a by removal of volatiles on a rotary evaporator in an efficient fumehood. Purification by flash column chromatography (SiO$_2$, 1% MeOH-EtOAC gave the title product 35 as a white solid (3.703 g, 68%) mp 99-101° C.; $^1$H (300 MHz, DMSO-d$_6$) δ 9.00 (s, 1H), 8.50 (t, J=2 Hz, 1H), 7.72 (dd, J=7, 1 Hz, 1H), 7.52 (dd, J8, 1=Hz, 1H), 7.49 (t, J=8 Hz, 1H), 6.32 (t, J=6 Hz, 1H), 3.60-3.50 (m, 4H), 3.48 (m, 4H), 3.15 (q, J=7 Hz, 2H), 1.70 (q, J=7 Hz, 2H) ppm; $^{13}$C (75.5 MHz, DMSO-d$_6$) δ 154.9, 148.1, 141.9, 129.8, 123.6, 123.6, 115.3, 111.4, 69.7, 69.5, 68.1, 36.6, 29.8 ppm; $v_{max}$ (solid) 3326, 3300, 2950, 2900, 1634, 1553, 1481, 1347, 1259, 1102, 968, 874, 832, 801, 728, 690, 640 cm$^{-1}$; m/z (ESI pos. mode) 571.1 (MNa$^+$); ESI (neg. mode) 547.1 (M-H)$^-$, 583.1 (M$^{35}$Cl)$^-$, 585.1 (M$^{37}$Cl)$^-$. HRMS (ESI pos. mode) m/z $C_{24}H_{33}N_6O_9$ (MNa$^+$) required 549.2304, found 549.2309.

Preparation of 1-[3-(methylsulfanyl)phenyl]-3-[3-(2-{2-[3-({[3-(methylsulfanyl)-phenyl]carbamoyl}amino)propoxy]ethoxy}ethoxy)propyl]urea, (36)

To a solution of 4,7,10-trioxa-1,13-tridecanediamine (1.13 g, 5.1 mmol) in dichloromethane (10 mL) at 0° C. was added dropwise 3-(methylthio)phenyl isocyanate (1.67 g, 10.1 mmol) in dichloromethane (10 mL). The solution was allowed to warm to room temperature and stirred for 3 hrs, then evaporated under reduced pressure. The reaction mixture was purified by flash column chromatography (SiO$_2$, 5:95 MeOH:EtOAc) to give the title product 36 as a white solid (1.91 g, 3.47 mmol, 68.7%); mp 106-108° C.; $^1$H NMR (300 MHz, CDCl$_3$) δ 7.40 (t, J=2 Hz, 2H), 7.33 (s, 2H), 7.15 (t, J=8 Hz, 2H), 7.05 (dd, J=7, 2 Hz, 2H), 6.84 (dd, J=8, 1 Hz, 2H), 5.62 (t, J=6 Hz, 2H), 3.70-3.65 (m, 4H), 3.63-3.58 (m, 4H), 3.57 (m, 4H), 3.30 (quartet, J=6 Hz, 4H), 2.42 (s, 6H), 1.73 (quintet, J=6 Hz, 4H);$^{13}$C NMR (101 MHz, CDCl$_3$) δ 156.1, 140.2, 139.3, 129.2, 120.4, 116.7, 115.7, 70.3, 69.9, 69.3, 38.4, 28.9, 15.6 ppm; $v_{max}$ (solid)

3303, 2865, 1628, 1562, 1481, 1117, 613 cm$^{-1}$; m/z (ESI pos. mode) 573.1 (MNa$^+$); Elemental analysis calcd for $C_{26}H_{38}N_4O_5S_2$: C 56.70% H 6.69% N 10.17%. Found: C 56.70% H 6.70% N 10.20%.

Preparation of 1-[4-(methylsulfanyl)phenyl]-3-[3-(2-{2-[3-({[4-(methylsulfanyl)-phenyl]carbamoyl}amino)propoxy]ethoxy}ethoxy)propyl]urea, (37)

To a solution of 4,7,10-trioxa-1,13-tridecanediamine (1.23 g, 5.58 mmol) in dichloromethane (10 mL) at 0° C. was added dropwise a solution of 4-(methylthio)phenyl isocyanate (1.68 g, 10.2 mmol) in dichloromethane (10 mL). The solution was allowed to warm to room temperature and stirred for 24 hrs, then evaporated under reduced pressure. The reaction mixture was purified by flash column chromatography (SiO$_2$, 10:90 MeOH:EtOAc), followed by recrystallization from hot ethanol to give the title product 37 as a white solid (0.464 g, 0.84 mmol, 16.5%); mp 137-139° C.; $^1$H NMR (400 MHz, CDCl$_3$) δ 7.32 (d, J=9 Hz, 4H), 7.22-7.18 (br. s, 2H), 7.20 (d, J=9 Hz, 4H), 5.55 (s, 2H), 3.73-3.68 (m, 4H), 3.65-3.62 (m, 4H), 3.60 (t, J=6 Hz, 4H), 3.35 (quartet, J=6 Hz, 4H), 2.44 (s, 6H), 1.76 (quintet, J=6 Hz, 4H) ppm; $^{13}$C NMR (101 MHz, CDCl$_3$) δ 156.1, 137.4, 131.2, 128.7, 120.0, 70.3, 69.9, 69.2, 38.5, 28.9, 17.2 ppm; v$_{max}$ (solid) 3299, 2868, 1634, 1594, 1558, 1136, 817, 506 cm$^{-1}$; m/z (ESI pos. mode) 573.1 (MNa$^+$). Elemental analysis calcd for $C_{26}H_{38}N_4O_5S_2$ C 56.70% H 6.96% N 10.17%. Found C 56.30% H 6.92% N 10.13%.

Preparation of 1-(2-methylphenyl)-3-(3-{2-[2-(3-{[(2-methylphenyl)carbamoyl]-amino}propoxy)ethoxy]ethoxy}propyl)urea, (38)

To a solution of 4,7,10-trioxa-1,13-tridecanediamine (1.12 g, 5.08 mmol) in dichloromethane (10 mL) at 0° C., was added dropwise a solution of o-tolyl isocyanate (1.45 g, 10.9 mmol) in dichloromethane (10 mL). The solution was allowed to warm to room temperature and stirred for 24 hrs, then evaporated under reduced pressure. The reaction mixture was then purified by flash column chromatography (SiO$_2$, 10:90 MeOH:EtOAc) to give the title product 38 as a white solid (1.83 g, 3.76 mmol, 74.0%); mp 78-82° C.; $^1$H NMR (400 MHz, CDCl$_3$) δ 7.53 (d, J=8 Hz, 2H), 7.16 (t, J=7 Hz, 4H), 7.02 (t, J=6 Hz, 2H), 6.40 (s, NH, 2H), 5.41 (t, J=6 Hz, NH, 2H), 3.60-3.51 (m, 12H), 3.32 (quartet, J=6 Hz, 4H), 2.24 (s, 6H), 1.73 (quintet, J=6 Hz, 4H) ppm; $^{13}$C NMR (101 MHz, CDCl$_3$) δ 156.7, 136.9, 130.6, 126.7, 124.5, 124.0, 70.4, 69.7, 69.5, 38.1, 29.5, 17.9 ppm; v$_{max}$ (solid) 3306.5, 1629.4, 1561.9, 1243.0, 1104.4, 753.3, 652.2 cm$^{-1}$. m/z (ESI pos mode) 509.2 (MNa$^+$). Elemental analysis calcd for $C_{26}H_{38}N_4O_5$ C 64.16% H 7.88% N 11.52%. Found C 64.03% H 7.88% N 11.48%.

Preparation of 1-(3-chlorophenyl)-3-(o-tolyl)urea, (39)

o-Toluidine and 3-chlorophenylisocyanate were combined using General Procedure I on a 5 mmol scale to give, after recrystallization from ethanol, the title product 39 (1.02 g, 78%); mp 201-202° C.; $^1$H NMR (300 MHz, DMSO-d$_6$) δ 9.21(s, 1H), 7.99 (s, 1H), 7.80 (d, J=8 Hz, 1H), 7.76-7.72 (m, 1H), 7.34-7.09 (m, 4H), 7.04-6.92 (m, 2H), 2.24 (s, 3H) ppm; $^{13}$C NMR (75 MHz, DMSO): δ 164.0, 152.5, 141.4, 137.0, 133.2, 130.4, 130.2, 127.9, 126.1, 123.0, 121.3, 117.3, 116.4, 17.8 ppm; v$_{max}$ (solid) 3287, 1633, 1585, 1546, 1480, 1457, 1269, 1259, 1235, 760 cm$^{-1}$; m/z $C_{14}H_{13}ClN_2O$ (ESI pos. mode) Calcd for [MNa]$^+$=283.06 Found: 283.0.

Preparation of 1-(o-tolyl)-3-(3-(trifluoromethyl)phenyl)urea, (40)

o-Toluidine and 3-trifluoromethylphenylisocyanate were combined using General Procedure I on a 5 mmol scale to give, after recrystallization from ethanol, the title product 40 (1.27 g, 86%); mp 185° C.; $^1$H NMR (300 MHz, DMSO): δ 9.37(s, 1H), 8.03 (s, 2H), 7.78 (d, J=8 Hz, 1H), 7.60-7.48 (m, 2H), 7.31 (d, J=7 Hz, 1H), 7.22-7.08 (m, 2H), 6.97 (t, J=8 Hz, 1H), 2.25 (s, 3H) ppm; $^{13}$C NMR (75 MHz, DMSO): δ 164.0, 152.6, 140.7, 136.9, 130.2, 129.9, 129.7, 129.3, 128.1, 126.1, 123.1, 121.5, 117.9, 113.8, 17.8 ppm; v$_{max}$(solid) 3298, 1637, 1560, 1331, 1155, 1124, 1067 cm$^{-1}$; m/z $C_{15}H_{13}F_3N_2O$ (ESI pos. mode) Calcd for [MNa]$^+$=317.09 Found: 317.1.

Preparation of 1-(4-bromophenyl)-3-(o-tolyl)urea (41)

o-Toluidine and 3-bromophenylisocyanate were combined using General Procedure I on a 5 mmol scale to give, after recrystallization from ethanol, the title product 41 (1.19 g, 78%); mp 240° C.; $^1$H NMR (300 MHz, DMSO): δ 9.14(s, 1H), 7.95 (s, 1H), 7.81 (d, J=8 Hz, 1H), 7.44 (s, 4H), 7.21-7.09 (m, 2H), 6.95 (t, J=8 Hz, 1H), 2.23 (s, 3H) ppm; $^{13}$C NMR (75 MHz, DMSO): δ 164.1, 152.5, 139.3, 137.1, 131.5, 130.2, 127.7, 126.1, 122.9, 121.2, 119.9, 113.0, 17.8 ppm; v$_{max}$(solid) 3288, 1637, 1584, 1546, 1478, 1457, 1238, 1071, 1009, 835, 796 cm$^{-1}$; m/z $C_{14}H_{13}BrN_2O$ (ESI pos. mode) Calcd for [MNa]$^+$=329.01 Found: 329.0.

Preparation of 1-(o-tolyl)-3-(4-((trifluoromethyl)thio)phenyl)urea (42)

o-Toluidine and 4-thiotrifluoromethylphenylisocyanate were combined using General Procedure I on a 5 mmol scale to give, after recrystallization from ethanol, the title product 42 (1.24 g, 76%) mp 222-224° C.; $^1$H NMR (300 MHz, DMSO): δ 9.39(s, 1H), 8.05 (s, 1H), 7.81 (d, J=8 Hz, 1H), 7.62 (s, 4H), 7.21-7.11 (m, 2H), 6.97 (m, 1H), 2.24 (s, 3H) ppm; $^{13}$C NMR (75 MHz, DMSO): δ 164.0, 152.3, 143.1, 137.5, 136.9, 131.7, 130.2, 128.0, 126.2, 123.1, 121.4, 119.1, 118.7, 113.7, 17.8 ppm; v$_{max}$ (solid) 3349, 3251, 3180, 3115, 3069, 1655, 1587, 1540, 1489, 1452, 1148, 1107, 1086 cm$^{-1}$; m/z $C_{15}H_{13}F_3N_2OS$ (ESI pos. mode) Calcd for [MNa]$^+$=349.06 Found: 349.1.

Preparation of 1-(o-tolyl)-3-(4-(trifluoromethoxy)phenyl)urea (43)

o-Toluidine and 4-trifluoromethoxyphenylisocyanate were combined using General Procedure I on a 5 mmol scale to give, after recrystallization from ethanol, the title product 43 (1.10 g, 71%); mp 190-191° C.; $^1$H NMR (300 MHz, DMSO): δ 9.21(s, 1H), 7.97 (s, 1H), 7.81 (d, J=8 Hz, 1H), 7.59-7.50 (m, 2H), 7.30 (d, J=9 Hz, 2H), 7.20-7.10 (m, 2H), 7.00-6.91 (m,1H), 2.24 (s, 3H) ppm; $^{13}$C NMR (75 MHz, DMSO): δ 164.1, 164.1, 154.41, 152.6, 139.1, 137.1, 130.2, 128.7, 127.8, 126.2, 122.9, 121.8, 121.2, 119.1, 17.8 ppm; v$_{max}$ (solid): 3279, 1640, 1551, 1263, 1202, 1152 cm$^{-1}$; m/z $C_{15}H_{13}F_3N_2O_2$ (ESI pos. mode) Calcd for [MNa]$^+$=333.08 Found: 333.1.

Preparation of 1-(4-iodophenyl)-3-(o-tolyl)urea (44)

o-Toluidine and 4-iodophenylisocyanate were combined using General Procedure I on a 5 mmol scale to give, after recrystallization from ethanol, the title product 44 (1.43 g, 81%); mp 240-242° C.; $^1$H NMR (300 MHz, DMSO): δ 9.12(s, 1H), 7.94 (s, 1H), 7.81 (d, J=8 Hz, 1H), 7.63-7.56 (m, 2H), 7.35-7.28 (m, 2H), 7.21-7.09 (m, 2H), 6.99-6.91 (m, 1H), 2.23 (s, 3H) ppm; $^{13}$C NMR (75 MHz, DMSO): δ 164.3, 152.4, 139.7, 137.3, 137.1, 130.2, 127.7, 126.1, 122.8, 121.1, 120.2, 17.8 ppm; v$_{max}$ (solid) 3275, 1637, 1583, 1548, 1280, 1239, 1006, 833 cm$^{-1}$; m/z $C_{14}H_{13}IN_2O$ (ESI pos. mode) Calcd for [MNa]$^+$=375.0 Found: 375.0

Preparation of 1-(3,4-dimethoxyphenyl)-3-(o-tolyl)urea (45).

o-Toluidine and 4-iodophenylisocyanate were combined using General Procedure I on a 5 mmol scale to give, after recrystallization from ethanol, the title product 45 (1.24 g, 87%); mp 192-194° C.; $^1$H NMR (300 MHz, DMSO): δ 8.87 (s, 1H), 7.87-7.79 (m, 2H), 7.21-7.08 (m, 3H), 6.97-6.83 (m, 3H), 3.76 (s, 3H), 3.72 (s, 3H), 2.23 (s, 3H) ppm; $^{13}$C NMR (75 MHz, DMSO): δ 164.3, 152.7, 148.8, 143.8, 137.5, 133.5, 130.1, 127.2, 126.1, 122.4, 120.8, 112.5, 109.7, 103.5, 55.8, 17.8 ppm; $v_{max}$(neat) 3296, 1631, 1549, 1512, 1269, 1230, 1137, 1025 cm$^{-1}$; MS: m/z $C_{16}H_{18}IN_2O_3$ (ESI pos. mode) Calcd for [MNa]$^+$=309.12 Found: 309.1.

Example: Plaque inhibition assay

Viruses

An identical assay procedure was carried out for hRSV (strain A2) bovine RS (strain Snook) and PVM (strain 15). Virus stocks were diluted 10 fold in GMEM (Invitrogen) so that the wells containing cells received sufficient virus to generate approximately 2000, 200 and 20 plaques per well.

Growth Medium

GMEM plus 10% FCS (Biosera), penicillin (4 units/nil) and streptomycin (4 μg/ml) (Invitrogen), 3 mM glutamine (Invitrogen).

Overlay Medium

GMEM containing 2% (v/v) FCS, 1% (w/v) carboxymethylellulose (CMC) (Sigma), penicillin (4 units/nil), streptomycin (4 μg/ml), 3 mM glutamine.

The overlay medium also contained the compound to be tested at appropriate concentrations. Typically the 6 concentrations of the test compounds used were: 100 μM, 31.6 μM, 10 μM, 3.16 μM, 1 μM and 0.316 μM.

Test Compounds

Stocks of the test compounds were prepared in DMSO (Sigma) (carrier). Each stock compound was diluted 1 in 200 in overlay medium to give dilutions stated above.

Plaque Assay

Cells of a standard cell line known to support pneumovirus replication (typically HEp2 or BSC1 cells) were grown in standard 12 well plates at 37° C. in an atmosphere of 5% (v/v) CO$_2$ until confluent. Medium was aspirated from the cells and replaced with 200 μl aliquots of virus. Aliquots were prepared by diluting virus stocks 10-fold in GMEM (Invitrogen) as described above with no FCS. A mock (no virus) was also set up to test cell viability. The virus was incubated with the cells for 1 hour at 33° C. with gentle rocking every 5-10 minutes. The inocula were removed and 2 ml of overlay medium was added. Overlay medium was either test (plus compound) or control (medium alone or medium containing DMSO). The plates were incubated at 33° C. for 4-8 days to allow plaques to develop as indicated. A volume of 1 ml of additional overlay medium (containing the test compound as appropriate) was added every 3 days. All virus dilutions were carried out with each concentration of test compound, or treated as controls, and each was carried out in triplicate.

Following incubation, cells were fixed by addition of an equal volume of 4% (v/v) glutaraldehyde (Sigma) in PBS with further incubation for a minimum of 2 hours. The fixing solution was washed off under a slow flowing stream of water and 1 ml of crystal violet (0.075% w/v: Sigma) was added and left for 20 minutes at room temperature. The crystal violet was removed and the fixed cell monolayers washed. Plates were air dried. Plaques counts were recorded from wells with >20 and <200 in number. These numbers provide the most robust statistical reliability for viable plaque counts.

This experimental approach screens the ability of compounds to block the formation of plaques. A lower number of plaques than the DMSO carrier control shows that the compound is inhibiting virus growth.

96 Well Plate TCID$_{50}$

This method provides a rapid approach to initially screen compounds and was developed as an increased number of compounds were synthesised. Cells of a standard cell line known to support pneumovirus replication (typically HEp2 or BSC1 cells) were grown to 95% confluence in a 96 well plate. Virus was then added over 5 different half log dilutions starting at a multiplicity of infection of 0.02 plus mock control. Three dilutions of compound plus a DMSO control were screened per plate. Cells were fixed once the highest dilution of virus showed signification destruction or cell death in the DMSO control. Identical plate repeats for each compound dilution were fixed in subsequent days as indicated.

Stained plates were read at 595 nM, higher optical density (OD) readings indicate more viable cells remain. Therefore this application not only shows if virus growth is blocked but if the compound is detrimental to cells (reading the mock control).

Compound 1

FIG. 1 shows two biological replicates carried out on different occasions for compound 1 using HEp2 cells.

We observed that plaques that were present in the treated wells at concentrations of compound 1 above 1 μM were smaller than in the DMSO control. The level of inhibition seen between the repeats clearly differs between the repeats. This may be because the plaques that counted are only just developing, making biological variables more pronounced. Both assays were stopped after 5 days but a small difference in host cell viability can delay viral growth and give the observed results. Compound 1 is relatively insoluble and a concentration between 5-10 μM represents an upper limit, consistent with no increase in activity seen at >10 μM in the TCID50 assay. Note the required quantity of 1 gave the appearance of insolublity in cell medium at 100 μM and a virus inhibition experiment was not performed.

Following these initial results, further plaque assays were carried out with compounds 3, 4, 6, 35, 37, 39 and 40.

Compound 3

Figure 2:
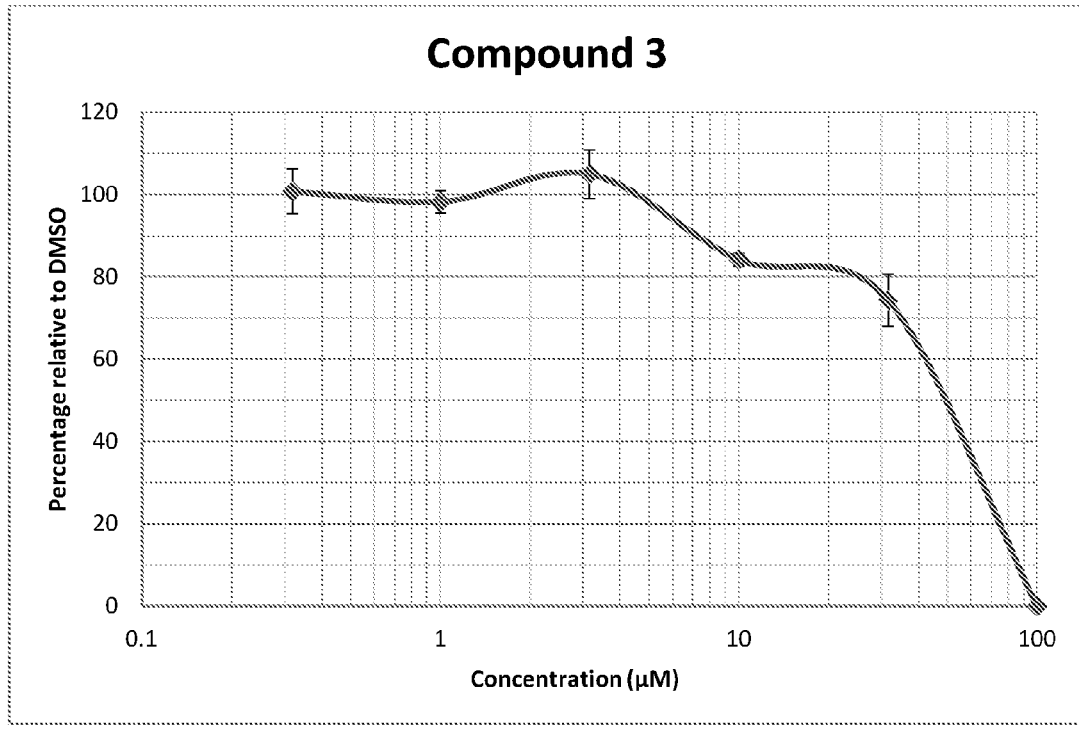
FIG. 2 shows the effect of 3 on plaque size (relative to a DMSO control) after 5 days.

FIG. 2 shows the effect of 3 on plaque size (relative to a DMSO control) after 5 days using HEp2 cells. Where plaques were present, their size was much smaller than those seen with the DMSO control. In particular, plaques observed at 31.6 μM and to some extent 10 μM were very small.

As before, the total number of plaques counted from 6 different wells in the presence of DMSO alone was set at 100% (standard deviation of the mean of DMSO control 5.4%). Plaques counted in the presence of 3 at the concentrations indicated are given as a percentage of the DMSO control. The IC$_{50}$ was estimated to be 50 μM, although further experiments at concentrations of 30-80 μM are required to confirm this.

Compound 4

Figure 3:
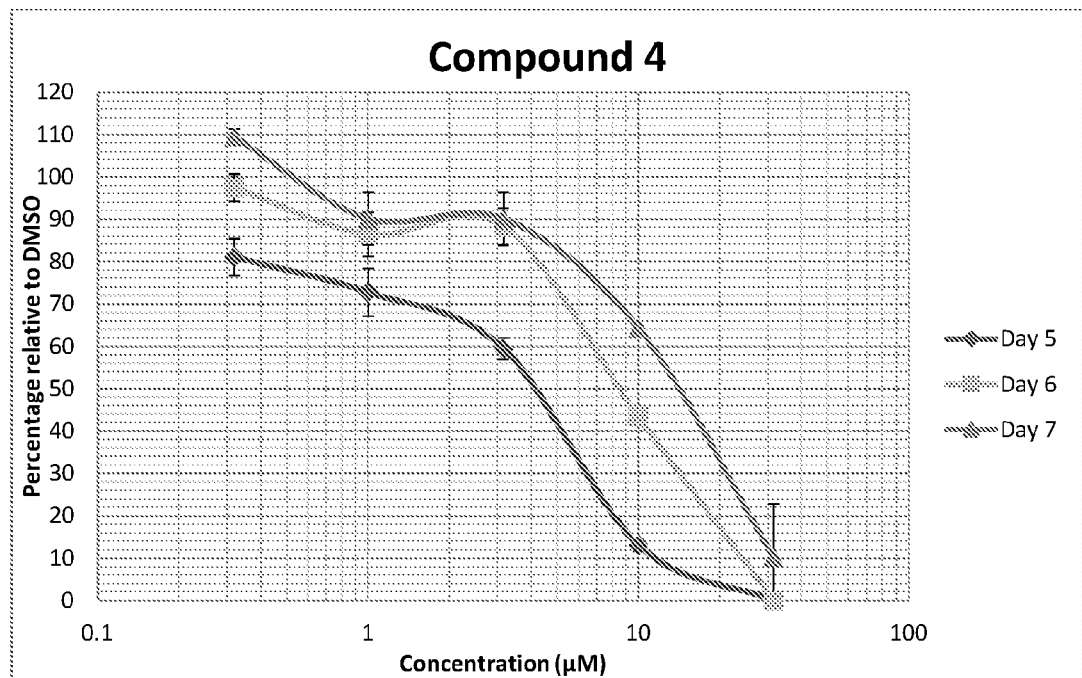
FIG. 3 shows the results of further tests carried out to screen inhibition over a number of days for compound 4.

It was hypothesised that these compounds are delaying plaque formation, so that, at lower dilutions, virus plaques will appear. Further tests using HEp2 cells were carried out to screen inhibition over a number of days for compound 4. The results are shown in FIG. 3. This confirmed the delayed plaque formation hypothesis.

IC$_{50}$ values were calculated as 4.1 μM (Day 5), 8.5 μM (Day 6), and 15 μM (Day 7). Thus, the data show an increasing IC$_{50}$ value with time of incubation of the assay, as expected. This emphasises that the compound does not inhibit virus replication completely, but significantly limits it. This is consistent with our understanding of the role of the M2-2 protein in the virus replication cycle.

Compound 4 showed toxicity at 100 μM and to some degree at 31.6 μM. No obvious toxicity was seen at 10 μM, although this concentration was also less effective.

Compound 6

Figure 4:
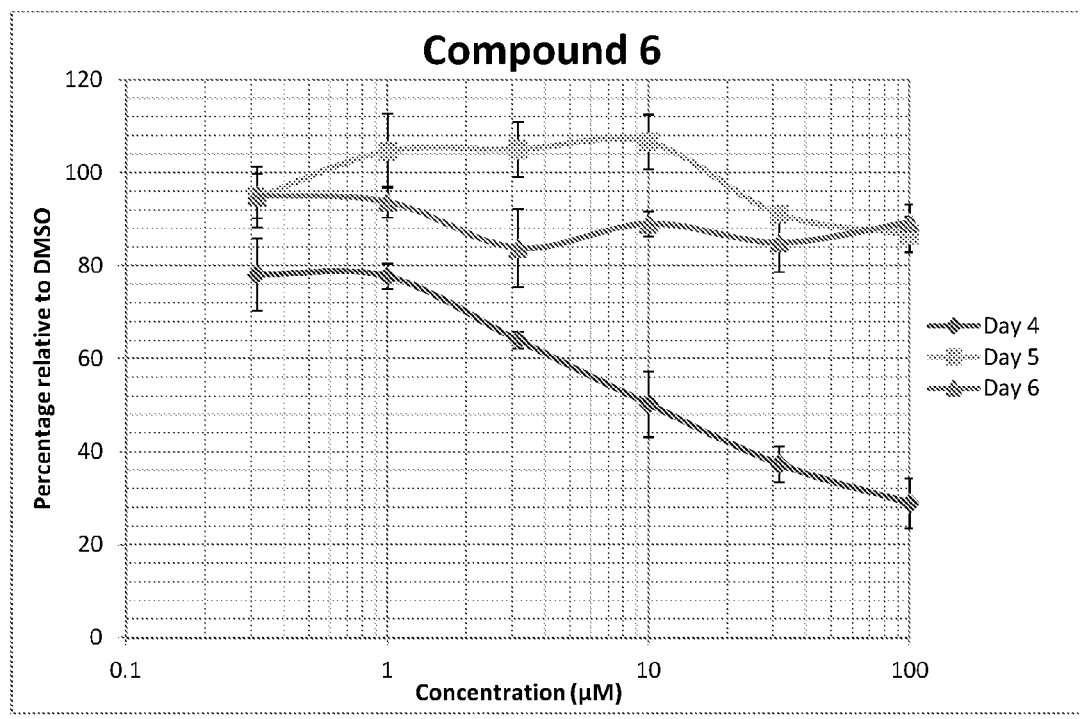
FIG. 4 shows results for compound 6 tested using assays stopped after 5, 6 and 7 days.

This compound was tested using assays stopped after 5, 6 and 7 days using HEp2 cells. The results are shown in FIG. 4. The $IC_{50}$ on day 5 was 10 µM. A 50% reduction was not reached on days 6 and 7

Compound 35

Figure 5:
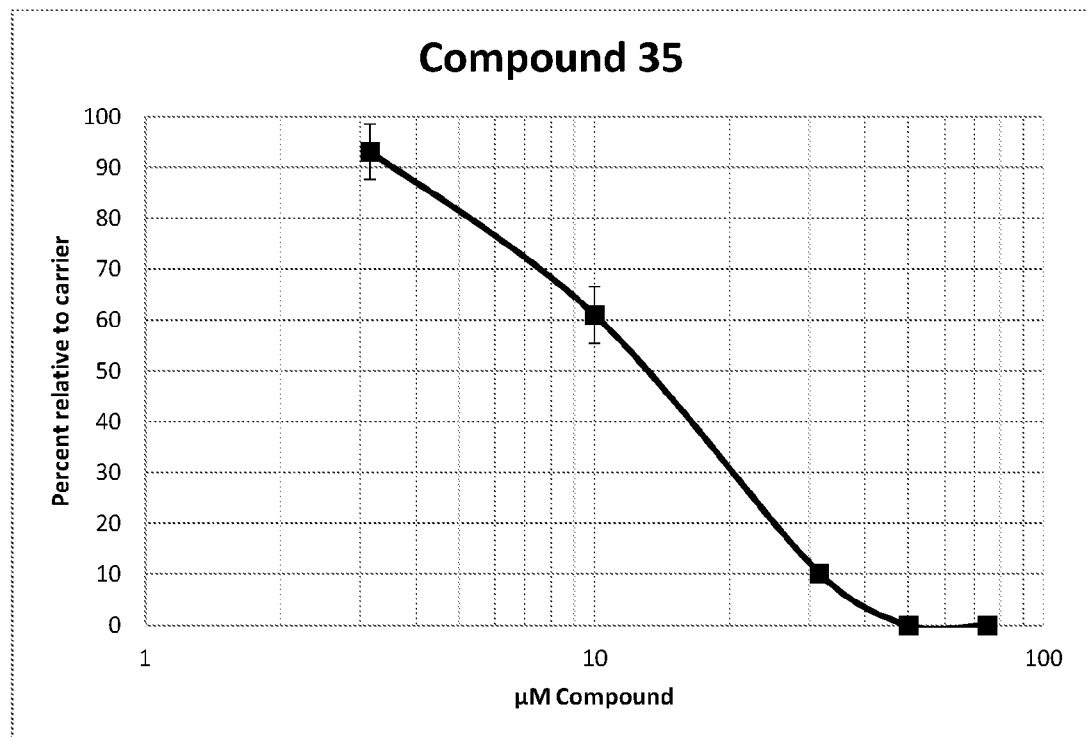
FIG. 5 shows results for compound 35 tested in a 5 day assay.

This compound was tested in a 5 day assay using HEp2 cells. The results are shown in FIG. 5. The $IC_{50}$ was 12.5 µM. At 100 µM, compound 35 showed toxicity and showed some signs of precipitating out of solution. Subsequent dilutions also showed a reduction in plaque numbers (as shown) and size.

Compound 37

This compound was tested in a 5 day assay using HEp2 cells. The $IC_{50}$ was 17.5 µM. At 100 µM, compound 37 showed toxicity and showed some signs of precipitating out of solution.

Compound 39

Figure 6:
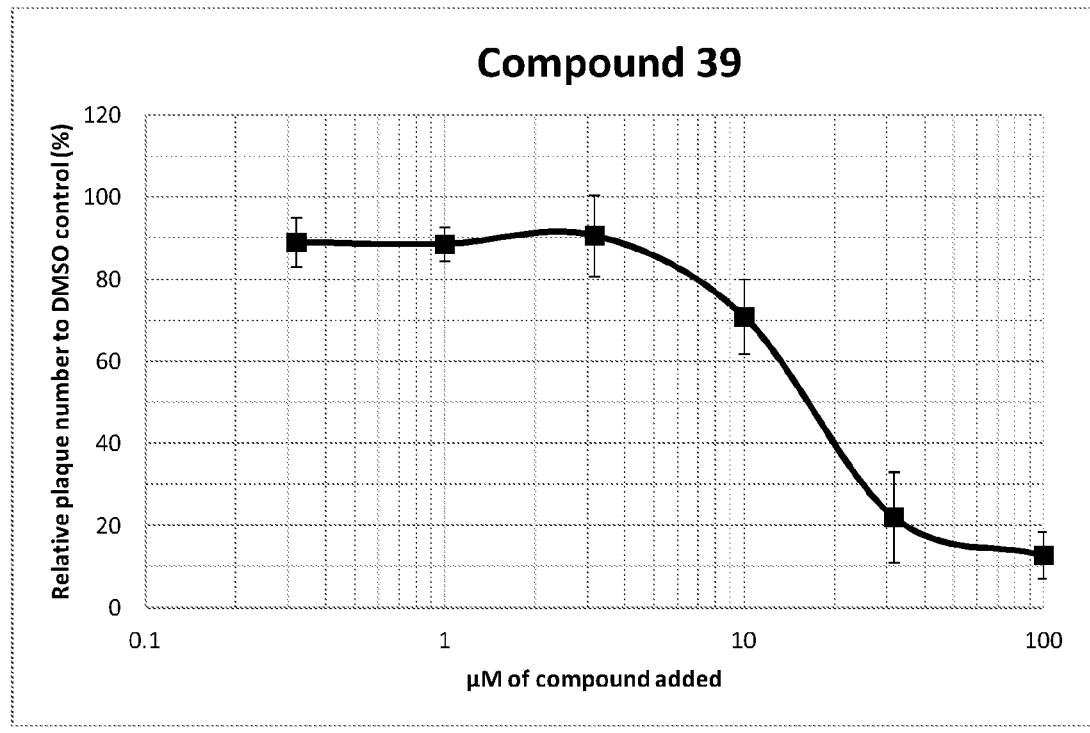
FIG. 6 shows results for compound 39 tested in a 4 day assay using BSC1 cells.

This compound was tested in a 4 day assay using BSC1 cells. The results are shown in FIG. 6. The $IC_{50}$ was 16.5 µM. At 100 µM, compound 39 showed some toxicity and was moderately soluble in cell medium. Subsequent dilutions also showed a reduction in plaque numbers (as shown) and size.

Compound 40

Figure 7:
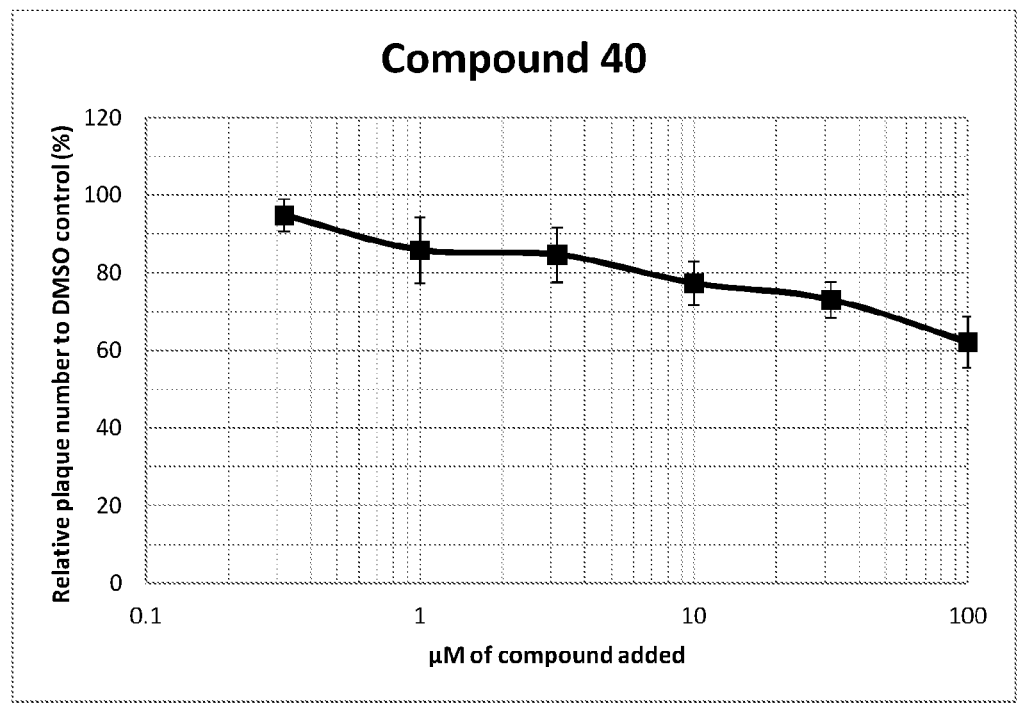
FIG. 7 shows results for compound 40 tested in a 4 day assay using BSC1 cells.

This compound was tested in a 4 day assay using BSC1 cells. The results are shown in FIG. 7. This compound showed moderate inhibition of plaque formation. At 100 µM, compound 40 showed low toxicity.

Example: Activity Against Other Pneumoviruses

Compounds 1, 4 and 6 were also tested against bovine RSV and pneumonia virus of mice (PVM).

Bovine RSV

Figure 8:
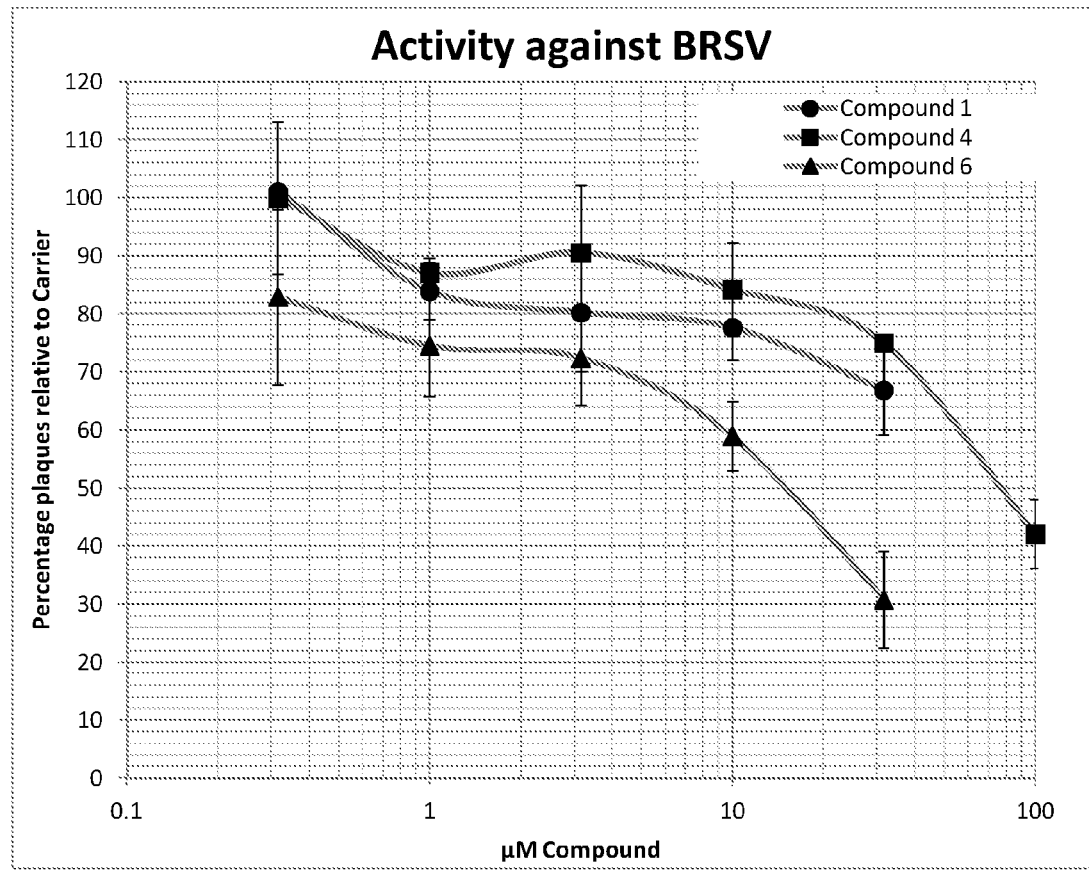
FIG. 8 shows results for compounds 1, 4 and 6 tested against Bovine RSV with a 6-day assay.

The compounds were tested with a 6-day assay using HEp2 cells. The results are shown in FIG. 8. $IC_{50}$ values of 80 µM (compound 4) and 15 µM (compound 6) were calculated. Compound 1 again precipitated out before 50% reduction was seen.

Pneumonia Virus of Mice (PVM)

Figure 9:
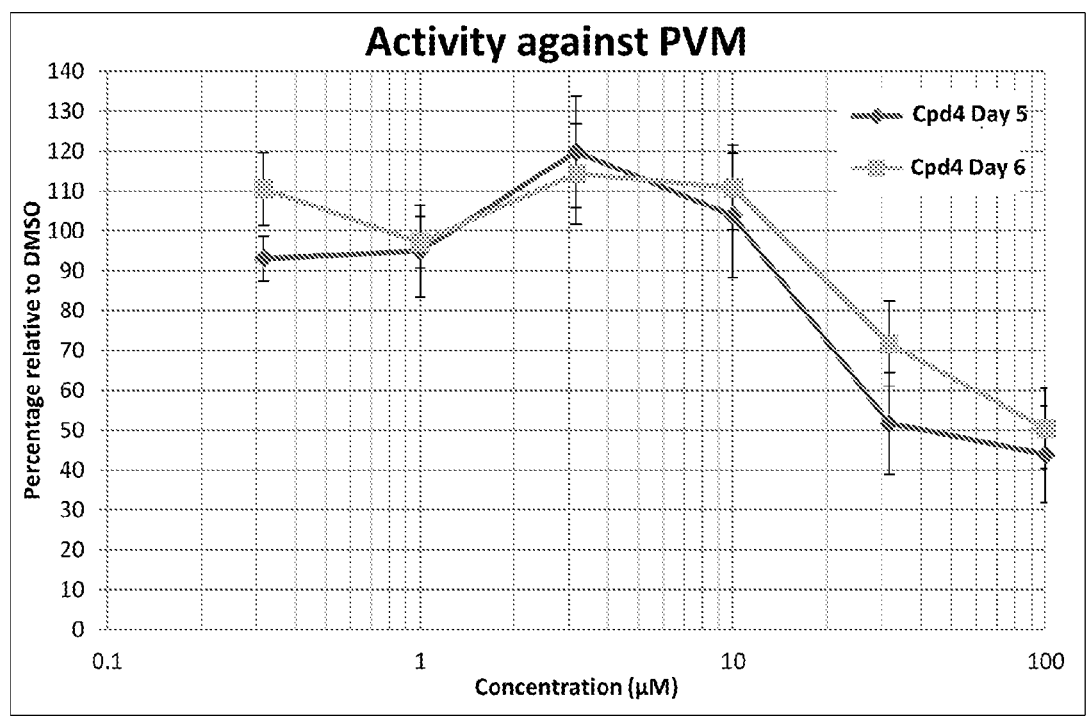
FIG. 9 shows results of a full plaque assay carried out for compound 4, tested against PVM with assays of 5 days and 6 days after incubation.

A full plaque assay was carried out for compound 4 using HEp2 cells, with assays of 5 days and 6 days after incubation. The results are shown in FIG. 9. $IC_{50}$ values of 32 µM (day 5) and 100 µM (day 6) were obtained. Compounds 1 and 6 were not tested fully, but appear to have similar $IC_{50}$ values to compound 4 for the dilutions tested.

The compounds (1, 4, 6 and 35) also significantly reduce the size of plaques of hRSV, bRSV and PVM. These smaller size plaques are still counted in the assay, but indicate a significant reduction in virus replication and spread.

Example: Effect on Virus Yield

The initial studies on compounds assessed their ability to reduce the number of plaques detected in a conventional plaque assay. When the plaques were observed it was noted that the plaque size was significantly reduced in the presence of some compounds. These data suggested that the compounds reduced the amount of virus produced from infected cells and hence slowed the rate of plaque development. A reduction in virus yield is a desirable attribute for antiviral compounds and this was therefore tested directly.

A cell monolayer was infected at a low multiplicity of infection (a small amount of virus relative to the total number of cells) such that only a few cells were infected. CMC was not added to the overlay medium, so that virus particles released from cells could spread throughout the dish and infect new cells. If left, this process will continue until eventually the whole cell monolayer is destroyed. The supernatant which contains the released virus from cells can be collected and the virus titre can be measured using a standard plaque assay. This gives an indication of released (circulating) virus.

The compounds were therefore tested to determine whether they affected the amount of infection virus particles released into the supernatant.

Method

A monolayer of cells of a standard cell line known to support pneumovirus replication (typically HEp2 or BSC1 cells) were infected at a moi of 0.02 for an hour at 33° C. in 200 µl of medium lacking serum. The inoculum was removed and 2 ml of overlay medium (GMEM 2% FCS) was added with either carrier or compounds as indicated. After a designated period, 1.5 ml of supernatant was carefully collected without disturbing the cells and stored at −80° C. Individual plates were used for each time point. The virus titre in the medium was calculated by carrying out a standard plaque assay with the exception of the following change. During the initial 1 hour step where the virus is first added to the cells the volume of inoculum added was 2 ml instead of 200 µl. Thus the supernatant was diluted at least 1 in 20 taking the final concentration of any compound present to a level below its active range. Following virus adsorption period (1 hour) the inoculum was removed and replaced with 2% CMC overlay medium (without compounds).

Figure 10:
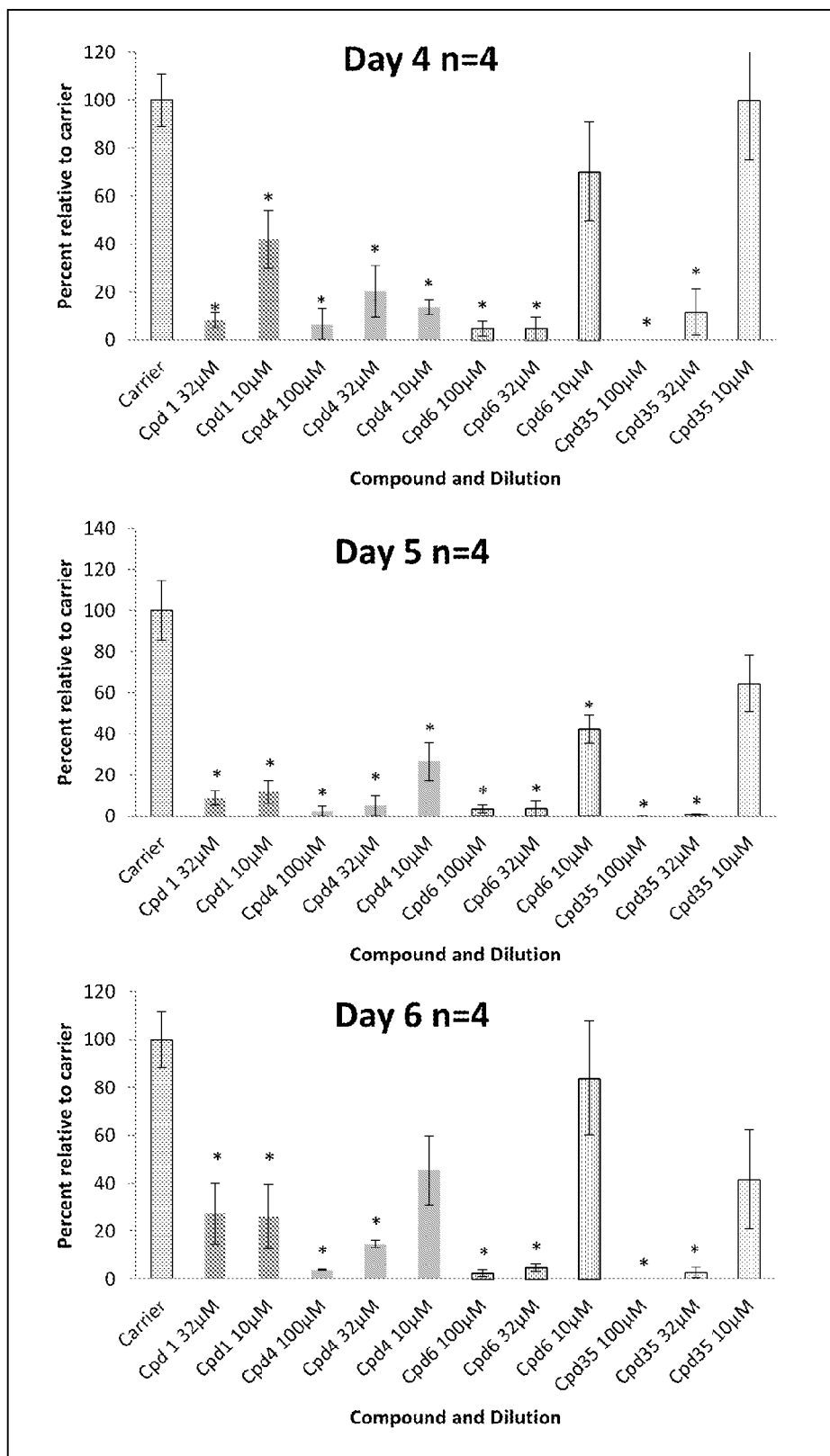
FIG. 10 shows the yield of virus from cells treated with compounds 1, 4, 6 and 35 at the various concentrations as shown.

Four compounds were tested. Compound 1 was tested at concentrations of 32 µM and 10 µM. Compounds 4, 6 and 35 were each tested at 100 µM, 32 µM and 10 µM. The carrier DMSO alone was used as a control. Supernatants were collected on day 4, day 5 and day 6 post infection. Data were processed by establishing the yield of virus in cells treated with DMSO carrier alone. This was set at 100% and the yield of virus from cells treated with the four compounds at the various concentrations were calculated relative to this value. The data are shown in FIG. 10.

Conclusion

The data show a clear dose-dependent effect of all four compounds with yield of virus reduced as the concentration increased. All compounds show a statistically significant reduction in released virus at 32 µM ($p<0.05$, compared to the carrier treated control, assessed using a Mann-Witney test and indicated by an asterisk in FIG. 10). It is anticipated that in infected animals this reduction in virus production would give the immune system an advantage in combating infection and reducing clinical disease while allowing the establishment of long-term protective immune memory. Compound 35 at 100µM appears to be the most active compound with no released virus detected when infected cells were treated with 100 µM of compound. This represents a reduction in virus yield of at least $2.3 \times 10^3$-fold. However a high level of cellular toxicity of this compound was noted at this dilution.

These results indicate that the compounds tested which are designed to inhibit the cellular DDX3X protein slow down virus replication considerably in a dose-dependent manner.

It is anticipated that in infected animals this reduction in virus production would give the immune system an advantage in combating infection and reducing clinical disease while allowing the establishment of long-term protective immune memory.

Example: MTT Toxicity Assay

All experiments shown were carried out in HEp2 cells. Cells were grown in 96 well plates overnight as previously described in 10% FCS medium to 95% confluence level. The medium was aspirated off and replaced with 200ul media with 2% FCS +/− compounds in DMSO carrier as indicated at an identical dilution series to that used in the plaque assays. 8 wells were used per compound/carrier alone dilution. An additional 2 rows of 8 cells were grown in medium alone for reference and subsequently 8 would be used as a cell death control as described below. Cells were incubated at 33° C. as indicated. If the incubation period exceeded 4 days the medium was replaced with the appropriate amount of fresh medium plus compound.

MTT assays were commenced 4 hours before the time period expired. Here 20 uL of MTT [(3-{4,5-dimethylthiazol-2-yl}-2,5-diphenyltetrazolium bromide)] solution (7.5 mg/ml in PBS) was added. One of the medium alone rows had 20 µL of SDS added (cell death control). The cells were placed back in the incubator at 33° C. After 4 hours, 100 µL of a stop solution (50% formamide, 20% w/v SDS) was added and pipetted to dissolve the substrate. Plates were then left overnight to allow the bubbles to disappear and the OD was recorded at 595 nm. Following subtraction of background solution colour (cell death control), the optical density was expressed as a percentage compared to the DMSO control on each appropriate plate.

Results

Figure 11:
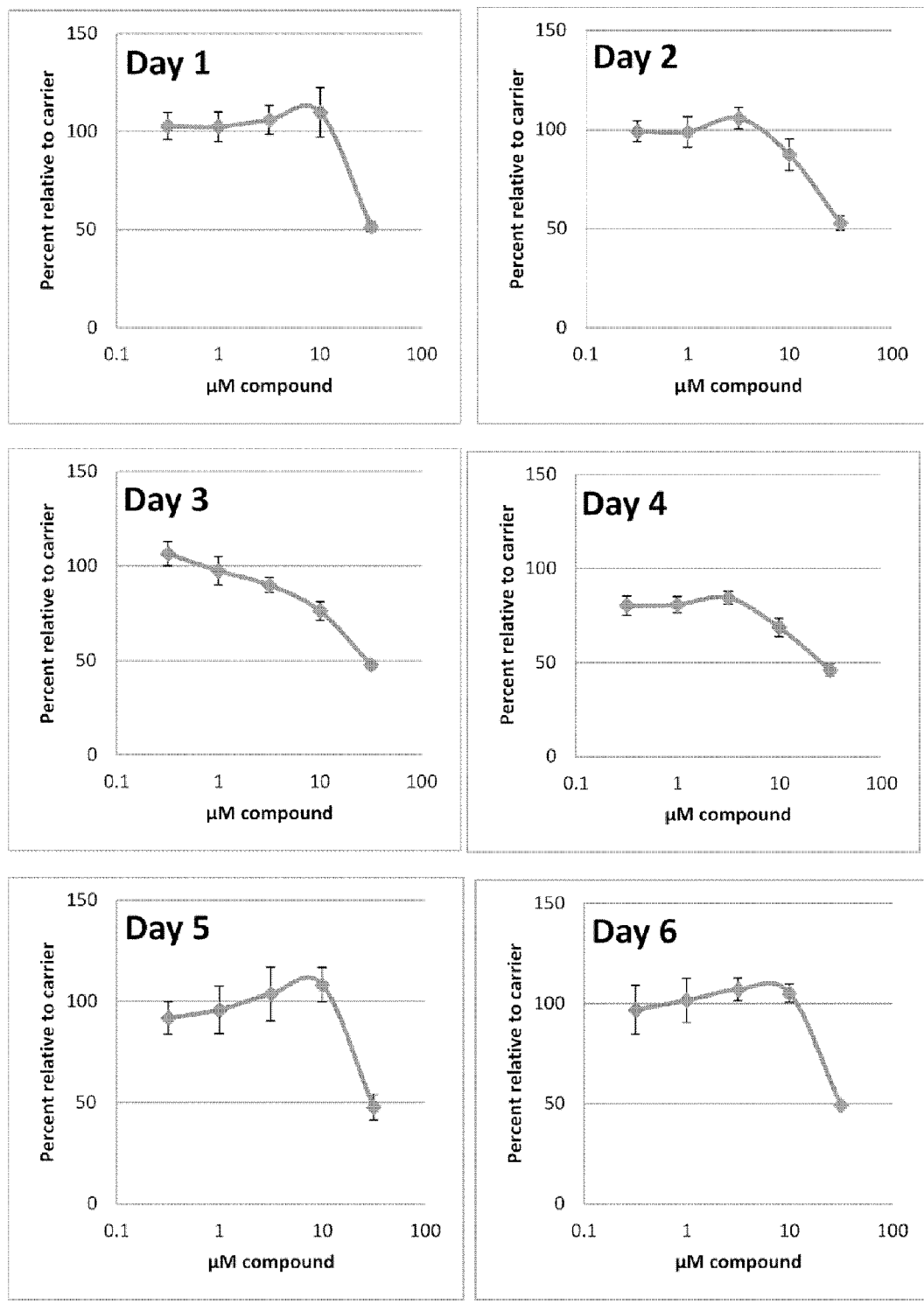
FIG. 11 shows results of an MTT assay for compound 1
Figure 12:
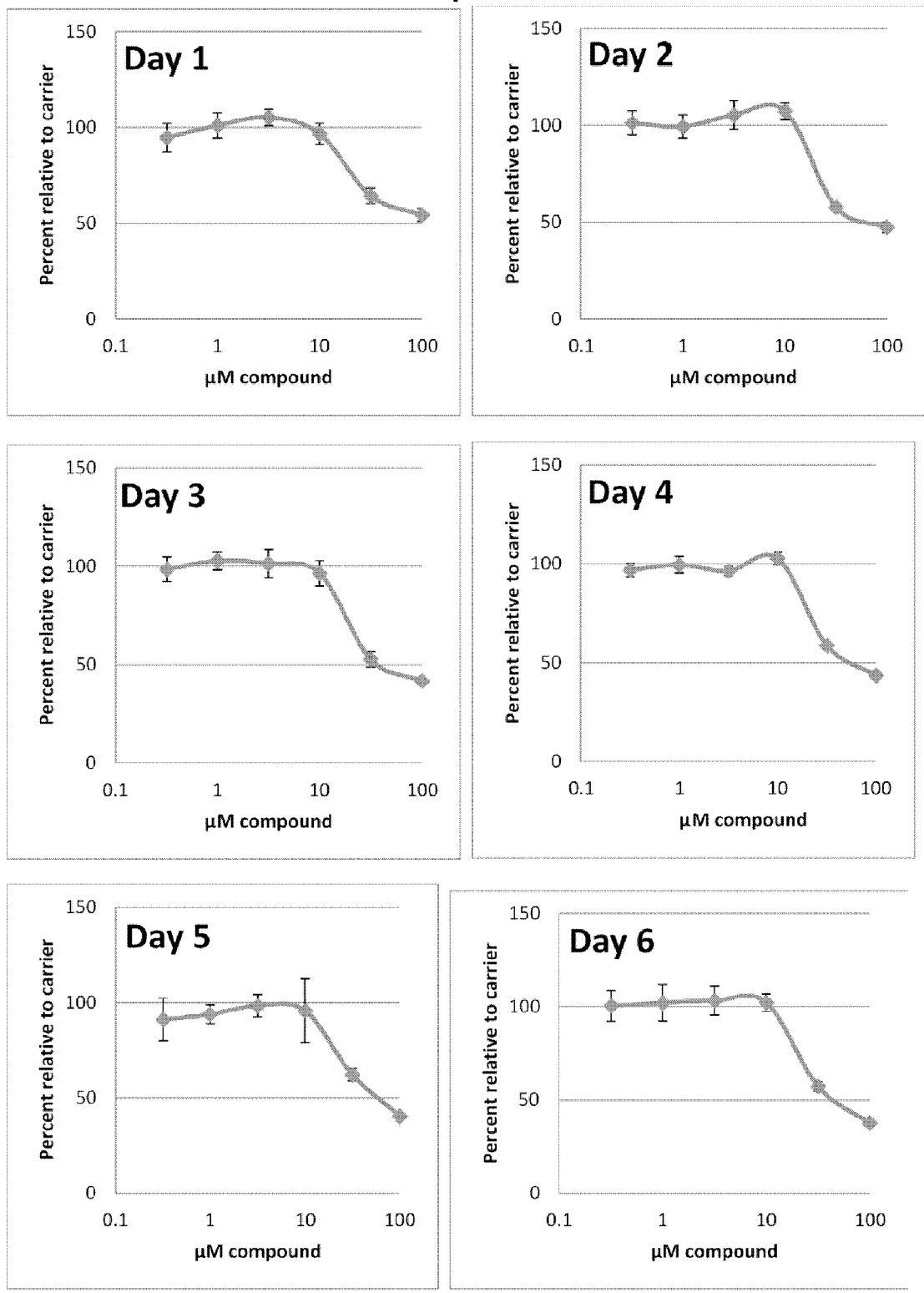
FIG. 12 shows results of an MTT assay for compound 4
Figure 13:
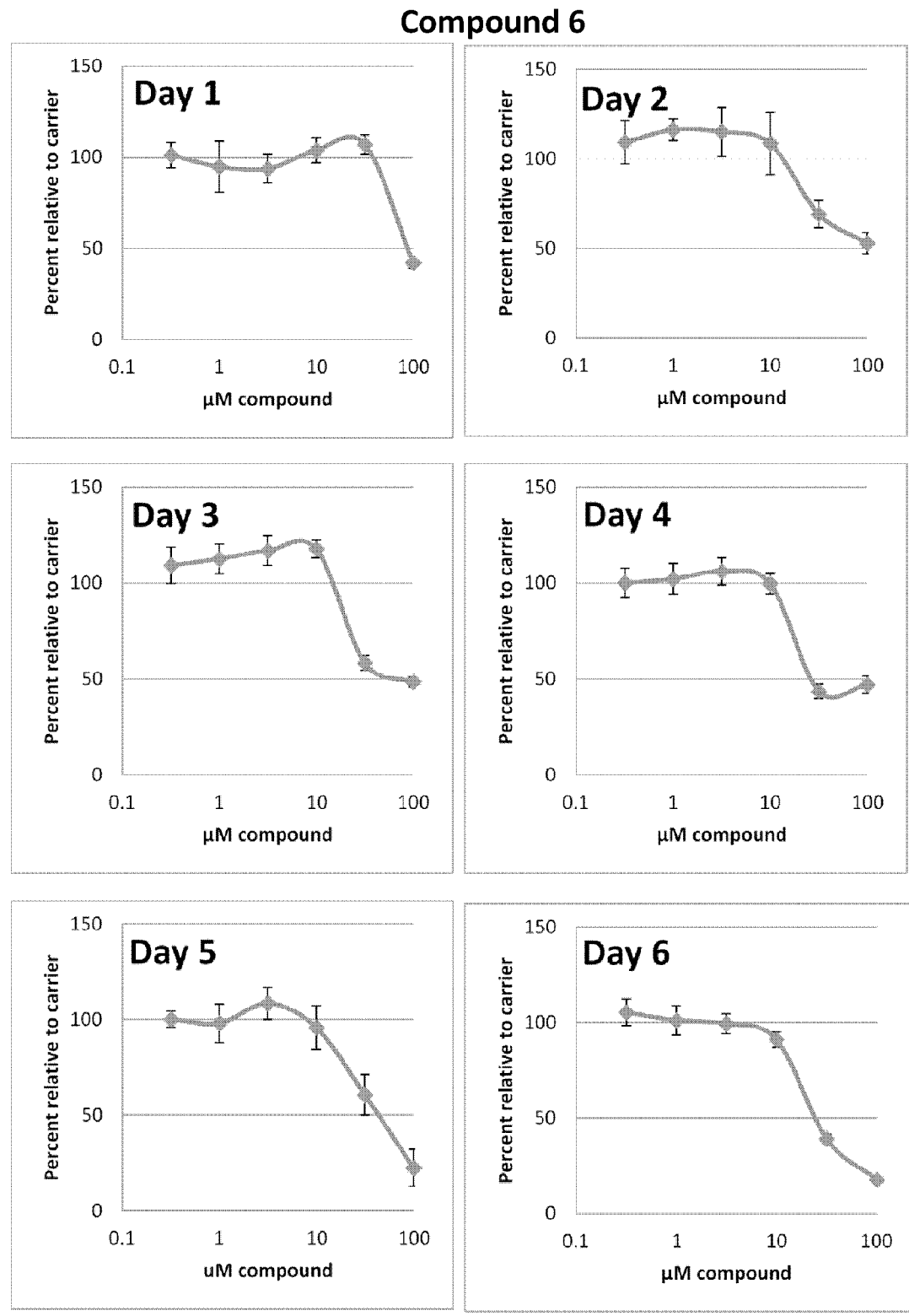
FIG. 13 shows results of an MTT assay for compound 6
Figure 14:
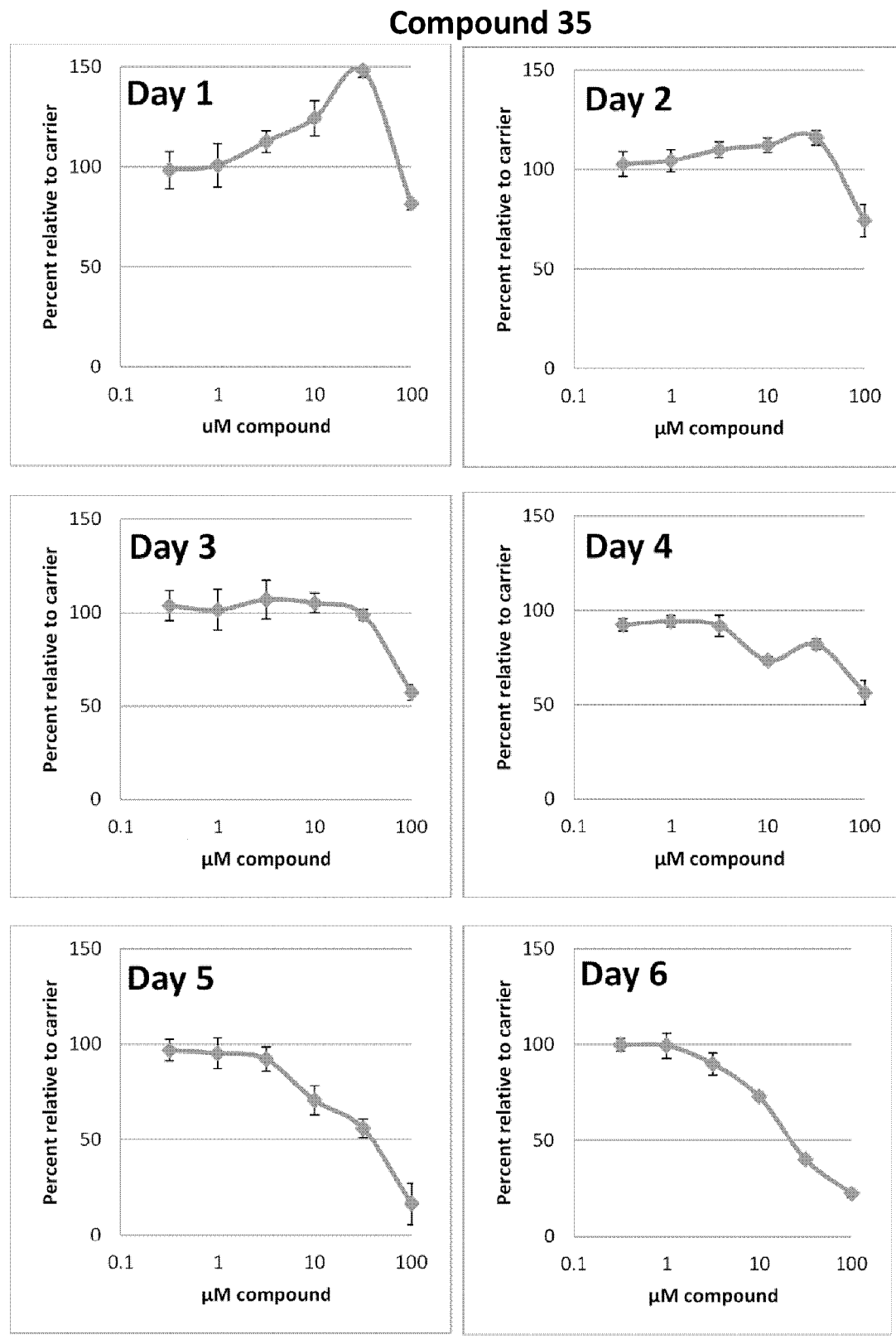
FIG. 14 shows results of an MTT assay for compound 35
Figure 15:
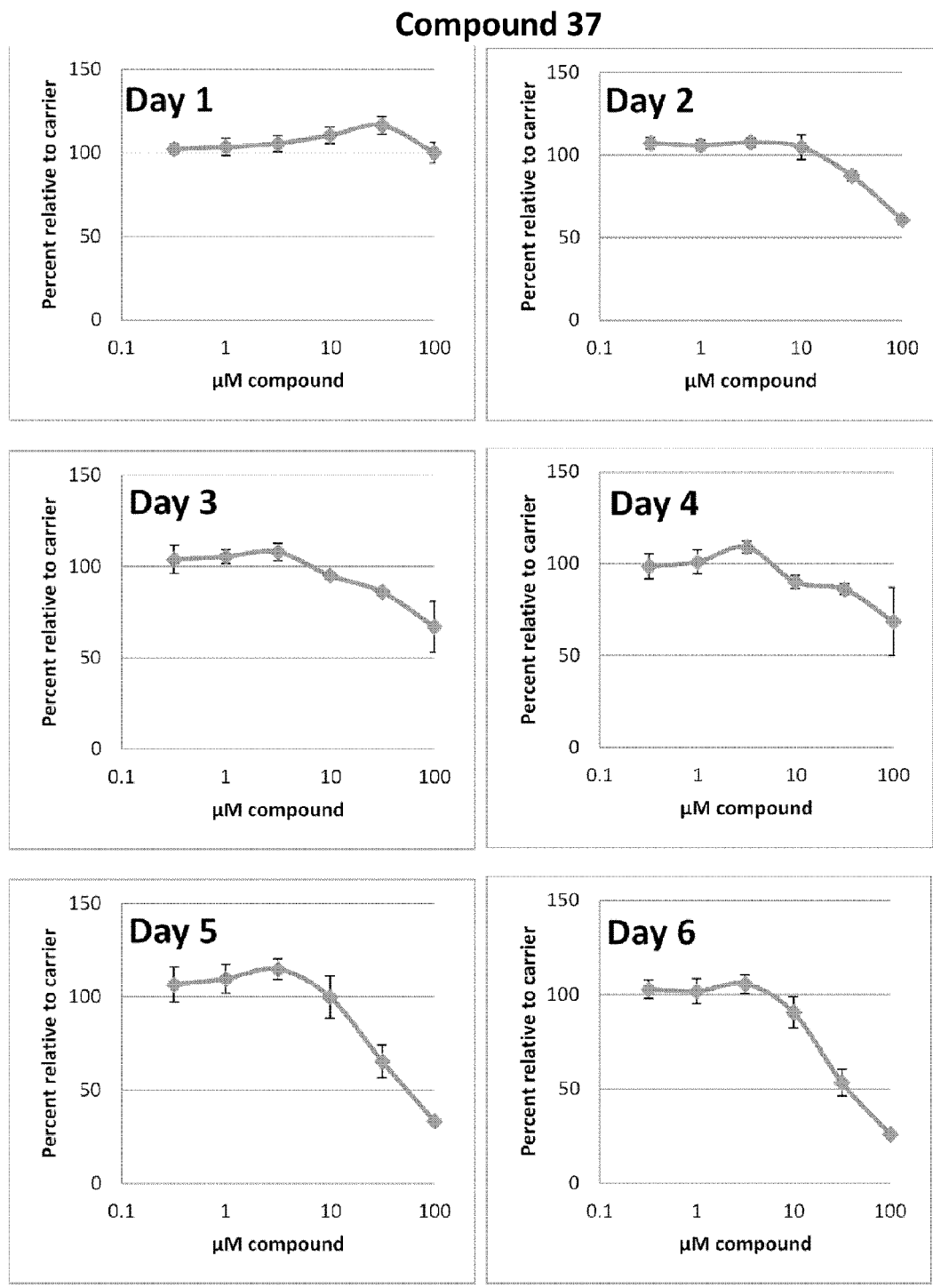
FIG. 15 shows results of an MTT assay for compound 37

Compounds 1, 4, 6, 35, and 37 were tested in an MTT assay which gives a measure of metabolic activity that can be inferred as an indication of cell viability. Solubility issues of compound 1 prevented the testing of the compound at 100 µM (FIGS. 11 to 15: FIG. 11—compound 1; FIG. 12—compound 4; FIG. 13—compound 6; FIG. 14—compound 35; FIG. 15—compound 37).

Compounds 4, 6 and 37 show inhibition of activity above 10 µM over the time course. Cell monolayers appeared intact and were not different from carrier controls as previously noted in the plaque assays. Compound 35 showed greater inhibition as previously observed with a reduction in viability above 3.2 µM after 4 days. Cell monolayers treated with 32 µM and above of compound 35 showed signs of death as the time course progressed. A rapid increase in cell growth on day 1 for compound 35 (FIG. 14) could indicate an adverse cellular response (such as apoptosis).

Compound 1 showed a similar level of inhibition to compounds 4, 6 and 37 with inhibition seen above 10 µM. However on days 3 and 4 compound 1 showed an increased sensitivity (FIG. 11). This disappeared after 5 days (following a media change at day 4). Based on the solubility issues the increased toxicity seen on days 3 and 4 could indicate slow solubilisation of the compound. When the media was refreshed with insoluble compound cells could recover.

The invention claimed is:

1. A method of treating pneumovirus infection in a subject, wherein the method comprises administration to the subject of an effective amount of a DDX3X inhibitor, wherein the DDX3X inhibitor is a compound of Formula (I):

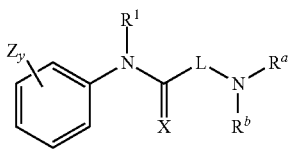

(I)

wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is independently O or S;
and wherein
i) L is a bond;
$R^1$ is H; and
either
a) $R^a$ is selected from H and substituted or unsubstituted $C_{1-3}$ alkyl, and
$R^b$ is selected from:
substituted or unsubstituted $C_{1-10}$ alkyl, substituted or unsubstituted $C_{4-8}$ cycloalkyl, and
phenyl or 6-membered heteroaryl, each of which may be optionally substituted with up to 2 substituents Z,
or
b) $R^a$ and $R^b$, together with the nitrogen atom to which they are attached, form a 5- or 6-membered substituted or unsubstituted heterocyclyl ring;
or
ii) L is selected from:

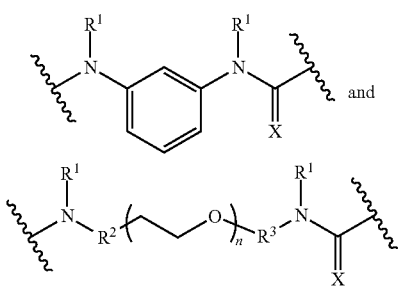

where n is 0, 1, 2, 3 or 4, and the wavy lines indicate the points of attachment to the rest of the molecule;
each $R^1$ is H;
each $R^2$ is a bond or is independently selected from substituted or unsubstituted $C_{1-3}$ alkyl;
each $R^3$ is selected from substituted or unsubstituted $C_{1-6}$ alkyl;
$R^a$ is selected from H and substituted or unsubstituted $C_{1-3}$ alkyl, and
$R^b$ is phenyl which may be optionally substituted with up to 2 substituents Z;
or a tautomer or a pharmaceutically acceptable salt thereof.

2. The method of claim 1, wherein the DDX3X inhibitor is a human DDX3X inhibitor, a bovine DDX3X inhibitor, an ovine DDX3X inhibitor, and/or a caprine DDX3X inhibitor.

3. The method of claim 1, wherein
y is 1;
each Z is independently selected from methyl, acetyl, methoxy, methylthio, methylsulfoxide, methylsulfonyl, bromo, nitro, cyano, chloro and substituted $C_1$alkyl;
each X is independently O or S;
and wherein
i) L is a bond;
$R^a$ is H; and
$R^b$ is selected from:
2-methylcyclohexyl, n-octanyl,
phenyl substituted with one substituent Z,
pyridinyl, and
pyrimidinyl;
or
ii) L is selected from:

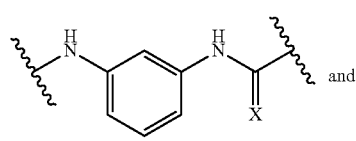

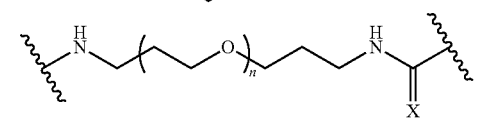

where n is 3, and the wavy lines indicate the points of attachment to the rest of the molecule;
$R^a$ is H; and
$R^b$ is phenyl substituted with one substituent Z.

4. The method of claim 1, wherein the DDX3X inhibitor is a compound of Formula (II):

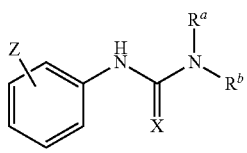

(II)

wherein either
a) $R^a$ is selected from H and substituted or unsubstituted $C_{1-3}$ alkyl, and
$R^b$ is selected from:
substituted or unsubstituted $C_{1-10}$ alkyl, substituted or unsubstituted $C_{4-8}$ cycloalkyl, and
phenyl or 6-membered heteroaryl, each of which may be optionally substituted with up to 2 substituents Z,
or
b) $R^a$ and $R^b$, together with the nitrogen atom to which they are attached, form a 5- or 6-membered substituted or unsubstituted heterocyclyl ring;
or a tautomer or a pharmaceutically acceptable salt thereof.

5. The method of claim 4, wherein $R^a$ is H, $R^b$ is selected from:
phenyl substituted with 1 substituent Z,
pyridinyl and
pyrimidinyl;
and at least one Z is a meta or para substituent selected from methoxy, methylthio, cyano, nitro, bromo, chloro and $CF_3$.

6. The method of claim 1 wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is O;
and wherein
L is a bond;
$R^1$ is H; and
either
a) $R^a$ is selected from H and substituted or unsubstituted $C_{1-3}$ alkyl, and
$R^b$ is selected from:
substituted or unsubstituted $C_{1-10}$ alkyl, substituted or unsubstituted $C_{4-8}$ cycloalkyl, and
phenyl or 6-membered heteroaryl, each of which may be optionally substituted with up to 2 substituents Z,
or
b) $R^a$ and $R^b$, together with the nitrogen atom to which they are attached, form a 5- or 6-membered substituted or unsubstituted heterocyclyl ring;
or a tautomer or a pharmaceutically acceptable salt thereof.

7. The method of claim 1 wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is O;
and wherein
L is a bond;
$R^1$ is H; and
either
a) $R^a$ is selected from H and substituted or unsubstituted $C_{1-3}$ alkyl, and
$R^b$ is selected from:
phenyl or 6-membered heteroaryl, each of which may be optionally substituted with up to 2 substituents Z,
or
b) $R^a$ and $R^b$, together with the nitrogen atom to which they are attached, form a 5- or 6-membered substituted or unsubstituted heterocyclyl ring;
or a tautomer or a pharmaceutically acceptable salt thereof.

8. The method of claim 1 wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is O;
and wherein
L is a bond;
$R^1$ is H;
$R^a$ is selected from H and substituted or unsubstituted $C_{1-3}$ alkyl, and
$R^b$ is selected from:
phenyl or 6-membered heteroaryl, each of which may be optionally substituted with up to 2 substituents Z;
or a tautomer or a pharmaceutically acceptable salt thereof.

9. The method of claim 1 wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is O;
and wherein
L is a bond;
$R^1$ is H;
$R^a$ is selected from H and substituted or unsubstituted $C_{1-3}$ alkyl, and
$R^b$ is phenyl which may be optionally substituted with up to 2 substituents Z;
or a tautomer or a pharmaceutically acceptable salt thereof.

10. The method of claim 1 wherein
y is 1 or 2;
each Z is independently selected from substituted or unsubstituted $C_{1-3}$ alkoxy, substituted or unsubstituted $C_{1-3}$ alkylthio, and cyano;
each X is O;
and wherein
L is a bond;
$R^1$ is H;
$R^a$ is selected from H and substituted or unsubstituted $C_{1-3}$ alkyl, and
$R^b$ is phenyl which may be optionally substituted with up to 2 substituents Z;
or a tautomer or a pharmaceutically acceptable salt thereof.

11. The method of claim 1 wherein
y is 1;
each Z is independently selected from substituted or unsubstituted $C_{1-3}$ alkoxy, substituted or unsubstituted $C_{1-3}$ alkylthio, and cyano;

each X is O;
and wherein
L is a bond;
R¹ is H;
Rᵃ is H, and
Rᵇ is phenyl substituted with 1 substituent Z;
or a tautomer or a pharmaceutically acceptable salt thereof.
12. The method of claim 1, wherein the compound is selected from the group consisting of:
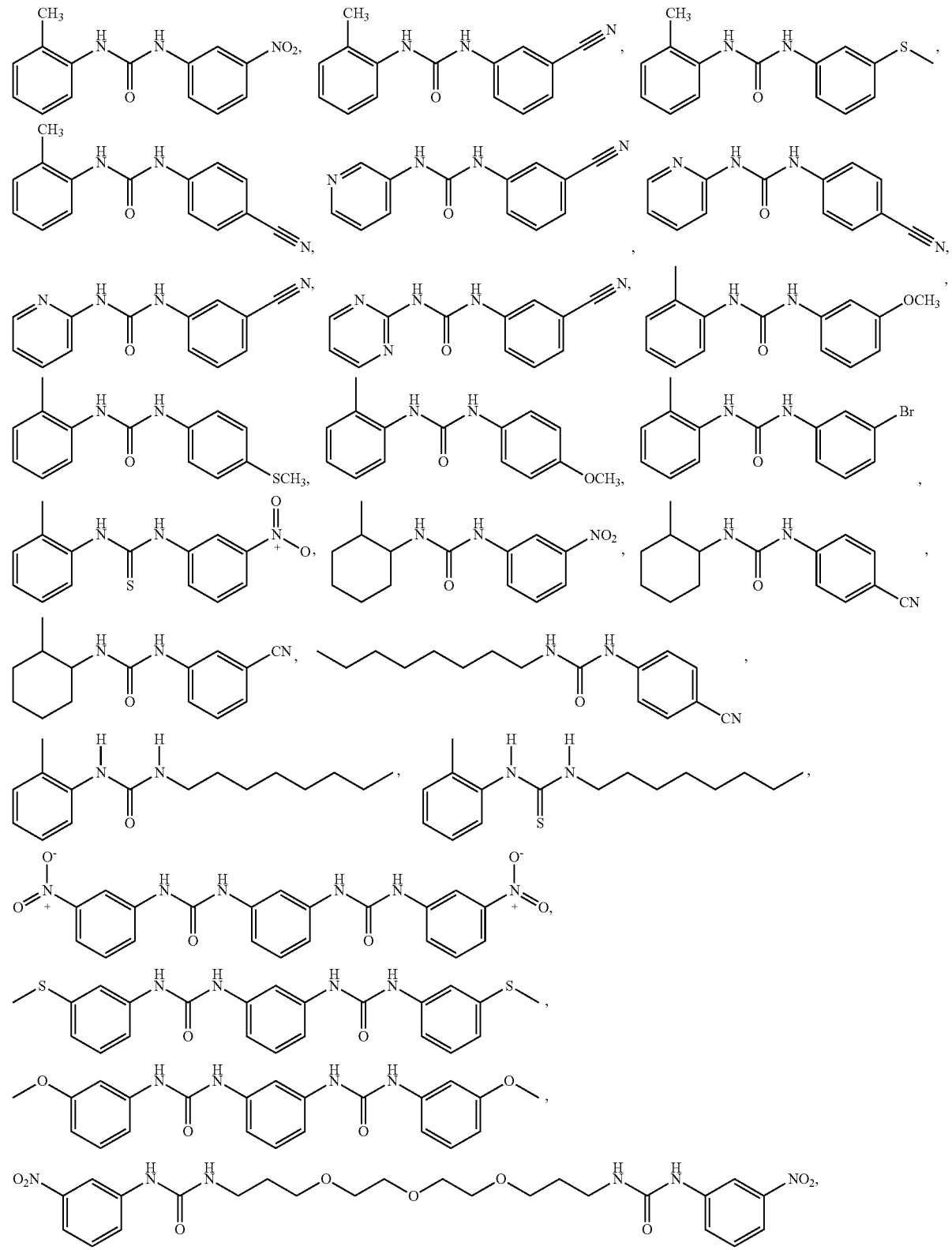

-continued
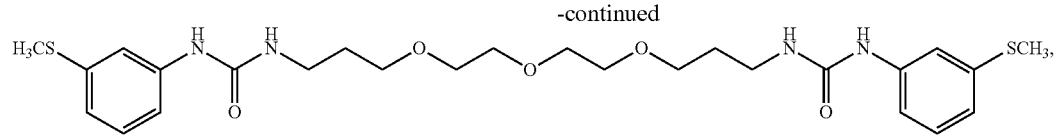
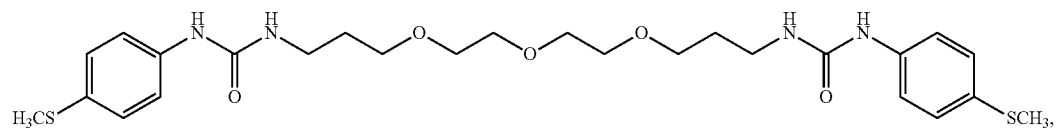
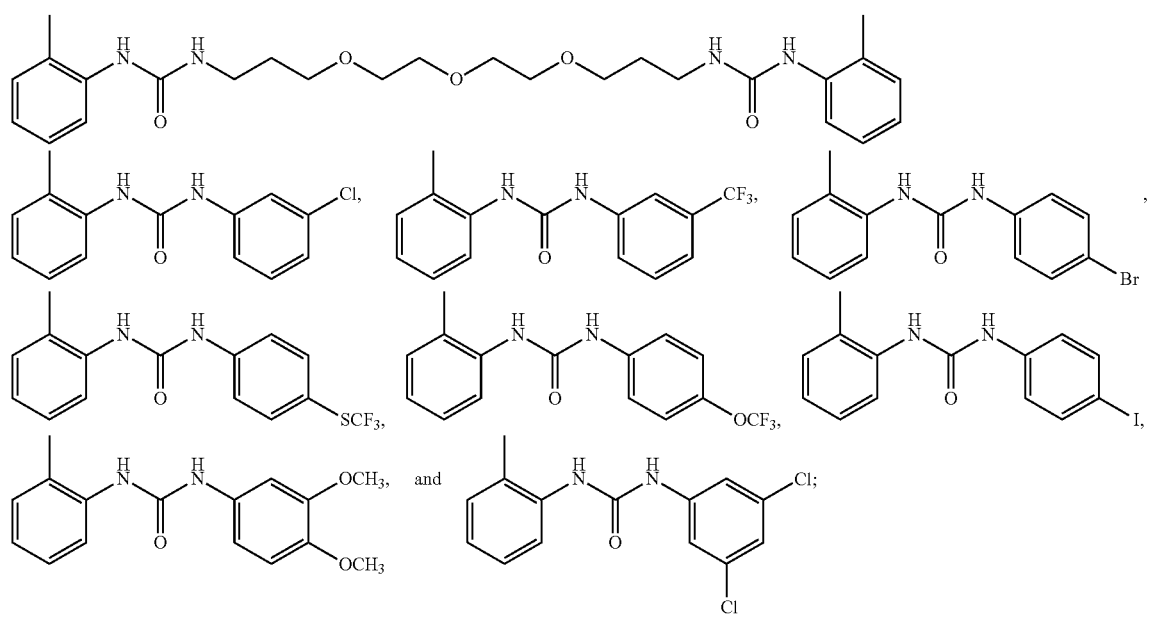
tautomers and pharmaceutically acceptable salts thereof.
13. The method of claim 1, wherein the compound is selected from the group consisting of:
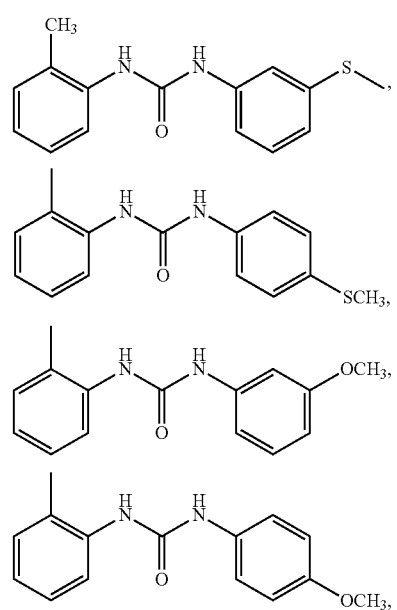
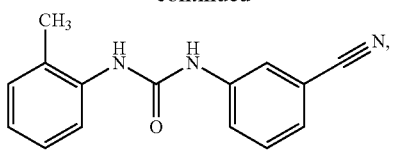
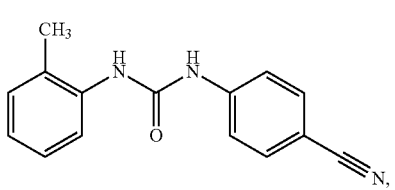
tautomers and pharmaceutically acceptable salts thereof.
14. The method of claim 1, wherein the compound is selected from the group consisting of:
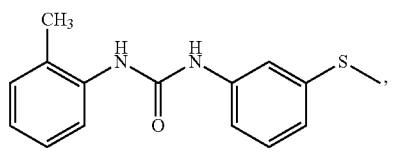

-continued

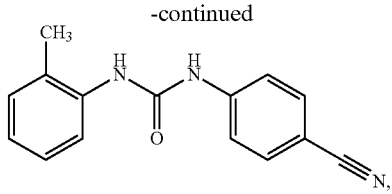

tautomers and pharmaceutically acceptable salts thereof.

15. The method of claim 1, wherein the subject is a mammal selected from humans, cattle, sheep and goats.

16. A compound of Formula (I):

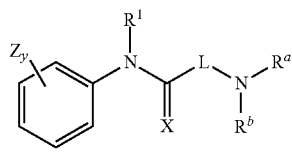

wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is independently O or S;
and wherein
i) L is a bond;
each $R^1$ is H; and
either
a) $R^a$ is selected from H and substituted or unsubstituted $C_{1-3}$ alkyl, and
$R^b$ is selected from:
substituted or unsubstituted $C_{1-10}$ alkyl, substituted or unsubstituted $C_{4-8}$ cycloalkyl, and
phenyl or 6-membered heteroaryl, each of which may be optionally substituted with up to 2 substituents Z,
or
b) $R^a$ and $R^b$, together with the nitrogen atom to which they are attached, form a 5- or 6-membered substituted or unsubstituted heterocyclyl ring;
or
ii) L is selected from:

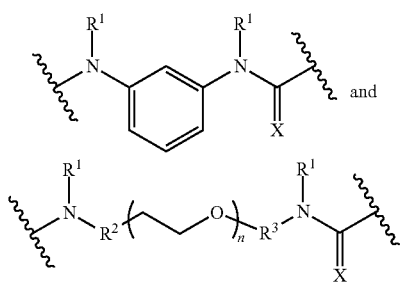

where n is 0, 1, 2, 3 or 4, and the wavy lines indicate the points of attachment to the rest of the molecule;
each $R^1$ is H;

each $R^2$ is a bond or is independently selected from substituted or unsubstituted $C_{1-3}$ alkyl;
each $R^3$ is selected from substituted or unsubstituted $C_{1-6}$ alkyl;
$R^a$ is selected from H and substituted or unsubstituted $C_{1-3}$ alkyl, and
$R^b$ is phenyl which may be optionally substituted with up to 2 substituents Z;
or a tautomer or a pharmaceutically acceptable salt thereof, provided that the compound is other than:

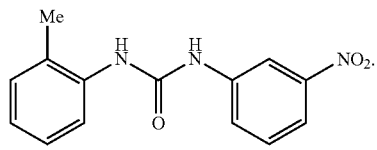

17. The compound according to claim 16, wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is O;
and wherein
L is a bond;
each $R^1$ is H; and
either
a) $R^a$ is selected from H and substituted or unsubstituted $C_{1-3}$ alkyl, and
$R^b$ is selected from:
substituted or unsubstituted $C_{1-10}$ alkyl, substituted or unsubstituted $C_{4-8}$ cycloalkyl, and
phenyl or 6-membered heteroaryl, each of which may be optionally substituted with up to 2 substituents Z,
or
b) $R^a$ and $R^b$, together with the nitrogen atom to which they are attached, form a 5- or 6-membered substituted or unsubstituted heterocyclyl ring;
or a tautomer or a pharmaceutically acceptable salt thereof, provided that the compound is other than:

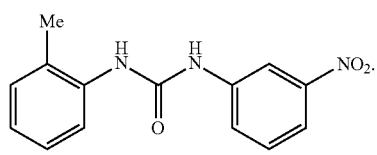 [SMILES: Cc1ccccc1NC(=O)Nc1cccc([N+](=O)[O-])c1]

18. The compound according to claim 16, wherein
y is 0, 1, or 2;
each Z is independently selected from substituted or unsubstituted $C_{1-3}$ alkyl, substituted or unsubstituted $C_{1-3}$ acyl, substituted or unsubstituted $C_{1-3}$ alkoxy, substituted or unsubstituted $C_{1-3}$ alkylthio, substituted or unsubstituted $C_{1-3}$ alkylsulfoxide, substituted or unsubstituted $C_{1-3}$ alkylsulfonyl, halo, nitro, and cyano;
each X is O;

and wherein

L is a bond;

each $R^1$ is H;

$R^a$ is selected from H and substituted or unsubstituted $C_{1-3}$ alkyl; and $R^b$ is phenyl which may be optionally substituted with up to 2 substituents Z;

or a tautomer or a pharmaceutically acceptable salt thereof, provided that the compound is other than:

19. The compound of claim 16, wherein the compound is selected from the group consisting of:

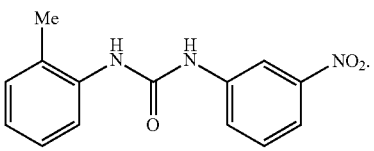 [SMILES: Cc1ccccc1NC(=O)Nc1cccc([N+](=O)[O-])c1]
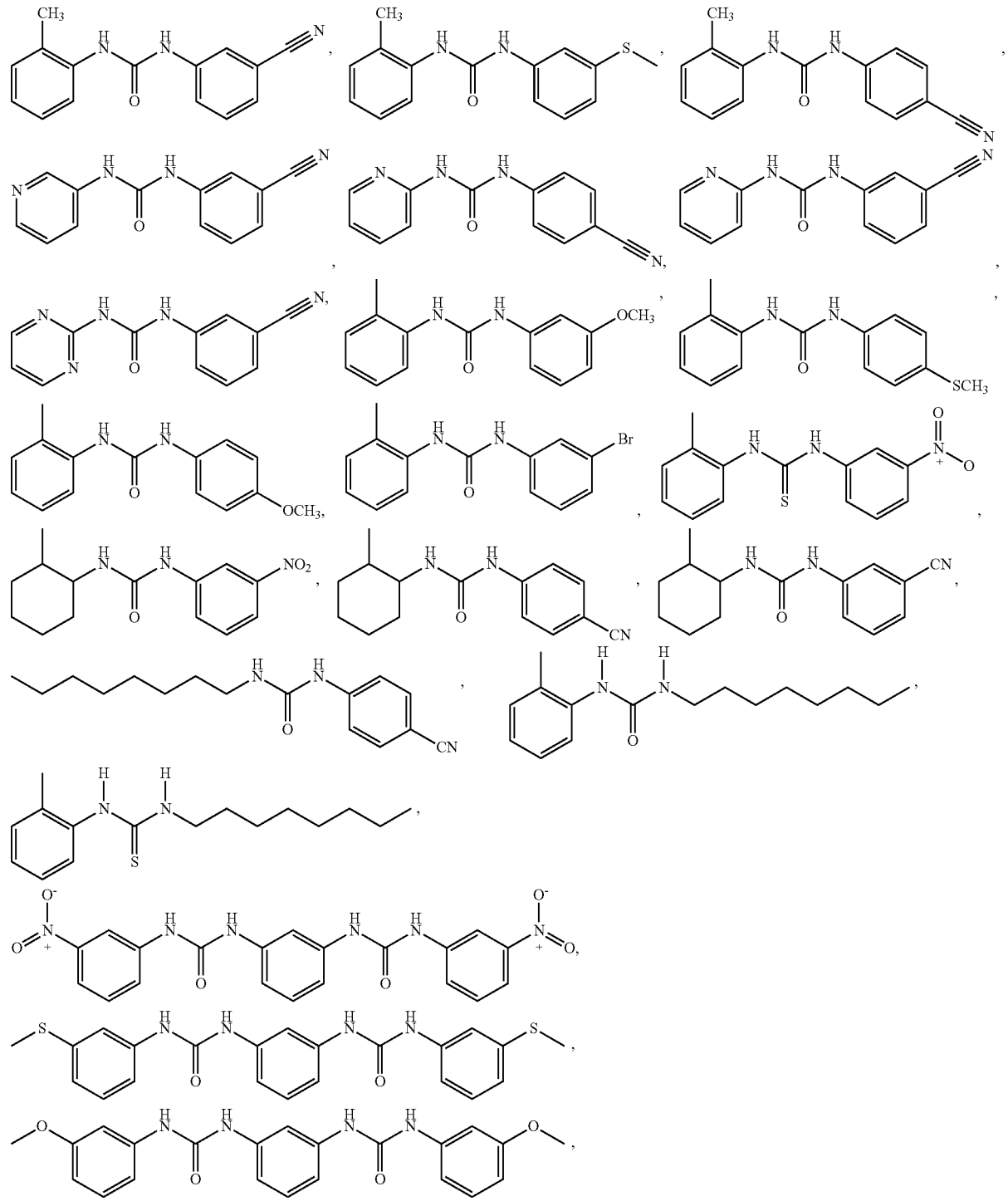

-continued
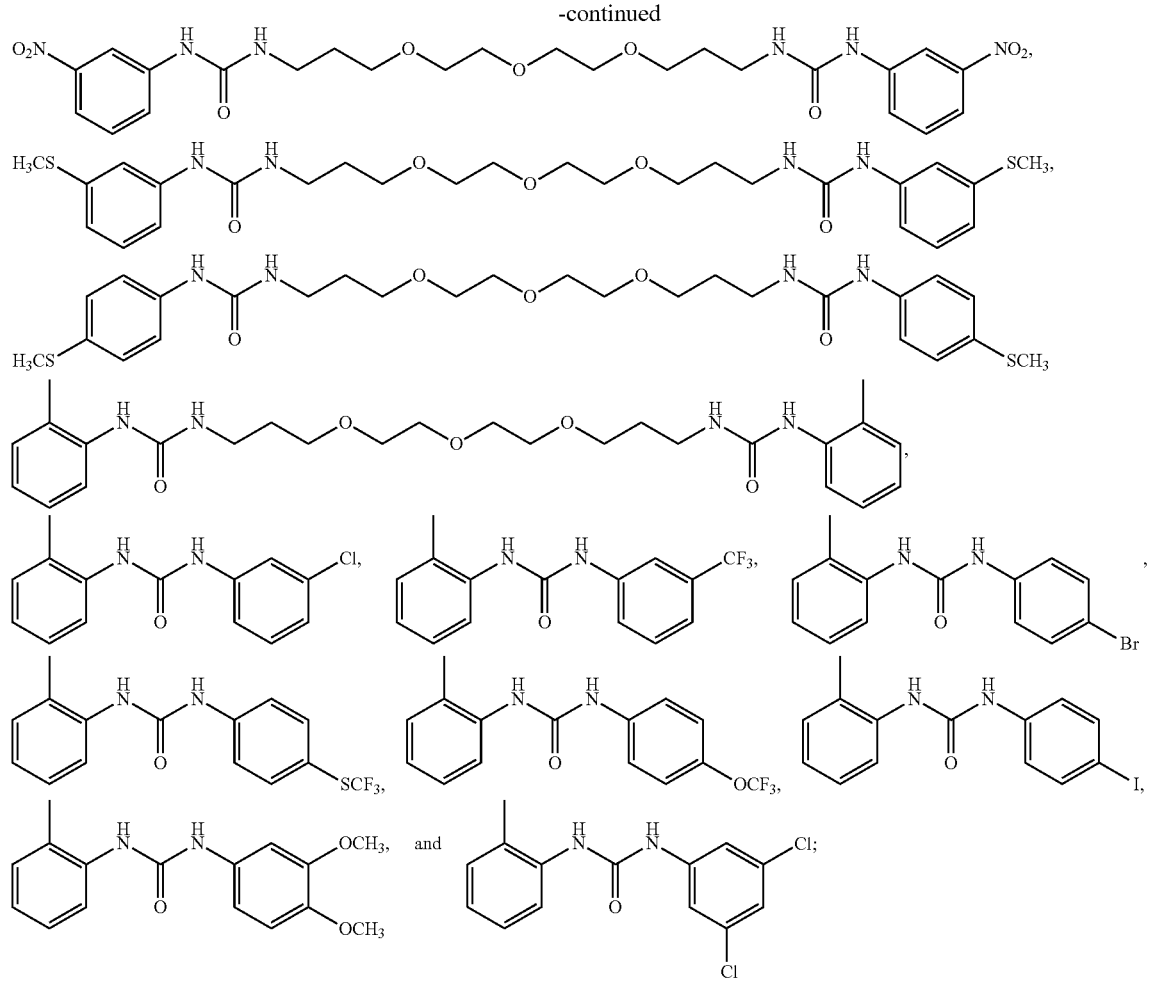
tautomers and pharmaceutically acceptable salts thereof.
20. The compound of claim 16, wherein the compound is selected from the group consisting of:
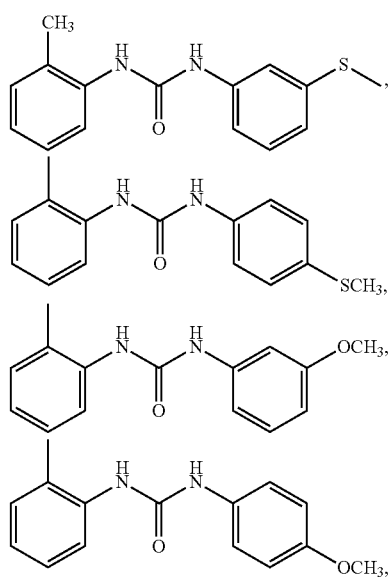
-continued
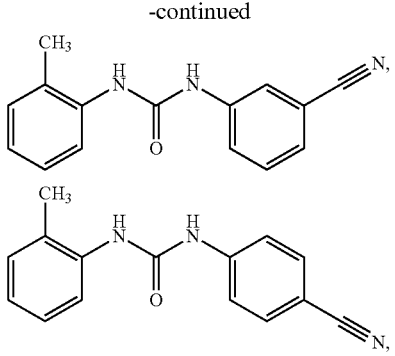
tautomers and pharmaceutically acceptable salts thereof.
21. The compound of claim 16, wherein the compound is selected from the group consisting of:
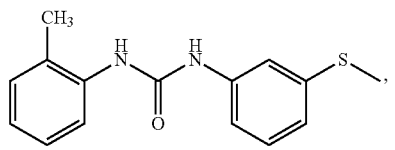

-continued

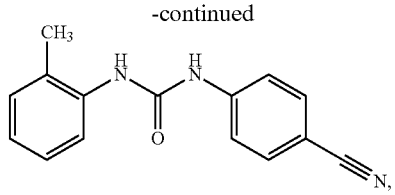
tautomers and pharmaceutically acceptable salts thereof.
22. A pharmaceutical composition comprising the compound of claim 16 and a pharmaceutically-acceptable excipient.

23. A method of identifying an agent which modulates pneumovirus replication comprising contacting an agent with (a) an RNA construct comprising the sequence of nucleotides 392-511 of the pneumovirus M2 transcript and (b) a protein comprising DDX3X, and determining whether the agent modulates the interaction between the construct and DDX3X.

24. The method of claim 23, wherein the pneumovirus is a human RSV (hRSV).

25. The method of claim 23, wherein the pneumovirus is a bovine RSV (bRSV).

* * * * *

SEQUENCE LISTING

```
<160> NUMBER OF SEQ ID NOS: 13

<210> SEQ ID NO 1
<211> LENGTH: 961
<212> TYPE: RNA
<213> ORGANISM: Human respiratory syncytial virus

<400> SEQUENCE: 1
ggggcaaaua ugucacgaag gaauccuugc aaauuugaaa uucgagguca uugcuuaaau       60
gguaagaggu gucauuuuag ucauaauuau uuugaauggc caccccaugc acugcuugua      120
agacaaaacu uuauguuaaa cagaauacuu aagucuaugg auaaaaguau agauaccuua      180
ucagaaauaa guggagcugc agaguuggac agaacagaag aguaugcucu ugguguaguu      240
ggagugcuag agaguuauau aggaucaaua aacaauauaa cuaaacaauc agcaugeguu      300 gccaugagca aacuccucac ugaacucaau agugaugaua ucaaaaagcu gagggacaau      360
gaagagcuaa auucacccaa gauaagagug uacaauacug ucauaucaua uauugaaagc      420
aacaggaaaa acaauaaaca aacuauccau cuguuaaaaa gauugccagc agacguauug      480
aagaaaacca ucaaaaacac auuggauauc cauaagagca uaaccaucaa caacccaaaa      540
gaaucaacug uuagugauac aaaugaccau gccaaaaaua augauacuac cugacaaaua      600
uccuuguagu auaacuucca uacuaauaac aaguagaugu agaguuacua uguauaauca      660
aaagaacaca cuauauuuca aucaaaacaa cccaaauaac cauauguacu caccgaauca      720
aacauucaau gaauccauu ggaccucuca agaauugauu gacacaauuc aaaauuuucu      780
acaacaucua gguauuauug aggauauaua uacaauauau auauuagugu cauaacacuc      840
aauucuaaca cucaccacau cguuacauua uuaauucaaa caauucaagu uguggggacaa      900 aauggauccc auuauuaaug gaaauucugc uaauguuuau cuaaccgaua guuauuuaaa      960
a                                                                    961

<210> SEQ ID NO 2
<211> LENGTH: 194
```

<212> TYPE: PRT
<213> ORGANISM: Human respiratory syncytial virus

<400> SEQUENCE: 2

```
Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Ser Thr Val Ser Asp Thr Asn Asp His Ala Lys Asn Asn Asp
            180                 185                 190

Thr Thr
```

<210> SEQ ID NO 3
<211> LENGTH: 90
<212> TYPE: PRT
<213> ORGANISM: Human respiratory syncytial virus

<400> SEQUENCE: 3

```
Met Thr Met Pro Lys Ile Met Ile Leu Pro Asp Lys Tyr Pro Cys Ser
1               5                   10                  15

Ile Thr Ser Ile Leu Ile Thr Ser Arg Cys Arg Val Thr Met Tyr Asn
            20                  25                  30

Gln Lys Asn Thr Leu Tyr Phe Asn Gln Asn Pro Asn Asn His Met
        35                  40                  45                  Met

Tyr Ser Pro Asn Gln Thr Phe Asn Glu Ile His Trp Thr Ser Gln Glu
    50                  55                  60

Leu Ile Asp Thr Ile Gln Asn Phe Leu Gln His Leu Gly Ile Ile Glu
65                  70                  75                  80

Asp Ile Tyr Thr Ile Tyr Ile Leu Val Ser
                85                  90
```

<210> SEQ ID NO 4
<211> LENGTH: 961
<212> TYPE: RNA
<213> ORGANISM: Human respiratory syncytial virus

<400> SEQUENCE: 4
ggggcaaaua ugucacgaag gaauccuugc aaauuugaaa uucgagguca uugcuuaaau    60

| | | | | |
|---|---|---|---|---|
| gguaagaggu | gucauuuuag | ucauaauuau | uuugaauggc | caccccaugc acugcuugua | 120 |
| agacaaaacu | uuauguuaaa | cagaauacuu | aagucuaugg | auaaaaguau agauaccuua | 180 |
| ucagaaauaa | guggagcugc | agaguuggac | agaacagaag | aguaugcucu gguguaguu | 240 |
| ggagugcuag | agaguuauau | aggaucaaua | acaauauaa | cuaacaauc agcaugucu | 300 |
| gccaugagca | aacuccucac | ugaacucaau | agugaugaua | ucaaaaagcu gagggacaau | 360 |
| gaagagcuaa | auucacccaa | gauaagagug | uacaauacug | ucauaucaua auugaaagc | 420 |
| aacaggaaaa | acaauaaaca | aacuauccau | cuguuaaaaa | gauugccagc agacguauug | 480 |
| aagaaaacca | ucaaaaacac | auuggauauc | cauaagagca | uaaccaucaa caacccaaaa | 540 |
| gaaucaacug | uuagugauac | aaaugaccau | gccaaaaaua | augauacuac cugacaaaua | 600 |
| uccuuguagu | auaacuucca | uacuaauaac | aaguagaugu | agaguuacua uguauaauca | 660 |
| aaagaacaca | cuauauuuca | aucaaaacaa | cccaaauaac | cauaugacu caccgaauca | 720 |
| aacauucaau | gaaauccauu | ggaccucuca | agaauugauu | gacacaauuc aaaauuuucu | 780 |
| acaacaucua | gguauuauug | aggauauaua | ucaauauau | auauuagugu cauaacacuc | 840 |
| aauucuaaca | cucaccacau | cguuacauua | uaauucaaa | caauucaagu gugggacaa | 900 |
| aauggauccc | auuauuaaug | gaaauucgc | uaauguuau | cuaaccgaua guuauuaaa | 960 |
| a | | | | | 961 |

<210> SEQ ID NO 5
<211> LENGTH: 874
<212> TYPE: RNA
<213> ORGANISM: Human respiratory syncytial virus

<400> SEQUENCE: 5

| | | | | |
|---|---|---|---|---|
| ggggcaaaua | ugucgcgaag | aaauccuugu | aaauuugaga | uuagagguca uugcuugaau | 60 |
| gguagaagau | gucacuacag | ucauaauuac | uuugaauggc | cuccucaugc cuuacuagug | 120 |
| aggcaaaacu | ucauguuaaa | caagauacuc | aagucaaugg | acaaaagcau agacacuuug | 180 |
| ucugaaauaa | guggagcugc | ugaacuggac | agaacagaag | aauaugcucu gguauaguu | 240 |
| ggagugcuag | agaguuacau | aggaucauua | acaacauaa | caaacaauc agcaugucu | 300 |
| gcuaugagua | acuucuuau | ugagaucaau | agugaugaca | uuaaaaagcu gagagauaau | 360 |
| gaagaaccca | auucaccuaa | gauaagagug | uacaauacug | uuauaucaua cauugagagc | 420 |
| aauagaaaaa | acaacaagca | acaauccau | cugcucaaaa | gacuaccagc agacgugcug | 480 |
| aagaagacaa | uaaaaacac | auuagauauc | cacaaaagca | uaaucauaag caacccaaaa | 540 |
| gagucaaccg | ugaaugauca | aaaugaccaa | accaaaaaua | augauauuac cggauaaaua | 600 |
| uccuuguagu | auaucaucca | uauugauuuc | aagugaaagc | augauugcua cauucaauca | 660 |
| uaaaaacaua | uuacaauuua | accauaacca | uuuggauaac | caccagcguu auuaaauaa | 720 |
| uauauuugau | gaaauucauu | ggacaccuaa | aacuuauua | gaugccacuc aacaauuucu | 780 |
| ccaacaucuu | aacaucccug | aagauauaua | uacaauauau | auauuagugu cauaaugcuu | 840 |
| ggccauaacg | auucuauauc | auccaaccau | aaaa | | 874 |

<210> SEQ ID NO 6
<211> LENGTH: 960
<212> TYPE: RNA
<213> ORGANISM: Bovine respiratory syncytial virus

<400> SEQUENCE: 6

| | | | | |
|---|---|---|---|---|
| ggggcaaaua | ugucacgaag | aaauccuugc | aaauaugaga | uuaggggaca uugcuuaaau | 60 |

```
gguaaaaaau gucauuuuag ucauaauuac uuugaauggc cuccacaugc uuuauuagug     120
aggcaaaaau uuaugcuaaa uaagauauua aaaucuaugg acaggaacaa cgauacccug     180
ucagaaauaa guggugcagc agaguuggau agaacagaag aauaugcauu ggguguaaua     240
ggaguuuugg aaaguuaccu aggcucuauc aauaauauaa caaaacaauc agccugeguu    300 gcuaugagua aacuauuagc cgagauuaac aaugaugaca uaagagauu gaggaacaag      360 gaagugccaa caucaccuaa gauaagaaua uauaacacag uuauaucaua uauugauagc    420
aacaagagaa acacaaaaca aacuauacau uugcuuaaga gauugccugc agacguacuu     480
aaaaagacaa ucaagaacac uauagauauu cacaacgaaa uaaaugguaa uaaccaaggu    540
gacauaauug uuaaugaaca aaaugaauaa cuccaacauu auuauuuccc cagaaaaaua    600
cccuuguagc auauccucuu ugcuaauuaa gaaugaaaau gauguuauug uacuaaguca    660
ucaaaauguu cuugacuacu uacaguuuca auaccaugu aauauguauu cucaaaauca     720
uaugcuugau gauaucuauu ggacaucaca ggagcuaauu gaggauguac uuaagauucu    780
ucaucuuucu ggcauaucca uaaguaagua ugugauauau guuuuagugc uauaguauau    840
aagucacuca acuauuaauc aacagccacu ucuucauagc uagcaauaua uaaggacaaa    900
auggauacac ucauucauga gaacucaacu aauguuuacu uaacagauag uuauuuaaaa    960
```

<210> SEQ ID NO 7
<211> LENGTH: 964
<212> TYPE: RNA
<213> ORGANISM: Ovine respiratory syncytial virus

<400> SEQUENCE: 7

```
ggggcaaaua ugucacgaag aaaucccugc aaauaugaga ucaggggaca uugcuuaaau     60
ggcaaaaaau gccauuucag ccauaauuac uuugaauggc cuccacaugc uuuauuagug    120
aggcaaaauu uuauguuaaa caagauauua aagucuaugg auaggagcaa ugauacucug    180
ucagagauaa guggagcugc agaauuagau agaacagagg aauaugcauu aggugugaua    240
ggaguuuuag aaaguuacuu gggcucuguu aauaacauaa caaaacaauc agccugeguu    300 gcuaugagua aauuauuagg ugagauuaau agugaugaca ucaaaggauu aagaaacaaa    360
gaauugccaa cuucaccuaa gauaagaaua uauaacacag uuauaucaua uauugauagc    420
aacaagagaa acccaaaaca aacuauacau uuacuuaaaa gauugccugc agaugugcuu    480
aagaagacca ucaagaauac aauagauauu cacaaugaaa uaaauguuaa uaaccaagu     540 gacauaggug uuaaugaaca aaaugaauaa uccaauauc auuauuuccc cagagaaaua    600
uccuuguagu auacuucuu uguuaaucag agaugagaau aauguuauug uauuaaauca     660
ucagaauauu uuugacugcu cacagucuca acaccaugu gauauguauc cucaaaauca     720
uauacuugac uauaccauu ggacaucaca ggaauugauu gacgauguac uaaagauucu    780
ucaccuuucu agcauccca uaaauaggua uggcucuau gucuuagugc uguaguaugu    840
aaaucauuua acuuucaauc auuaucuaua uauuucuccu uguagccgga aauacaccag    900
aggacaaaau ggacucacuc auucaugaaa acucaaccaa uguauacuua acagauaguu    960
auuu                                                                  964
```

<210> SEQ ID NO 8
<211> LENGTH: 662
<212> TYPE: PRT
<213> ORGANISM: Homo sapiens

<400> SEQUENCE: 8

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
        275                 280                 285

Phe Ser Tyr Arg Ser Arg Val Arg Pro Cys Val Val Tyr Gly Gly Ala
    290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Phe Ser Ala Thr
    370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

```
Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
            435                 440                 445

Glu Thr Lys Lys Gly Ala Asp Ser Leu Glu Asp Phe Leu Tyr His Glu
450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
            515                 520                 525

Ile Gly Arg Thr Gly Arg Val Gly Asn Leu Gly Leu Ala Thr Ser Phe
530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
                565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
            595                 600                 605

Ser Ser Ser Ser Phe Ser Ser Ser Arg Ala Ser Ser Ser Arg Ser Gly
            610                 615                 620

Gly Gly Gly His Gly Ser Ser Arg Gly Phe Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
            660

<210> SEQ ID NO 9
<211> LENGTH: 662
<212> TYPE: PRT
<213> ORGANISM: Homo sapiens

<400> SEQUENCE: 9

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
```

-continued

```
            115                 120                 125
Asp Lys Ser Asp Glu Asp Trp Ser Lys Pro Leu Pro Ser Glu
            130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
            195                 200                 205

His Ala Ile Pro Ile Ile Lys Glu Lys Arg Asp Leu Met Ala Cys Ala
            210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
                260                 265                 270

Ala Pro Thr Arg Glu Leu Ala Val Gln Ile Tyr Glu Glu Ala Arg Lys
                275                 280                 285

Phe Ser Tyr Arg Ser Arg Val Arg Pro Cys Val Val Tyr Gly Gly Ala
290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
                340                 345                 350

Leu Asp Met Gly Phe Glu Pro Gln Ile Arg Arg Ile Val Glu Gln Asp
            355                 360                 365

Thr Met Pro Pro Lys Gly Val Arg His Thr Met Met Phe Ser Ala Thr
370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
            435                 440                 445

Glu Thr Lys Lys Gly Ala Asp Ser Leu Glu Asp Phe Leu Tyr His Glu
            450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
                500                 505                 510

Val Ile Asn Phe Asp Leu Pro Ser Asp Ile Glu Glu Tyr Val His Arg
            515                 520                 525

Ile Gly Arg Thr Gly Arg Val Gly Asn Leu Gly Leu Ala Thr Ser Phe
            530                 535                 540
```

```
Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
            565                 570                 575

Glu His His Tyr Lys Gly Ser Ser Arg Gly Arg Ser Lys Ser Ser Arg
                580                 585                 590

Phe Ser Gly Gly Phe Gly Ala Arg Asp Tyr Arg Gln Ser Ser Gly Ala
            595                 600                 605

Ser Ser Ser Ser Phe Ser Ser Arg Ala Ser Ser Ser Arg Ser Gly
    610                 615                 620

Gly Gly Gly His Gly Ser Ser Arg Gly Phe Gly Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
                660

<210> SEQ ID NO 10
<211> LENGTH: 661
<212> TYPE: PRT
<213> ORGANISM: Mus musculus

<400> SEQUENCE: 10

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
50                  55                  60

Asp Lys Asp Ala Tyr Ser Ser Phe Gly Ser Arg Gly Asp Ser Arg Gly
65                  70                  75                  80

Lys Ser Ser Phe Phe Gly Asp Arg Gly Ser Gly Ser Arg Gly Arg Phe
                85                  90                  95

Asp Asp Arg Gly Arg Gly Asp Tyr Asp Gly Ile Gly Gly Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
210                 215                 220

Gln Thr Gly Ser Gly Lys Thr Ala Ala Phe Leu Leu Pro Ile Leu Ser
225                 230                 235                 240

Gln Ile Tyr Ala Asp Gly Pro Gly Glu Ala Leu Arg Ala Met Lys Glu
```

```
            245                 250                 255
Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
            275                 280                 285

Phe Ser Tyr Arg Ser Arg Val Arg Pro Cys Val Val Tyr Gly Gly Ala
            290                 295                 300

Glu Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
                340                 345                 350

Leu Asp Met Gly Phe Glu Pro Gln Ile Arg Arg Ile Val Glu Gln Asp
                355                 360                 365

Thr Met Pro Pro Lys Gly Val Arg His Thr Met Met Phe Ser Ala Thr
            370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ile Asp Lys Arg Ser Phe Leu Leu
                420                 425                 430

Asp Leu Leu Asn Ala Thr Gly Lys Asp Ser Leu Thr Leu Val Phe Val
                435                 440                 445

Glu Thr Lys Lys Gly Ala Asp Ser Leu Glu Asp Phe Leu Tyr His Glu
            450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
            515                 520                 525

Ile Gly Arg Thr Gly Arg Val Gly Asn Leu Gly Leu Ala Thr Ser Phe
            530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Phe
                565                 570                 575

Glu His His Tyr Lys Gly Ser Ser Arg Gly Arg Ser Lys Ser Arg Phe
                580                 585                 590

Ser Gly Gly Phe Gly Ala Arg Asp Tyr Arg Gln Ser Ser Gly Ala Ser
            595                 600                 605

Ser Ser Ser Phe Ser Ser Ser Arg Ala Ser Ser Ser Arg Ser Gly Gly
            610                 615                 620

Gly Gly His Gly Gly Ser Arg Gly Phe Gly Gly Gly Tyr Gly Gly
625                 630                 635                 640

Phe Tyr Asn Ser Asp Gly Tyr Gly Gly Asn Tyr Asn Ser Gln Gly Val
                645                 650                 655

Asp Trp Trp Gly Asn
            660
```

<210> SEQ ID NO 11
<211> LENGTH: 661
<212> TYPE: PRT
<213> ORGANISM: Ovis aries

<400> SEQUENCE: 11

```
Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Gly Asp Tyr Asp Gly Ile Gly Gly Arg Gly Asp
            100                 105                 110

Arg Gly Gly Phe Gly Lys Tyr Glu Arg Gly Asn Ser Arg Trp Cys Asp
        115                 120                 125

Lys Ser Asp Glu Asp Asp Trp Ser Lys Pro Leu Pro Pro Ser Glu Arg
    130                 135                 140

Leu Glu Gln Glu Leu Phe Ser Gly Gly Asn Thr Gly Ile Asn Phe Glu
145                 150                 155                 160

Lys Tyr Asp Asp Ile Pro Val Glu Ala Thr Gly Asn Asn Cys Pro Pro
                165                 170                 175

His Ile Glu Ser Phe Ser Asp Val Glu Met Gly Glu Ile Ile Met Gly
            180                 185                 190

Asn Ile Glu Leu Thr Arg Tyr Thr Arg Pro Thr Pro Val Gln Lys His
        195                 200                 205

Ala Ile Pro Ile Ile Lys Glu Lys Arg Asp Leu Met Ala Cys Ala Gln
    210                 215                 220

Thr Gly Ser Gly Lys Thr Ala Ala Phe Leu Leu Pro Ile Leu Ser Gln
225                 230                 235                 240

Ile Tyr Ser Asp Gly Pro Gly Glu Ala Leu Arg Ala Met Lys Glu Asn
                245                 250                 255

Gly Arg Tyr Gly Arg Arg Lys Gln Tyr Pro Ile Ser Leu Val Leu Ala
            260                 265                 270

Pro Thr Arg Glu Leu Ala Val Gln Ile Tyr Glu Glu Ala Arg Lys Phe
        275                 280                 285

Ser Tyr Arg Ser Arg Val Arg Pro Cys Val Val Tyr Gly Gly Ala Asp
    290                 295                 300

Ile Gly Gln Gln Ile Arg Asp Leu Glu Arg Gly Cys His Leu Leu Val
305                 310                 315                 320

Ala Thr Pro Gly Arg Leu Val Asp Met Met Glu Arg Gly Lys Ile Gly
                325                 330                 335

Leu Asp Phe Cys Lys Tyr Leu Val Leu Asp Glu Ala Asp Arg Met Leu
            340                 345                 350

Asp Met Gly Phe Glu Pro Gln Ile Arg Arg Ile Val Glu Gln Asp Thr
        355                 360                 365

Met Pro Pro Lys Gly Val Arg His Thr Met Met Phe Ser Ala Thr Phe
```

```
                370                 375                 380
Pro Lys Glu Ile Gln Met Leu Ala Arg Asp Phe Leu Asp Glu Tyr Ile
385                 390                 395                 400

Phe Leu Ala Val Gly Arg Val Gly Ser Thr Ser Glu Asn Ile Thr Gln
                405                 410                 415

Lys Val Val Trp Val Glu Glu Ser Asp Lys Arg Ser Phe Leu Leu Asp
                420                 425                 430

Leu Leu Asn Ala Thr Gly Lys Asp Ser Leu Thr Leu Val Phe Val Glu
                435                 440                 445

Thr Lys Lys Gly Ala Asp Ser Leu Glu Asp Phe Leu Tyr His Glu Gly
                450                 455                 460

Tyr Ala Cys Thr Ser Ile His Gly Asp Arg Ser Gln Arg Asp Arg Glu
465                 470                 475                 480

Glu Ala Leu His Gln Phe Arg Ser Gly Lys Ser Pro Ile Leu Val Ala
                485                 490                 495

Thr Ala Val Ala Ala Arg Gly Leu Asp Ile Ser Asn Val Lys His Val
                500                 505                 510

Ile Asn Phe Asp Leu Pro Ser Asp Ile Glu Glu Tyr Val His Arg Ile
                515                 520                 525

Gly Arg Thr Gly Arg Val Gly Asn Leu Gly Leu Ala Thr Ser Phe Phe
                530                 535                 540

Asn Glu Arg Asn Ile Asn Ile Thr Lys Asp Leu Leu Asp Leu Leu Val
545                 550                 555                 560

Glu Ala Lys Gln Glu Val Pro Ser Trp Leu Glu Asn Met Ala Tyr Glu
                565                 570                 575

His His Tyr Lys Gly Ser Ser Arg Gly Arg Ser Lys Ser Ser Arg Phe
                580                 585                 590

Ser Gly Gly Phe Gly Ala Arg Asp Tyr Arg Gln Ser Ser Gly Gly Ser
                595                 600                 605

Ser Ser Ser Phe Ser Ser Ser Arg Ala Ser Ser Arg Ser Gly Gly
                610                 615                 620

Gly Gly His Gly Ser Ser Arg Gly Phe Gly Gly Gly Tyr Gly Gly
625                 630                 635                 640

Phe Tyr Asn Ser Asp Gly Tyr Gly Gly Asn Tyr Asn Ser Gln Gly Val
                645                 650                 655

Asp Trp Trp Gly Asn
                660

<210> SEQ ID NO 12
<211> LENGTH: 660
<212> TYPE: PRT
<213> ORGANISM: Bos taurus

<400> SEQUENCE: 12

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
                20                  25                  30

Ala Ser Lys Gly Arg Tyr Ile Pro Pro His Leu Arg Asn Arg Glu Ala
                35                  40                  45

Thr Lys Gly Phe Tyr Asp Lys Asp Ser Ser Gly Trp Ser Ser Ser Lys
                50                  55                  60

Asp Lys Asp Ala Tyr Ser Ser Phe Gly Ser Arg Ser Asp Ser Arg Gly
65                  70                  75                  80
```

-continued

```
Lys Ser Ser Phe Phe Ser Asp Arg Gly Ser Gly Arg Gly Arg Phe
                85                  90                  95

Asp Asp Arg Gly Arg Gly Asp Tyr Asp Gly Ile Gly Arg Gly Asp
            100                 105                 110

Arg Gly Gly Phe Gly Lys Tyr Glu Arg Gly Asn Ser Arg Trp Cys Asp
            115                 120                 125

Lys Ser Asp Glu Asp Trp Ser Lys Pro Leu Pro Pro Ser Glu Arg
            130                 135                 140

Leu Glu Gln Glu Leu Phe Ser Gly Gly Asn Thr Gly Ile Asn Phe Glu
145                 150                 155                 160

Lys Tyr Asp Asp Ile Pro Val Glu Ala Thr Gly Asn Asn Cys Pro Pro
                165                 170                 175

His Ile Glu Ser Phe Ser Asp Val Glu Met Gly Glu Ile Ile Met Gly
            180                 185                 190

Asn Ile Glu Leu Thr Arg Tyr Thr Arg Pro Thr Pro Val Gln Lys His
            195                 200                 205

Ala Ile Pro Ile Ile Lys Glu Lys Arg Asp Leu Met Ala Cys Ala Gln
210                 215                 220

Thr Gly Ser Gly Lys Thr Ala Ala Phe Leu Leu Pro Ile Leu Ser Gln
225                 230                 235                 240

Ile Tyr Ser Asp Gly Pro Gly Glu Ala Leu Arg Ala Met Lys Glu Asn
                245                 250                 255

Gly Arg Tyr Gly Arg Arg Lys Gln Tyr Pro Ile Ser Leu Val Leu Ala
            260                 265                 270

Pro Thr Arg Glu Leu Ala Val Gln Ile Tyr Glu Glu Ala Arg Lys Phe
            275                 280                 285

Ser Tyr Arg Ser Arg Val Arg Pro Cys Val Val Tyr Gly Gly Ala Asp
290                 295                 300

Ile Gly Gln Gln Ile Arg Asp Leu Glu Arg Gly Cys His Leu Leu Val
305                 310                 315                 320

Ala Thr Pro Gly Arg Leu Val Asp Met Met Glu Arg Gly Lys Ile Gly
                325                 330                 335

Leu Asp Phe Cys Lys Tyr Leu Val Leu Asp Glu Ala Asp Arg Met Leu
            340                 345                 350

Asp Met Gly Phe Glu Pro Gln Ile Arg Arg Ile Val Glu Gln Asp Thr
            355                 360                 365

Met Pro Pro Lys Gly Val Arg His Thr Met Met Phe Ser Ala Thr Phe
370                 375                 380

Pro Lys Glu Ile Gln Met Leu Ala Arg Asp Phe Leu Asp Glu Tyr Ile
385                 390                 395                 400

Phe Leu Ala Val Gly Arg Val Gly Ser Thr Ser Glu Asn Ile Thr Gln
                405                 410                 415

Lys Val Val Trp Val Glu Glu Ser Asp Lys Arg Ser Phe Leu Leu Asp
            420                 425                 430

Leu Leu Asn Ala Thr Gly Lys Asp Ser Leu Thr Leu Val Phe Val Glu
            435                 440                 445

Thr Lys Lys Gly Ala Asp Ser Leu Glu Asp Phe Leu Tyr His Glu Gly
450                 455                 460

Tyr Ala Cys Thr Ser Ile His Gly Asp Arg Ser Gln Arg Asp Arg Glu
465                 470                 475                 480

Glu Ala Leu His Gln Phe Arg Ser Gly Lys Ser Pro Ile Leu Val Ala
                485                 490                 495

Thr Ala Val Ala Ala Arg Gly Leu Asp Ile Ser Asn Val Lys His Val
```

```
                    500                 505                 510
Ile Asn Phe Asp Leu Pro Ser Asp Ile Glu Glu Tyr Val His Arg Ile
            515                 520                 525

Gly Arg Thr Gly Arg Val Gly Asn Leu Gly Leu Ala Thr Ser Phe Phe
            530                 535                 540

Asn Glu Arg Asn Ile Asn Ile Thr Lys Asp Leu Leu Asp Leu Leu Val
545                 550                 555                 560

Glu Ala Lys Gln Glu Val Pro Ser Trp Leu Glu Asn Met Ala Tyr Glu
                565                 570                 575

His His Tyr Lys Gly Ser Ser Arg Gly Arg Ser Lys Ser Arg Phe Ser
            580                 585                 590

Gly Gly Phe Gly Ala Arg Asp Tyr Arg Gln Ser Ser Gly Gly Ser Ser
            595                 600                 605

Ser Ser Phe Ser Ser Arg Ala Ser Ser Arg Ser Gly Gly Gly
            610                 615                 620

Gly His Gly Ser Ser Arg Gly Phe Gly Gly Gly Tyr Gly Ser Phe
625                 630                 635                 640

Tyr Asn Ser Asp Gly Tyr Gly Asn Tyr Asn Ser Gln Gly Val Asp
                645                 650                 655

Trp Trp Gly Asn
            660

<210> SEQ ID NO 13
<211> LENGTH: 660
<212> TYPE: PRT
<213> ORGANISM: Capra hircus

<400> SEQUENCE: 13

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Gly Asp Tyr Asp Gly Ile Gly Arg Gly Asp
            100                 105                 110

Arg Gly Gly Phe Gly Lys Tyr Glu Arg Gly Asn Ser Arg Trp Cys Asp
        115                 120                 125

Lys Ser Asp Glu Asp Asp Trp Ser Lys Pro Leu Pro Pro Ser Glu Arg
    130                 135                 140

Leu Glu Gln Glu Leu Phe Ser Gly Gly Asn Thr Gly Ile Asn Phe Glu
145                 150                 155                 160

Lys Tyr Asp Asp Ile Pro Val Glu Ala Thr Gly Asn Asn Cys Pro Pro
                165                 170                 175

His Ile Glu Ser Phe Ser Asp Val Glu Met Gly Glu Ile Ile Met Gly
            180                 185                 190

Asn Ile Glu Leu Thr Arg Tyr Thr Arg Pro Thr Pro Val Gln Lys His
        195                 200                 205
```

```
Ala Ile Pro Ile Ile Lys Glu Lys Arg Asp Leu Met Ala Cys Ala Gln
210                 215                 220
Thr Gly Ser Gly Lys Thr Ala Ala Phe Leu Leu Pro Ile Leu Ser Gln
225                 230                 235                 240
Ile Tyr Ser Asp Gly Pro Gly Glu Ala Leu Arg Ala Met Lys Glu Asn
        245                 250                 255
Gly Arg Tyr Gly Arg Arg Lys Gln Tyr Pro Ile Ser Leu Val Leu Ala
            260                 265                 270
Pro Thr Arg Glu Leu Ala Val Gln Ile Tyr Glu Glu Ala Arg Lys Phe
        275                 280                 285
Ser Tyr Arg Ser Arg Val Arg Pro Cys Val Val Tyr Gly Gly Ala Asp
290                 295                 300
Ile Gly Gln Gln Ile Arg Asp Leu Glu Arg Gly Cys His Leu Leu Val
305                 310                 315                 320
Ala Thr Pro Gly Arg Leu Val Asp Met Met Glu Arg Gly Lys Ile Gly
                325                 330                 335
Leu Asp Phe Cys Lys Tyr Leu Val Leu Asp Glu Ala Asp Arg Met Leu
            340                 345                 350
Asp Met Gly Phe Glu Pro Gln Ile Arg Arg Ile Val Glu Gln Asp Thr
        355                 360                 365
Met Pro Pro Lys Gly Val Arg His Thr Met Met Phe Ser Ala Thr Phe
370                 375                 380
Pro Lys Glu Ile Gln Met Leu Ala Arg Asp Phe Leu Asp Glu Tyr Ile
385                 390                 395                 400
Phe Leu Ala Val Gly Arg Val Gly Ser Thr Ser Glu Asn Ile Thr Gln
                405                 410                 415
Lys Val Val Trp Val Glu Glu Ser Asp Lys Arg Ser Phe Leu Leu Asp
            420                 425                 430
Leu Leu Asn Ala Thr Gly Lys Asp Ser Leu Thr Leu Val Phe Val Glu
        435                 440                 445
Thr Lys Lys Gly Ala Asp Ser Leu Glu Asp Phe Leu Tyr His Glu Gly
        450                 455                 460
Tyr Ala Cys Thr Ser Ile His Gly Asp Arg Ser Gln Arg Asp Arg Glu
465                 470                 475                 480
Glu Ala Leu His Gln Phe Arg Ser Gly Lys Ser Pro Ile Leu Val Ala
                485                 490                 495
Thr Ala Val Ala Ala Arg Gly Leu Asp Ile Ser Asn Val Lys His Val
            500                 505                 510
Ile Asn Phe Asp Leu Pro Ser Asp Ile Glu Glu Tyr Val His Arg Ile
        515                 520                 525
Gly Arg Thr Gly Arg Val Gly Asn Leu Gly Leu Ala Thr Ser Phe Phe
530                 535                 540
Asn Glu Arg Asn Ile Asn Ile Thr Lys Asp Leu Leu Asp Leu Leu Val
545                 550                 555                 560
Glu Ala Lys Gln Glu Val Pro Ser Trp Leu Glu Asn Met Ala Tyr Glu
                565                 570                 575
His His Tyr Lys Gly Ser Ser Arg Gly Arg Ser Lys Ser Arg Phe Ser
            580                 585                 590
Gly Gly Phe Gly Ala Arg Asp Tyr Arg Gln Ser Ser Gly Ser Ser Ser
        595                 600                 605
Ser Ser Phe Ser Ser Ser Arg Ala Ser Ser Arg Ser Gly Gly Gly Gly
610                 615                 620
Gly His Gly Ser Ser Arg Gly Phe Gly Gly Gly Gly Tyr Gly Gly Phe
```

```
625                630                635                640
Tyr Asn Ser Asp Gly Tyr Gly Gly Asn Tyr Asn Ser Gln Gly Val Asp
                645                650                655
Trp Trp Gly Asn
            660
```